United States Patent
Palmer et al.

(10) Patent No.: US 9,243,015 B2
(45) Date of Patent: Jan. 26, 2016

(54) METALLOCORROLES

(71) Applicant: California Institute of Technology, Pasadena, CA (US)

(72) Inventors: Joshua H. Palmer, Pasadena, CA (US); Zeev Gross, Petach Tikva (IL); Harry B. Gray, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/177,064

(22) Filed: Feb. 10, 2014

(65) Prior Publication Data
US 2014/0179918 A1 Jun. 26, 2014

Related U.S. Application Data

(62) Division of application No. 12/800,871, filed on May 24, 2010, now Pat. No. 8,680,266.

(60) Provisional application No. 61/180,749, filed on May 22, 2009.

(51) Int. Cl.
*C07D 487/22* (2006.01)
*C07F 15/00* (2006.01)

(52) U.S. Cl.
CPC ......... *C07F 15/0033* (2013.01); *C07F 15/0053* (2013.01); *C07F 15/0093* (2013.01)

(58) Field of Classification Search
CPC .................................................. C07D 487/22
See application file for complete search history.

(56) References Cited

U.S. PATENT DOCUMENTS 6,939,963 B2 9/2005 Gross et al.

OTHER PUBLICATIONS

Barata et al. β, β'—Corrole dimers. Tetrahedron Letters, 2006, 47, 8171.*
Agadjanian, et al., "Specific Delivery of Corroles to Cells via Noncovalent Conjugates with Viral Proteins," Pharmaceutical Research, 23(2), Feb. 2006, pp. 367-377.
Agadjanian, et al., "Tumor detection and elimination by a targeted gallium corrole," PNAS, 106(15), Apr. 14, 2009, pp. 6105-6110.
Antipas, et al., "Porphyrins. 38. Redox Potentials, Charge Transfer Transitions, and Emission of Copper, Silver, and Gold Complexes," Journal of the American Chemical Society, 100(24), Nov. 22, 1978, pp. 7705-7709.
Aviv, et al., "Corrole-based applications," Chem. Commun., 2007, pp. 1987-1999.
Aviv-Harel, et al., "Aura of Corroles," Chem. Eur. J., 15, 2009, pp. 8382-8394.

Baik, et al., "Computing Redox Potentials in Solution: Density Functional Theory as a Tool for Rational Design of Redox Agents," J. Phys. Chem. A, 106, 2002, pp. 7407-7412.
Balazs, et al., "High-resolution NMR spectroscopic trends and assignment rules of metal-free, metallated and substituted corroles," Magn. Reson. Chem., 42, 2004, pp. 624-635.
Becke, "Density-functional exchange-energy approximation with correct asymptotic behavior," Physical Review A, 38(6), Sep. 15, 1998, pp. 3098-3100.
Bendix, et al., "Structural, Electrochemical, and Photophysical Properties of Gallium(III) 5,10,15-Tris(pentafluorophenyl)corrole," Angew, Chem. Int. Ed., 39(22), 2000, pp. 4048-4051.
Brown, et al., "Effect of Extraplanar Ligands on the Redox Properties and the Site of Oxidation in Iron, Ruthenium, and Osmium Porphyrin Complexes," Journal of the American Chemical Society, 97(19), Sep. 17, 1975, pp. 5385-5390.
Calogero, et al., "Absorption Spectra, Luminescence Properties, and Electrochemical Behavior of Cyclometalated Iridium(III) and Rhodium(III) Complexes with a Bis(pyridyl)triazole Ligand," Inorg. Chem., 34, 1995, pp. 541-545.
Cape, et al., "Pathways of Water Oxidation Catalyzed by Ruthenium "Blue Dimers" Characterized by $^{18}$O-Isotopic Labeling," Inorg. Chem., 48, 2009, pp. 8729-8735.
Chen, et al., "Medium Effects on Charge Transfer in Metal Complexes," Chem. Rev., 98, 1998, pp. 1439-1477.

(Continued)

*Primary Examiner* — Brian McDowell
(74) *Attorney, Agent, or Firm* — Christie, Parker & Hale, LLP

(57) ABSTRACT

Metallocorrole complexes of third row transition metals (see Formula I below) may be used as therapeutic agents, catalysts, components of oxygen detectors, and components of light emitting diodes. In particular, metallocorrole complexes of third row transition metals may be used as improved photosenitizers in photodynamic therapy; as improved catalysts in aziridination, epoxidation, and water splitting reactions; as improved in vivo imaging agents; and as improved components in the emissive layer of OLEDs. Due to their strongly sigma-donating nature, corroles are able to stabilize third row transition metals in high oxidation states. Third row transition metals are significantly more electropositive than their first and second row counterparts and may therefore act as improved catalysts. In addition, the high spin-orbit coupling constants of third row transition metals may lead to easier singlet-triplet inter-system crossing in the excited state, which in turn may allow for long-wavelength phosphorescence that is desirable for many applications.

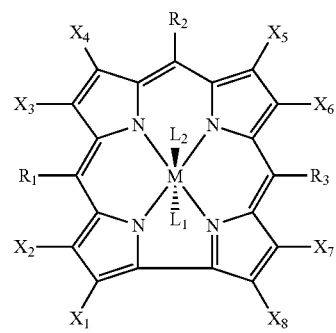

6 Claims, 46 Drawing Sheets

(56) References Cited

OTHER PUBLICATIONS

Cheung, et al., "Base-Promoted Selective Activation of Benzylic Carbon-Hydrogen Bonds of Toluenes by Iridium(III) Porphyrin," Organometallics, 27, 2008, pp. 3043-3055.

Chiorescu, et al., "Computational Electrochemistry of Ruthenium Anticancer Agents. Unprecedented Benchmarking of Implicit Solvation Methods," J. Chem. Theory Comput., 4, 2008, pp. 499-506.

Collman, et al., "Electrocatalytic Reduction of Dioxygen to Water by Iridium Porphyrins Adsorbed on Edge Plane Graphite Electrodes," Inorg. Chem., 34, 1995, pp. 1311-1324.

Crowhurst, et al., "Synthesis and Characterization of the Nitrides of Platinum and Iridium," Science, 311, Mar. 3, 2006, pp. 1275-1278.

Cui, et al., "Factors contributing to one-electron metalloradical activation of ethene and carbon monoxide illustrated by reactions of Co(II), Rh(II), and Ir(II) porphyrins," Journal of Organometallic Chemistry, 692, 2007, pp. 3198-3206.

De Bruin, et al., "Paramagnetic (Alkene)Rh and (Alkene)Ir Complexes: Metal or Ligand Radicals?" Eur. J. Inorg. Chem., 2007, pp. 211-230.

Deng, et al., Quantum chemical investigation of a dinuclear iridium porphyrin and its dipositive π-cation biradical, Chemical Physics, 321, 2006, pp. 133-139.

Ding, et al., "Photophysical Properties of a Series of Free-Base Corroles," J. Phys. Chem. A, 109, 2005, pp. 7411-7417.

Diversi, et al., "Electron Transfer Catalysis in the Activation of C-H bonds by Iridium Complexes," Organometallics, 14, 1995, pp. 3275-3287.

Diversi, et al., "Synthesis and some reactivity of cationic alkyl nitrosyl iridium(III) derivatives," Journal of Oganometallic Chemistry, 584, 1999, pp. 73-86.

Dixon, et al., "A family of luminescent coordination compounds: iridium(III) polyimine complexes," Chem. Soc. Rev., 29, 2000, pp. 385-391.

Flamigni, et al., "Switching of Electron- to Energy-Transfer by Selective Excitation of Different Chromophores in Arrays Based on Porphyrins and a Polypyridyl Iridium Complex," J. Phys. Chem. B, 106, 2002, pp. 6663-6671.

Flamigni, et al., "Photoactive corrole-based arrays," Chem. Soc. Rev., 38, 2009, pp. 1635-1646.

Fuhrhop, et al., "The Redox Behavior of Metallo Octaethylporphyrins," Journal of the American Chemical Society, 95(16), Aug. 8, 1973, pp. 5140-5147.

Gershman, et al., "DNA Binding and Catalytic Properties of Positively Charged Corroles," Angew. Chem. Int. Ed., 46, 2007, pp. 4320-4324.

Ghosh, et al., "Electronic Structure of Gallium, Copper, and Nickel Complexes of Corrole. High-Valent Transition Metal Centers versus Noninnocent Ligands," J. Am. Chem. Soc., 122, 2000, pp. 5100-5104.

Ghosh, et al., "High-valent transition metal centers versus noninnocent ligands in metallocorroles: insights from electrochemistry and implications for high-valent heme protein intermediates," Journal of Inorganic Biochemistry, 91, 2002, pp. 423-436.

Goldberg, "Corrolazines: New Frontiers in High-Valent Metalloporphyrinoid Stability and Reactivity," Acc. Chem. Res., 40, 2007, pp. 626-634.

Golombek, et al., "Quantitative analysis of dinuclear manganese(II) EPR spectra," Journal of Magnetic Resonance, 165, 2003, pp. 33-48.

Golubkov, et al., "High-Valent Manganese Corroles and the First Perhalogenated Metallocorrole Catalyst," Angew. Chem. Int. Ed., 40(11), 2001, pp. 2132-2134.

Golubkov, et al., "Chromium(V) and Chromium(VI) Nitrido Complexes of Tris(pentafluorophenyl)corrole," Angew. Chem. Int. Ed., 42, 2003, pp. 4507-4510.

Green, "Evidence for Sulfur-Based Radicals in Thiolate Compound I Intermediates," J. Am. Chem. Soc., 121, 1999, pp. 7939-7940.

Grodkowski, et al., "Reduction of Cobalt and Iron Corroles and Catalyzed Reduction of $CO_2$," J. Phys. Chem. A, 106, 2002, pp. 4772-4778.

Gross, et al., "The First Direct Synthesis of Corroles from Pyrrole," Angew. Chem. Int. Ed., 38(10), 1999, pp. 1427-1429.

Gross, et al., "Epoxidation Catalysis by a Manganese Corrole and Isolation of an Oxomanganese(v) Corrole," Angew. Chem. Int. Ed., 39(22), 2000, pp. 4045-4047.

Gross, et al., "High-valent corrole metal complexes," J. Biol. Inorg. Chem., 6, 2001, pp. 733-738.

Gross, et al., "Oxidations Catalyzed by Metallocorroles," Adv. Synth. Catal., 346, 2004, pp. 165-170.

Gross, et al., "How Do Corroles Stabilize High Valent Metals?" Comments on Inorganic Chemistry, 27, 2006, pp. 61-72.

Gryko, et al., "Recent advances in the chemistry of corroles and core-modified corroles," J. Porphyrins Phthalocyanines, 8, 2004, pp. 1091-1105.

Haber, et al., "Amphiphilic/Bipolar Metallocorroles That Catalyze the Decomposition of Reactive Oxygen and Nitrogen Species, Rescue Lipoproteins from Oxidative Damage, and Attenuate Atherosclerosis in Mice," Angew. Chem. Int. Ed., 47, 2008, pp. 7896-7900.

Han, et al., "Direct evidence for an iron(IV)-oxo porphyrin π-cation radical as an active oxidant in catalytic oxygenation reactions," Chem. Commun., 2008, pp. 1076-1078.

Hansch, et al., "A Survey of Hammett Substituent Constants and Resonance and Field Parameters," Chem. Rev., 91, 1991, pp. 165-195.

Hariharan, et al., "The Influence of Polarization Functions on Molecular Orbital Hydrogenation Energies," Theoret. chim. Acta (Berl.), 28, 1973, pp. 213-222.

Hay, et al., "Ab initio effective core potentials for molecular calculations. Potentials for K to Au including the outermost core orbitals," J. Chem. Phys., 82(1), Jan. 1, 1985, pp. 299-310.

Hehre, et al., "Self-Consistent Molecular Orbital Methods. XII. Further Extensions of Gaussian-Type Basis Sets for Use in Molecular Orbital Studies of Organic Molecules," J. Chem. Phys., 56(5), Mar. 1, 1972, pp. 2257-2261.

Henriksson, et al., "Semiempirical Molecular Orbital Studies of Phthalocyanines," Theoret. chim. Acta (Berl.), 27, 1972, pp. 213-222.

Hocking, et al., "Fe L- and K-edge XAS of Low-Spin Ferric Corrole; Bonding and Reactivity Relative to Low-Spin Ferric Porphyrin," Inorg. Chem., 48(4), 2009, pp. 1678-1688.

Hung, et al., "Blue-emitting Ir(III) phosphors with ancillary 4,6-difluorobenzyl diphenylphosphine based cyclometalate," Dalton Trans., 2009, pp. 6472-6475.

Hwang, et al., "Large Field of View Scanning Fluorescence Lifetime Imaging System for Multimode Optical Imaging of Small Animals," Proc. of SPIE, 6859, 2008, pp. 68590G-1-68590G-8.

Kadish, et al., "Electrochemical and Spectroelectrochemical Studies of $(TPP)[Ir(CO)_3]_2$ in Nonaqueous Media," Organometallics, 7, 1988, pp. 1979-1983.

Kadish, et al., "Clarification of the Oxidation State of Cobalt Corroles in Heterogeneous and Homogeneous Catalytic Reduction of Dioxygen," Inorg. Chem., 47(15), 2008, pp. 6726-6737.

Kerber, et al., "High-valent transition metal corrolazines," Journal of Inorganic Biochemistry, 100, 2006, pp. 838-857.

King, et al., "Dual Emission from an Ortho-Metalated Ir(III) Complex," J. Am. Chem. Soc., 109, 1987, pp. 1589-1590.

Koszarna, et al., "Efficient Synthesis of meso-Substituted Corroles in a $H_2O$-MeOH Mixture," J. Org. Chem. 71, 2006, pp. 3707-3717.

Kowalska, et al., "Ground- and Excited-State Dynamics of Aluminum and Gallium Corroles," Inorg. Chem., 48(6), 2009, pp. 2670-2676.

Kwong, et al., "Efficient, Saturated Red Organic Light Emitting Devices Based on Phosphorescent Platinum(II) Porphyrins," Chem. Mater., 11, 1999, pp. 3709-3713.

Lakowicz, "Principles of Fluorescence Spectroscopy," Kluwer Academic/Plenum Publishers, New York, Second Edition, 1999, pp. 207-213.

Lee, et al., "Development of the Colle-Salvetti correlation-energy formula into a functional of the electron density," Physical Review B, 37(2), Jan. 15, 1988, pp. 785-789.

Li, et al., "Base-Promoted Silicon-Hydrogen Bond Activation of Silanes by Iridium(III) Porphyrin Complexes," Organometallics, 27, 2008, pp. 4034-4042.

(56) References Cited

OTHER PUBLICATIONS

Liu, et al. "Photophysics of Soret-excited tetrapyrroles in solution. III. Porphyrin analogues: Aluminum and gallium corroles," Chemical Physics Letters, 459, 2008, pp. 113-118.
Loew, et al., "Role of the Heme Active Site and Protein Environment in Structure, Spectra, and Function of the Cytochrome P450s," Chem. Rev., 100, 2000, pp. 407-419.
Luobeznova, et al., "Synthesis and Full Characterization of Molybdenum and Antimony Corroles and Utilization of the Latter Complexes as Very Efficient Catalysts for Highly Selective Aerobic Oxygenation Reactions," Inorg. Chem., 45(1), 2006, pp. 386-394.
Mahammed, et al. "Synthesis and Structural Characterization of a Novel Covalently-Bound Corrole Dimer," Chem. Eur. J., 7(19), 2001, pp. 4259-4265.
Mahammed, et al. "Aerobic Oxidations Catalyzed by Chromium Corroles," J. Am. Chem. Soc., 125, 2003, pp. 1162-1163.
Mahammed, et al. "Iron and Manganese Corroles Are Potent Catalysts for the Decomposition of Peroxynitrite," Angew. Chem. Int. Ed., 45, 2006, pp. 6544-6547.
Mandimutsira, et al., "A Stable Manganese(V)-Oxo Corrolazine Complex," J. Am. Chem. Soc., 124, 2002, pp. 15170-15171.
Marcus, "On the Theory of Shifts and Broadening of Electronic Spectra of Polar Solutes in Polar Media," The Journal of Chemical Physics, 43(4), Aug. 15, 1965, pp. 1261-1274.
Martin, et al., "Correlation consistent valence basis sets for use with the Stuttgart-Dresden-Bonn relativistic effective core potentials: The atoms Ga—Kr and In—Xe," Journal of Chemical Physics, 114(8), Feb. 22, 2001, pp. 3408-3420.
Mcdaniel, et al., "Cyclometalated Iridium(III) Aquo Complexes: Efficient and Tunable Catalysts for the Homogeneous Oxidation of Water," J. Am. Chem. Soc., 130, 2008, pp. 210-217.
Meier-Callahan, et al., "Chromium-Corroles in Four Oxidation States," Inorg. Chem., 40, 2001, pp. 6788-6793.
Mody, et al., "Solvent effects on the electronic and vibrational properties of high-valent oxomolybdenum(V) 5,10,15-triphenylcorrole probed by UV-visible and resonance Raman spectroscopy," J. Porphyrins Phthalocyanines, 13, 2009, pp. 1040-1052.
Nardis, et al., "Novel Aspects of Corrole Chemistry," Mini-Reviews in Organic Chemistry, 2, 2005, pp. 355-374.
Nardis, et al., "Synthesis and Functionalization of Germanium Triphenylcorrolate: The First Example of a Partially Brominated Corrole," Eur. J. Inorg. Chem., 2007, pp. 2345-2352.
Okun, et al., "Manganese Corroles Prevent Intracellular Nitration and Subsequent Death of Insulin-Producing Cells," ACS Chemical Biology, 4(11), 2009, pp. 910-914.
Ou, et al., "β-Pyrrole brominated meso-tetraphenylporphyrins: synthesis, spectral and electrochemical properties," J. Porphyrins Phthalocyanines, 8, 2004, pp. 201-214.
Ou, et al., "Manganese(III) and manganese(IV) corroles: synthesis, spectroscopic, electrochemical and X-ray structural characterization," J. Porphyrins Phthalocyanines, 9, 2005, pp. 398-412.
Palmer, et al., "Iridium Corroles", J. Am. Chem. Soc., 2008, 130, pp. 7786-7787.
Paolesse, et al., "5,10,15-Triphenylcorrole: a product from a modified Rothemund reaction," Chem. Commun., 1999, pp. 1307-1308.
Papkovsky, et al., "Phosphorescent Complexes of Porphyrin Ketones: Optical Properties and Application to Oxygen Sensing," Anal. Chem., 67, 1995, pp. 4112-4117.
Poulin, et al., "Photophysical Properties of a Rhodium Tetraphenylporphyrin-tin Corrole Dyad. The First Example of a Through Metal-Metal Bond Energy Transfer," Photochemistry and Photobiology, 82, 2006, pp. 171-176.
Radoń, et al., "Peculiarities of the Electronic Structure of Cytochrome P450 Compound I: CASPT2 and DFT Modeling," J. Chem. Theory Comput., 3, 2007, pp. 728-734.
Rausch, et al., "Blue Light Emitting Ir(III) Compounds for OLEDs—New Insights into Ancillary Ligand Effects on the Emitting Triplet State," J. Phys. Chem. A, 113, 2009, pp. 5927-5932.
Ringenberg, et al., "Redox-Switched Oxidation of Dihydrogen Using a Non-Innocent Ligand," J. Am. Chem. Soc., 130, 2008, pp. 788-789.
Roos, et al., "Not Innocent: Verdict from Ab Initio Multiconfigurational Second-Order Perturbation Theory on the Electronic Structure of Chloroiron Corrole," J. Phys. Chem. B, 112(45), 2008, pp. 14099-14102.
Saltsman, et al., "Synthesis, spectroscopy, and structures of new rhodium(I) and rhodium(III) corroles and catalysis thereby," Inorganica Chimica Acta, 357, 2004, pp. 3038-3046.
Shaik, et al., "P450 Enzymes: Their Structure, Reactivity, and Selectivity-Modeled by QM/MM Calculations," Chem. Rev. 110, 2010, pp. 949-1017.
Shi, et al., "Enhancement by surfactants of the activity and stability of iridium octaethyl porphyrin as an electrocatalyst for the four-electron reduction of dioxygen," Journal of Electroanalytical Chemistry, 397, 1995, pp. 321-324.
Shilov, et al., "Activation of C—H Bonds by Metal Complexes," Chem. Rev., 97, 1997, pp. 2879-2932.
Shin, et al:, "Polymorphism-induced dual phosphorescent emission from solid-state iridium(III) complex," Dalton Trans., 2009, pp. 6476-6479.
Simkhovich, et al., "Coordination Chemistry of the Novel 5,10,15-Tris(pentafluorophenyl)corrole: Synthesis, Spectroscopy, and Structural Characterization of Its Cobalt(III), Rhodium(III), and Iron(IV) Complexes," Inorg. Chem., 39, 2000, pp. 2704-2705.
Simkhovich, et al., "Iron(IV) corroles are potent catalysts for aziridination of olefins by Chloramine-T," Tetrahedron Letters, 42, 2001, pp. 8089-8092.
Simkhovich, et al., "Synthesis and Characterization of Germanium, Tin, Phosphorus, Iron, and Rhodium Complexes of Tris(pentafluorophenyl)corrole, and the Utilization of the Iron and Rhodium Corroles as Cyclopropanation Catalysts," Chem. Eur. J., 7(5), 2001, pp. 1041-1055.
Simkhovich, et al., "Iron(III) and Iron(IV) Corroles: Synthesis, Spectroscopy, Structures, and No Indications for Corrole Radicals," Inorg. Chem., 41(21), 2002, pp. 5433-5439.
Simkhovich, et al., "The effects of bulky ortho-aryl substituents in corroles, tested by X-ray crystallography of the rhodium complexes and catalysis thereby," J. Porphyrins Phthalocyanines, 6, 2002, pp. 439-444.
Simkhovich, et al., "Mono- and Binuclear Ruthenium Corroles: Synthesis, Spectroscopy, Electrochemistry, and Structural Characterization," Chem. Eur. J., 9(1), 2003, pp. 201-208.
Song, et al., "Syntheses of Acyliridium Porphyrins by Aldehydic Carbon—Hydrogen Bond Activation with Iridium(III) Porphyrin Chloride and Methyl," Organometallics, 26, 2007, pp. 965-970.
Steene, et al., "Resonance Raman spectroscopy and density functional theoretical calculations of manganese corroles. A parallelism between high-valent metallocorroles and metalloporphyrins, relevant to horseradish peroxidase and chloroperoxidase compound I and II intermediates," Journal of Inorganic Biochemistry, 88, 2002, pp. 113-118.
Stephens, et al., "Ab Initio Calculation of Vibrational Absorption and Circular Dichroism Spectra Using Density Functional Force Fields," The Journal of Physical Chemistry, 98(45), Nov. 10, 1994, pp. 11623-11627.
Sun, et al., "Photophysics of Pt-porphyrin electrophosphorescent devices emitting in the near infrared," Applied Physics Letters, 90, 2007, pp. 213503-1-213503-3.
Tait, et al., "Picosecond Studies of Ruthenium(II) and Ruthenium(III) Porphyrin Photophysics," J. Am. Chem. Soc., 107, 1985, pp. 1930-1934.
Toganoh, et al., "Bis[iridium(I)] Complex of Inverted N-Confused Porphyrin," Inorg. Chem., 45(10), 2006, pp. 3852-3854.
Tse, et al., "Synthesis of an oxorhenium(v) corrolate from porphyrin with detrifluoromethylation and ring contraction," Chem. Commun., 1998, pp. 1199-1200.
Tsuboyama, et al., "Homoleptic Cyclometalated Iridium Complexes with Highly Efficient Red Phosphorescence and Application to Organic Light-Emitting Diode," J. Am Chem. Soc., 125, 2003, pp. 12971-12979.
Walker, "Magnetic spectroscopic (EPR, ESEEM, Mössbauer, MCD and NMR) studies of low-spin ferriheme centers and their corresponding heme proteins," Coordination Chemistry Reviews, 185-186, 1999, pp. 471-534.

(56) References Cited

OTHER PUBLICATIONS

Weaver, et al., "Gallium(III) corroles," J. Porphyrins Phthalocyanines, 8, 2004, pp. 76-81.

Wiehe, et al., "PDT-related photophysical properties of conformationally distorted palladium(II) porphyrins," J. Porphyrins Phthalocyanines, 5, 2001, pp. 853-860.

Yanagisawa, et al., "Hosting Fullerenes by Dynamic Bond Formation with an Iridium Porphyrin Cyclic Dimer: A "Chemical Friction" for Rotary Guest Motions," J. Am. Chem. Soc., 129, 2007, pp. 11912-11913.

Yu, et al., "Cationic iridium(III) complexes for phosphorescence staining in the cytoplasm of living cells," Chem. Commun., 2008, pp. 2115-2117.

Zakharieva, et al., "Is the Corrolate Macrocycle Innocent or Noninnocent? Magnetic Susceptibility, Mössbauer, $^1$H NMR, and DFT Investigations of Chloro- and Phenyliron Corrolates," J. Am. Chem. Soc., 124, 2002, pp. 6636-6648.

Zenkevich, et al., "Photophysical and photochemical properties of potential porphyrin and chlorin photosensitizers for PDT," Journal of Photochemistry and Photobiology B: Biology, 33, 1996, pp. 171-180.

Zhai, et al., "Formation and ethene substrate reactions of iridium(II) porphyrin metal-centered dπ radicals," Chem. Commun., 2001, pp. 1294-1295.

Barata, et al., "β,β'-Corrole dimers", Tetrahedron Letters, vol. 47, 2006, pp. 8171-8174.

Jeyaprakash, et al., "Interaction of Rh(I) with meso-Arylsapphyrins and -Rubyrins: First Structural Characterization of Bimetallic Hetero-rubyrin Complex", Inorg. Chem., 2001, vol. 40, pp. 1637-1645.

Mahammed, et al., "Synthesis and Structural Characterization of a Novel Covalently-Bound Corrole Dimer", Chem. Eur. Journal, 2001, vol. 7, No. 19, pp. 4259-4265.

Saltsman, et al., "Synthesis, spectroscopy, and structures of new rhodium(I) and rhodium(III) corroles and catalysis thereby", Inorganica Chimica Acta, vol. 357, 2004, pp. 3038-3046.

\* cited by examiner

METALLOCORROLES

CROSS-REFERENCE TO RELATED APPLICATION(S)

This application is a divisional of U.S. application Ser. No. 12/800,871 filed May 24, 2010, which claims priority to and the benefit of U.S. Provisional Application Ser. No. 61/180,749, filed on May 22, 2009, the entire contents of which are incorporated herein by reference.

STATEMENT REGARDING FEDERALLY SPONSORED RESEARCH OR DEVELOPMENT

The U.S. Government has certain rights in this invention pursuant to Grant No. CHE0518164 awarded by the National Science Foundation.

FIELD

The present invention relates generally to metallocorrole compounds containing a third row transition metal.

BACKGROUND

Metalloporphyrin complexes that phosphoresce at ambient temperatures have been used widely in photodynamic therapy (PDT), oxygen detection, and organic light emitting diodes (OLEDs). The most commonly used metalloporphyrins are $d^8$ [primarily platinum(II), palladium(II), and gold(III)] and lanthanide complexes that emit at relatively long wavelengths (>600 nm) with lifetimes, in solution, in the 10-50 μs range under anaerobic conditions at room temperature. Although $d^6$ metalloporphyrins are known to have desirable photophysical properties, they have found limited application. For example, ruthenium(II) porphyrins phosphoresce at room temperature at wavelengths longer than those of platinum(II) analogues, but have been less commonly used, due to oxidative instabilities. Porphyrin ligands are limited, however, in their emission intensity and their ability to stabilize metals in high oxidation states.

While metalloporphyrin complexes have been widely used, they typically stabilize metals in lower oxidation states than do corroles. Accordingly, first and second row transition metal corrole complexes have been investigated in an attempt to discover compounds capable of stabilizing metals in higher oxidation states. These corrole ligands are more electron-rich, and their strong sigma-donating nature enables them to stabilize high-valent metal centers that porphyrins cannot. Higher metal oxidation states strongly affect the redox properties of the chelated metal ion, and certain high-valent metal centers are desirable for catalysis. Additionally, corrole complexes produce more intense emission than metalloporphyrins.

These first and second row transition metal corrole complexes are, however, typically limited to fluorescence emission. In addition to their therapeutic uses, first row transition metal corroles function as good catalysts. For example, such corroles can be used in the activation of $O_2$ by trivalent chromium, manganese, and iron; catalytic reduction of $CO_2$ by iron(I) and cobalt(I); and iron(IV) aziridination of olefins. The redox processes of first and second row transition metal corrole complexes are, however, more often ligand-centered than metal-centered.

SUMMARY

Embodiments of the present invention relate to metallocorroles represented by Formula I:

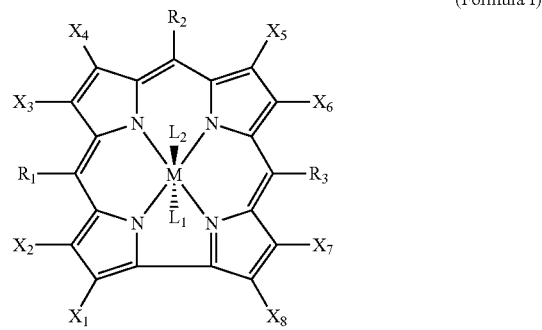

(Formula I)

In Formula I, M is selected from third row transition metals. Each of $R_1$ through $R_3$ is independently selected aryl groups and heteroaryl groups. Each of $X_1$ through $X_8$ is independently H, halides, aldehydes, carboxylic acids, cyanoacetates, sulfonyls, $SO_2Cl$, $SO_3H$, $SO_2NR_1R_2$, $CO_2H$, COCl, $CONR_4R_5$, CHO or $NO_2$, wherein $R_4$ and $R_5$ may be the same or different, and each is selected from H, alkyl, aryl, and heteroaryl; and each of $L_1$ and $L_2$ is a binding site or an axial ligand.

BRIEF DESCRIPTION OF THE DRAWINGS

The patent or application file contains at least one drawing executed in color. Copies of this patent or patent application publication with color drawing(s) will be provided by the office upon request and payment of the necessary fee.

These and other features and advantages of the present invention will be better understood by reference to the following detailed description when considered in conjunction with the attached drawings, in which.

DETAILED DESCRIPTION

Figure 1:
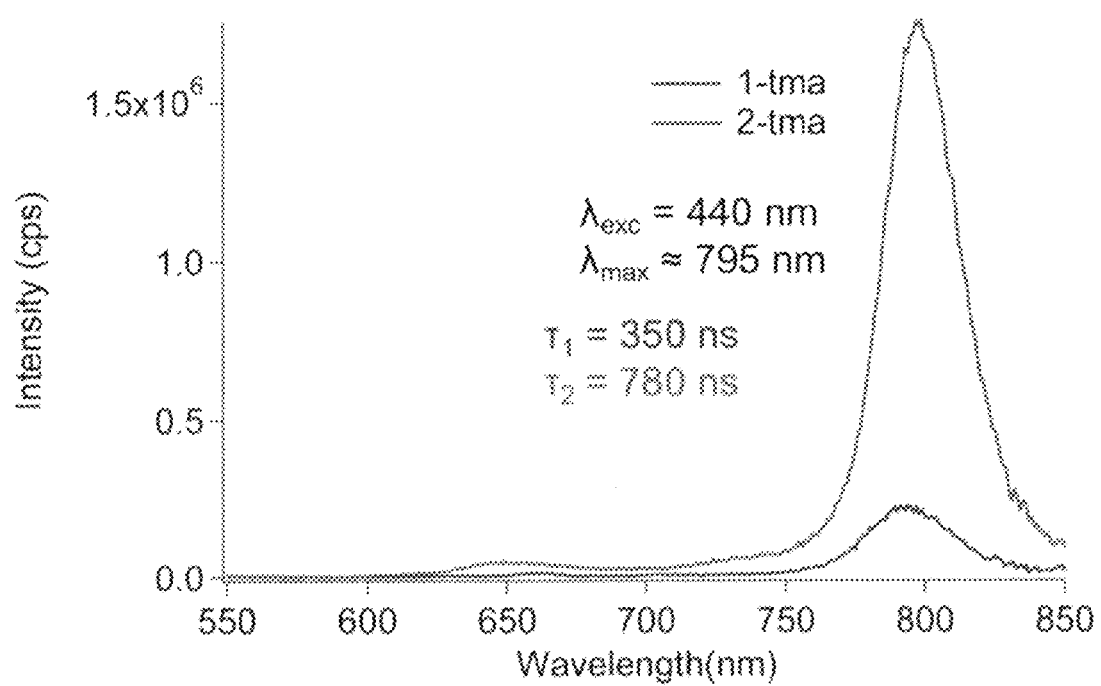
FIG. 1 is a graph of emission (phosphorescence) spectra of 1-tma and 2-tma, in $CH_2Cl_2$ solutions at room temperature.

In the following detailed description, compounds are abbreviated in a number of ways. For example, 5,10,15-tris(pentafluorophenyl)corrolato iridium(III) (trimethylamine)$_2$ may be abbreviated as 1, 1-Ir(tma)$_2$, or 1-tma. Also, 2,3,7,8,12,13,17,18-octabromo-5,10,15-tris-pentafluorophenylcorrolato-iridium(III) bis-trimethylamine may be abbreviated as 2, 1b-Ir(tma)$_2$, or 2-tma. 5,10,15-Tris-pentafluorophenylcorrolato-iridium(III) bis-pyridine may be abbreviated as 1-Ir(py)$_2$, or 1-py. 5,10,15-Tris-pentafluorophenylcorrolato-iridium(III)triphenylphosphine may be abbreviated as 1-Ir(PPh$_3$), or 1-PPh$_3$. 5,10,15-Tris-pentafluorophenylcorrolato-iridium(III)bis-cyanopyridine may be abbreviated as 1-Ir(CNpy)$_2$ or 1-CNpy. 5,10,15-Tris-pentafluorophenylcorrolato-iridium(III) bis-4-methoxypyridine may be abbreviated as 1-Ir(Opy)$_2$ or 1-MeOpy. 5,10,15-Tris-pentafluorophenylcorrolato-iridium (III)bis[3,5-bis(trifluoromethyl)pyridine] may be abbreviated as 1-Ir((CF$_3$)$_2$py)$_2$ or 1-(CF$_3$)$_2$py. 5,10,15-Tris-pentafluorophenylcorrolato-iridium(III) bis(3,5-dichloropyridine] may be abbreviated as 1-Ir(Cl$_2$py)$_2$ or 1-Cl$_2$py. Iridium(I) cyclooctadiene chloride dimer may be abbreviated as [Ir(cod)Cl]$_2$. 5,10,15-Tris-pentafluorophenylcorrole may be abbreviated as H$_3$(tpfc). 5,10,15-Tris-pentafluorophenylcorrolato trianion may be abbreviated as tpfc. 2,3,7,8,12,13,17,18-Octabromo-5,10,15-tris-pentafluorophenylcorrolato trianion may be abbreviated as Br$_8$-tpfc. Tris(4-bromophenyl) aminium hexachloroantimonate may be abbreviated as t-4bpa. Trimethylamine N-oxide may be abbreviated as tma-N-oxide. Trimethylamine may be abbreviated as tma. Pyridine may be abbreviated as py.

Embodiments of the present invention relate to metallocorroles represented by Formula I:

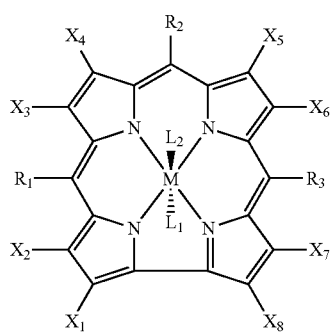

(Formula I)

In Formula I, M is selected from third row transition metals. Each of R$_1$ through R$_3$ is independently selected aryl groups and heteroaryl groups. Each of X$_1$ through X$_8$ is independently H, halides, aldehydes, carboxylic acids, cyanoacetates, sulfonyls, SO$_2$Cl, SO$_3$H, SO$_2$NR$_1$R$_2$, CO$_2$H, COCl, CONR$_4$R$_5$, CHO or NO$_2$, wherein R$_4$ and R$_5$ may be the same or different, and each is selected from H, alkyl, aryl, and heteroaryl; and each of L$_1$ and L$_2$ is a binding site or an axial ligand.

According to some embodiments of the present invention, M is an element selected from late transition metals. Late transition metals may include Os, Ir, Pt, and Au. In some alternate embodiments, M is an element selected from W, Os, Ir, Pt, and Au. In another embodiment, M is Ir.

According to an embodiment of the present invention, each of L$_1$ and L$_2$ is independently a binding site or an axial ligand selected from trimethylamine, pyridine, 4-methoxypyridine, 4-cyanopyridine, 3,5-dichloropyridine, 3,5-bis-trifluoromethylpyridine.

According to an embodiment of the present invention, each of X$_1$ through X$_8$ is independently selected from H, F, Cl, and Br.

According to an embodiment of the present invention, each of R$_1$ through R$_3$ is independently selected from phenyl, methylphenyl (para-tolyl), 4-aminophenyl, dichlorophenyl, 2,6-dichlorophenyl, 2,6-difluorophenyl, pentafluorophenyl, 4-methoxyphenyl, 2,5-dimethoxyphenyl, 4-methoxy-2,3,5,6-tetrafluorophenyl, 4-(pyrid-2-yl)-2,3,5,6-tetrafluorophenyl, 4-(N-methyl-pyrid-2-ylium)-2,3,5,6-tetrafluorophenyl, 4-pyridyl, benzaldehyde, 4-NO$_2$ benzaldehyde, 3-NO$_2$ benzaldehyde, 2-NO$_2$ benzaldehyde, 4-Br benzaldehyde, 3-Br benzaldehyde, 2-Cl benzaldehyde, 4-CH$_3$ benzaldehyde, 4-OCH$_3$ benzaldehyde, 2,5-(OCH$_3$)$_2$ benzaldehyde, F$_5$-benzaldehyde, 4-pyridinecarboxaldehyde, 2-furalaldehyde, mesitaldehyde, 2,6-(OCH$_3$)$_2$ benzaldehyde, and 2,6-Cl$_2$ benzaldehyde. The aldehyde starting materials will result in a final R group which no longer bears the aldehyde functionality, but is bound to the corrole framework by the carbon which previously bore the functionality.

According to an embodiment of the present invention, the metallocorrole of Formula I is selected from: 2,17-bis(chlorosulfonyl)-5,10,15-tris(pentafluorophenyl)corrolato M; 3,17-bis(chlorosulfonyl)-5,10,15-tris(pentafluorophenyl) corrolato M; 5,10,15-tris(pentafluorophenyl)-2,17-bis(sulfonic acid)-corrolato M; 5,10,15-tris(pentafluorophenyl)-3,17-bis(sulfonic acid)-corrolato M; 2,17-bis(piperidinosulfonyl)-5,10,15-tris(pentafluorophenyl) corrolato M; 3,17-bis(piperidinosulfonyl)-5,10,15-tris (pentafluorophenyl)corrolato M; 5,10,15-triphenylcorrolato M; 5,10,15-tris(4-nitrophenyl)corrolato M; 5,10,15-tris(2-nitrophenyl)corrolato M; 5,10,15-tris(3-nitrophenyl)corrolato M; 5,10,15-tris(4-bromophenyl)corrolato M; 5,10,15-tris(3-bromophenyl)corrolato M; 5,10,15-tris(2-chlorophenyl)corrolato M; 5,10,15-tris(4-methylphenyl)corrolato M; 5,10,15-tris(4-methoxyphenyl)corrolato M; 5,10,15-tris(2,5-dimethoxyphenyl)corrolato M; 5,10,15-tris(4-pyridyl) corrolato M; 5,10,15-tris(pentafluorophenyl)corrolato M; 2,3,7,8,12,13,17,18-octabromo-5,10,15-triphenylcorrolato M; and 2,3,7,8,12,13,17,18-octabromo-5,10,15-tris(4-nitrophenyl)corrolato M.

In one embodiment, the metallocorrole of Formula I is 5,10,15-tris(pentafluorophenyl)corrolato M.

In another embodiment, the metallocorrole of Formula I is 2,3,7,8,12,13,17,18-octabromo-5,10,15-tris(pentafluorophenyl)corrolato M.

According to an embodiment of the present invention, the metallocorrole of Formula I is selected from the group consisting of 5,10,15-tris(pentafluorophenyl)corrolato iridium (III) (trimethylamine)$_2$, 2,3,7,8,12,13,17,18-octabromo-5,10,15-tris(pentafluorophenyl)corrolato iridium(III) (trimethylamine)$_2$, 5,10,15-tris(pentafluorophenyl)corrolato iridium(III) (4-methoxypyridine)$_2$, 5,10,15-tris(pentafluorophenyl)corrolato iridium(III) (pyridine)$_2$, 5,10,15-tris(pentafluorophenyl)corrolato iridium(III) (4-cyanopyridine)$_2$, 5,10,15-tris(pentafluorophenyl)corrolato iridium(III) (3,5-dichloropyridine)$_2$, 5,10,15-tris(pentafluorophenyl)corrolato iridium(III) (3,5-bis-trifluoromethylpyridine)$_2$, 5,10,15-tris (pentafluorophenyl)corrolato iridium(III)(triphenylphosphine), and 5,10,15-tris(pentafluorophenyl)corrolato iridium (III)(triphenylphosphine)$_2$.

Embodiments of the present invention relate to metallocorroles represented by Formula II:

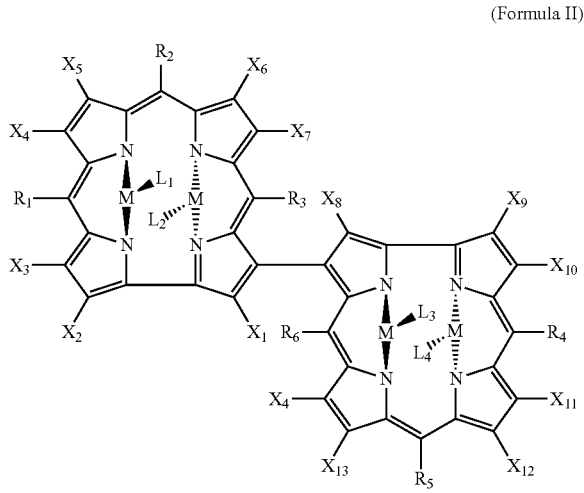

(Formula II)

In Formula II, M is a third row transition metal. Each of $R_1$ through $R_6$ is independently selected from aryl groups and heteroaryl groups. Each of $X_1$ through $X_{14}$ is independently selected from H, halides, aldehydes, carboxylic acids, cyanoacetates, sulfonyls, $SO_2Cl$, $SO_3H$, $SO_2NR_7R_8$, $CO_2H$, COCl, $CONR_7R_8$, CHO or $NO_2$, wherein $R_7$ and $R_8$ may be the same or different, and each is selected from H, alkyl, aryl, and heteroaryl. Each of $L_1$ through $L_4$ is a bidentate ligand.

In one embodiment, M is an element selected from the group consisting of late transition metals. In another embodiment, M is Pt.

According to an embodiment, each of $X_1$ through $X_{14}$ is independently selected from H, F, Cl, and Br.

According to an embodiment, each of $R_1$ through $R_6$ is independently selected from phenyl, methylphenyl (para-tolyl), 4-aminophenyl, dichlorophenyl, 2,6-dichlorophenyl, 2,6-difluorophenyl, pentafluorophenyl, 4-methoxyphenyl, 2,5-dimethoxyphenyl, 4-methoxy-2,3,5,6-tetrafluorophenyl, 4-(pyrid-2-yl)-2,3,5,6-tetrafluorophenyl, 4-(N-methyl-pyrid-2-ylium)-2,3,5,6-tetrafluorophenyl, 4-pyridyl, benzaldehyde, 4-$NO_2$ benzaldehyde, 3-$NO_2$ benzaldehyde, 2-$NO_2$ benzaldehyde, 4-Br benzaldehyde, 3-Br benzaldehyde, 2-Cl benzaldehyde, 4-$CH_3$ benzaldehyde, 4-$OCH_3$ benzaldehyde, 2,5-$(OCH_3)_2$ benzaldehyde, $F_5$-benzaldehyde, 4-pyridinecarboxaldehyde, 2-furalaldehyde, mesitaldehyde, 2,6-$(OCH_3)_2$ benzaldehyde, and 2,6-$Cl_2$ benzaldehyde. The aldehyde starting materials will result in a final R group which no longer bears the aldehyde functionality, but is bound to the corrole framework by the carbon which previously bore the functionality.

Embodiments of the present invention relate to a method of preparing a metallocorrole by mixing a metallocorrole complex of a third row transition metal and trimethylamine N-oxide.

In one embodiment, a metallocorrole complex of a third row transition metal is prepared by exposing the mixture of the metallocorrole complex including a third row transition metal and any substituted or non-substituted pyridine ligand to oxygen.

In another embodiment, a brominated metallocorrole complex of a third row transition metal is prepared by reacting a brominated metallocorrole comprising reacting a metallocorrole complex including a third row transition metal with excess $Br_2$.

Scheme 1 is an illustration of the synthesis of exemplary corrole complexes (i.e., Ir(III) corrole complexes) according to an embodiment of the present invention.

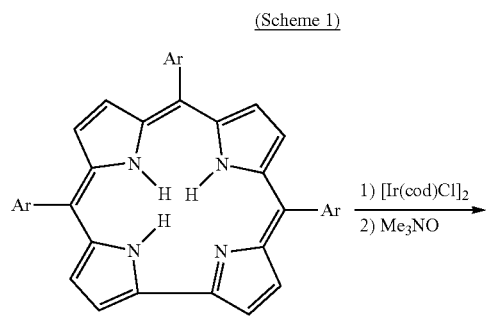

(Scheme 1)

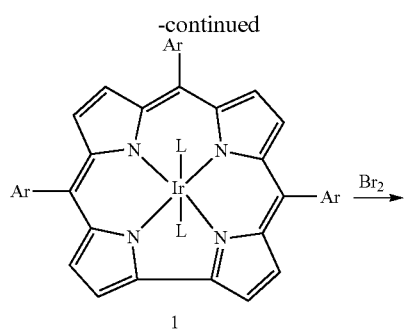

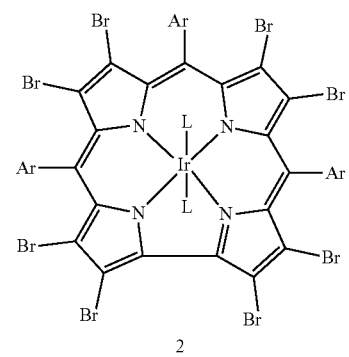

Ar = $C_6F_5$, L = $NMe_3$

Scheme 2 is an illustration of three exemplary metallocorroles according to embodiments of the present invention.

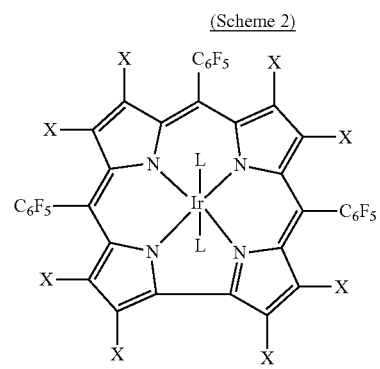

(Scheme 2)

1-Ir(tma)$_2$: X = H, L = tma
1b-Ir(tma)$_2$: X = Br, L = tma
1-Ir(py)$_2$: X = H, L = py tma = trimethylamine
py = pyridine Scheme 3 is an illustration of, clockwise from the upper left corner: an Ir(III) 2-phenylpyridine prior art complex; an Ir(III) porphyrin prior art complex; non-limiting, exemplary Ir(III) octahedral corrole complexes according to the present invention; a non-limiting, exemplary Ir(III) octahedral brominated corrole complex according to the present invention; and a non-limiting, exemplary Ir(III) five-coordinate corrole complex according to the present invention.

(Scheme 3)

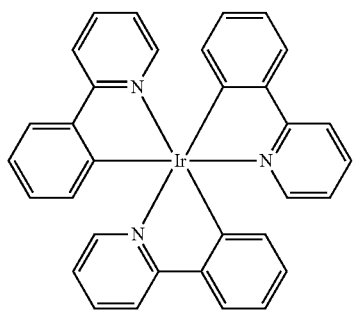

Ir(ppy)₃

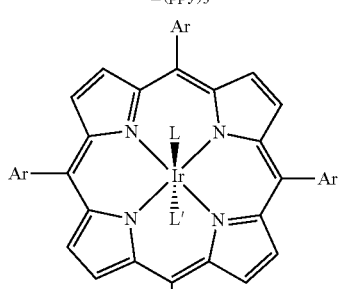

L = CO and L' = Cl
or
L = H, alkyl (and no L')

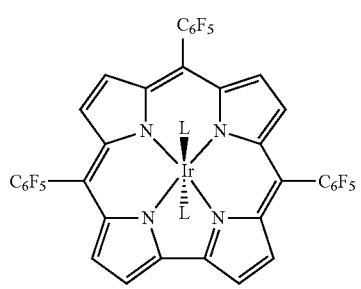

1-tma: L = trimethylamine
1-MeOpy: L = 4-methoxypyridine
1-py: L = pyridine
1-CNpy: L = 4-cyanopyridine
1-Cl₂py: L = 3,5-dichloropyridine
1-(CF₃)₂py: L = 3,5-bis-trifluoromethylpyridine

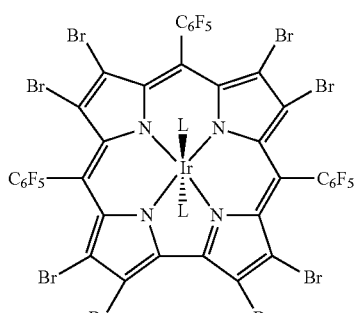

2-tma: L = trimethylamine

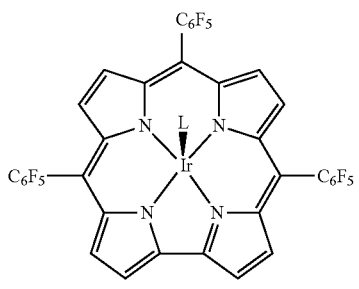

1-PPh₃: L = triphenylphosphine

Scheme 4 is an illustration of prior art iridium(III) 2-phenylpyridine and porphyrin complexes along with exemplary metallocorroles according to embodiments of the present invention.

(Scheme 4)

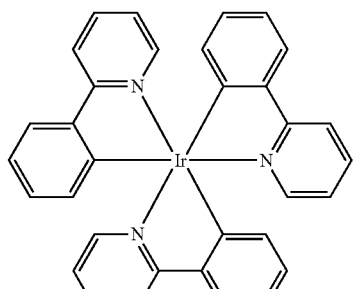

Ir(ppy)₃

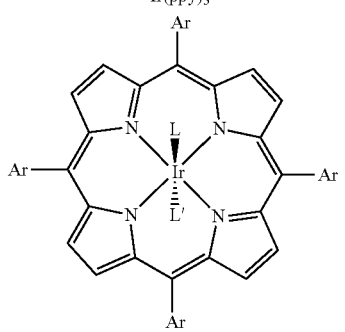

L = CO and L' = Cl
or
L = H, alkyl (and no L')

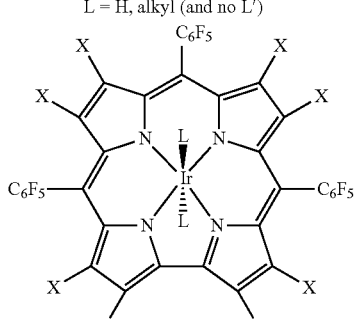

1-Ir(tma)₂: X = H, L = N(CH₃)₃
1b-Ir(tma)₂: X = Br, L = N(CH₃)₃

Scheme 5 is an illustration of axially ligated prior art rhodium(III), and cobalt(III) corroles and exemplary iridium(III) metallocorroles according to embodiments of the present invention (wherein py represents pyridine and P$\phi_3$ represents triphenylphosphine).

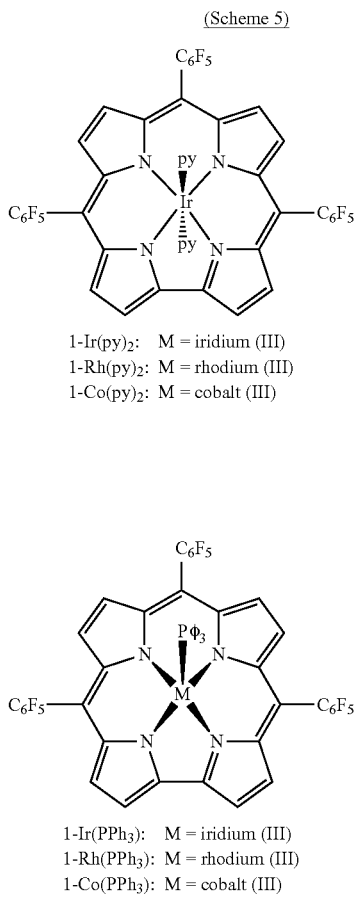

Corroles are structurally distinct from porphyrins. For example, the generic structures of both corrole and porphyrin are shown in Scheme 6 below.

As can be seen above, compared to the generic porphyrin structure, the generic corrole structure has one less methine bridge in the outer ring structure, and one more NH proton within the interior of the ring. The basic corrole structure is also a member of a lower symmetry group than the basic porphyrin structure. In addition, the generic corrole structure is chiral. Further differences between porphyrin and corrole emerge when these compounds are used as ligands. For example, when used as a ligand in a metalloporphyrin, porphyrin binds as the dianion. In contrast, in metallocorroles the corrole ligand binds as a trianionic ligand. Additional differences between metallocorroles and metalloporphyrins are set forth below.

Interest in transition metal corrole complexes has increased recently due, in large part, to the development of facile methods for the synthesis of the stable 5,10,15-tris-pentafluorophenylcorrole ("H$_3$tpfc") synthon and of other tris-aryl-substituted corroles. The first facile corrole syntheses led to scalable preparative procedures that in turn opened the way for the synthesis and study of many first- and second-row transition metal corroles. Concurrent with this increased interest, much effort has been directed toward the goal of developing new metallocorrole systems for applications including, but not limited to, medical diagnostics and therapeutics as well as catalysis. Although there has been great interest in metallocorroles, third-row transition metal corroles are very rare.

In contrast to first and second row transition metals, third row transition metals are significantly more electropositive. Thus, highly oxidized third row transition metal corrole complexes can be expected to assist in catalytic reactions in which first and second row transition metal corrole complexes do not participate. In addition, due to the large size of third row transition metal nuclei, these metals have very high spin-orbit couplings. These high spin-orbit couplings lead to easier singlet-triplet inter-system crossing in the excited state, which in turn allows for the long-wavelength phosphorescence that is desirable for many applications. For example, Iridium(III) corrole phosphorescence is observed at ambient temperature at wavelengths much longer (>800 nm) than those of most other luminescent Ir(III) complexes.

Despite the differences between metallocorroles and metalloporphyrins described herein, metallocorrole complexes may be used in the same or similar applications as their metalloporphyrin analogues. Accordingly, metallocorrole compounds may be used as improved therapeutic agents, catalysts, components of oxygen detectors, and components of organic light emitting diodes (OLEDs). In particular, metal complexes of triaryl corroles may be used as improved photosensitizers in photodynamic therapy (PDT), as improved anti-cancer agents (e.g., tumor detection and/or tumor elimination), improved catalysts for inorganic and organic reactions (e.g., aziridination and/or epoxidation reactions), improved in vivo imaging agents, and improved components of the emissive layer in OLEDs. Further, third row transition metal corrole complexes may be used as catalysts in water splitting reactions.

Concurrent with the intensified research into metallocorrole complexes, interest in the chemistry of iridium ("Ir"), a third row transition metal, also accelerated greatly, owing in part to reports of high-valent oxo and nitrido species as well as other complexes possessing wide ranging catalytic activities. While cyclometalated iridium(III) complexes such as [Ir(ppy)$_3$] (ppy=2-phenylpyridine) phosphoresce in solution with quantum yields of 0.1-0.6 and microsecond lifetimes (near 100% internal efficiencies in OLEDs), these characteristics may not translate into useful Ir(III) porphyrins. Typically, Ir(III) porphyrins are stable only when additionally coordinated by CO, hydride, or alkyl ligands [as in (por)Ir(CO)Cl and (por)Ir—R; where por is porphyrin dianion; and R=alkyl or hydride]. Thus, although Ir(III) porphyrins have been identified as potentially useful compounds, practical examples have been elusive.

In contrast to their porphyrin analogues, the strong σ-donor environment of corroles stabilizes metals in high oxidation states; this property is typified by stable nitrido chromium (VI) and manganese(VI) species. Although corroles (both metal-free and in complexes with non-redox-active elements) are prone to oxidation, it is well established that they stabilize transition metals in unusually high oxidation states. Many of these complexes, especially of first-row transition metals, exhibit striking reactivity: activation of O$_2$ by trivalent chromium, manganese, and iron; catalytic reduction of CO$_2$ by iron(I) and cobalt(I); iron(IV)-mediated aziridination of olefins; iron(IV) derivatives remain the only non-copper catalysts for the aziridination of olefins by chloramine-T; manganese(III) forms (oxo)manganese(V) during oxygenation catalysis; chromium(III) mediates the aerobic oxidation of thiophenol to diphenyl disulfide; and iron(I) and cobalt(I) corroles catalyze the reduction of carbon dioxide. These reactivity patterns highlight the role of unusually strong corrole σ-donation in the activation of low-valent metal centers. This same electronic property, which accounts for the unusual stability of nitrido chromium(VI) and manganese(VI) complexes, is an important factor in biologically relevant metallocorrole-catalyzed processes. Complexes of triarylcorroles with group 13-15 elements have been characterized, often with a focus on photophysical properties; for example, a gallium(III) corrole has been shown to be both an in vivo imaging agent and an anticancer drug candidate. Several second-row transition metals also form stable corrole complexes: (oxo)molybdenum(V); ruthenium(III), as triply bonded Ru—Ru dimers and nitric oxide bound monomers; rhodium(III), which catalyzes carbene-transfer reactions; and silver(III).

Because trianionic corroles have the ability to stabilize metals in high oxidation states, they are able to stabilize Ir(III) compounds. As a result, Ir(III) corroles can be stabilized even by weakly donating axial ligands. In addition, corroles bind Ir(III) without the aid of additional organic ligands. This is in direct contrast to Ir(III) porphyrins, which are only stable when the metal is further coordinated by organometallic ligands [such as in (por)Ir(CO)Cl and (por)Ir—R].

The inventive third row transition metal corrole complexes of the present invention display several unique features not shared with 3d and 4d metallocorrole analogues. In particular, the photophysical properties of Ir(III) corroles differ significantly from those of other luminescent metallocorroles and even other cyclometalated Ir(III) compounds. Ir(III) corrole phosphorescence is observed at ambient temperature [Ge(IV) and Sn(IV) corroles emit only at low temperatures] at wavelengths much longer (>800 nm) than those of other luminescent Ir(III) complexes. For example, 5,10,15-tris-pentafluorophenylcorrolato-iridium(III)bis-trimethylamine ("1-Ir(tma)$_2$") emits at 792 nm with a 0.35 ms lifetime and 2,3,7,8,12,13,17,18-octabromo-5,10,15-tris-pentafluorophenylcorrolato-iridium(III) bis-trimethylamine ("2-Ir(tma)$_2$") emits at 796 nm with a 0.78 ms lifetime. The phosphorescence quantum yields vary among Ir(III) corroles, with substantial dependence on corrole ring β-substituents and axial ligands. Absorption spectra display a strong positive solvatochromic effect, indicating that the excited state is much more polar than the ground state. In addition, the compounds disclosed herein display very high thermal- and photo-stability. That is, they remain intact after hours of illumination and heating.

Further differences between the metallocorroles disclosed herein and metallocorrole complexes of period 4 and 5 elements are highlighted by comparison of the very rare isostructural 3d Co(III), 4d Rh(III) and 5d Ir(III) series. Both the substitutional lability and sites of oxidation reactions change significantly within this Group 9 metallocorrole series. For example, cobalt(III) corroles are substitutionally labile compared to either Rh(III) or Ir(III) derivatives. In particular, 1-Co(PPh$_3$) reacts with pyridine to form 1-Co(py)$_2$ by way of addition and substitution reactions, 1-Rh(PPh$_3$) reacts with pyridine to form 1-Rh(PPh$_3$)(py) by way of an addition reaction, and 1-PPh$_3$ reacts with pyridine to form 1-Ir(PPh$_3$)(py) by way of an addition reaction.

In addition, the affinity of five-coordinate derivatives for a sixth ligand increases dramatically down the series. For example, addition of 100,000 fold excess of triphenylphosphine to 1-Co(PPh$_3$) produced only minor spectral changes, indicating that triphenylphosphine was not added as a sixth ligand. Adding 6300 and 350 equivalents of triphenylphosphine to I-Rh(PPh$_3$) and 1-Ir(PPh$_3$), respectively, resulted in major spectral changes, indicating addition of triphenylphosphine as a sixth ligand. Typically, corrolato-chelated metal (III) ions have surprisingly low affinity for a sixth ligand. The current results demonstrate that this effect becomes much less pronounced moving down the periodic table. Attributed to the stronger Lewis acidity of 4d and especially 5d metal ions, such that coordination of a sixth σ-donating ligand becomes much more favorable moving down the group.

Surprisingly, the redox potentials show very little variation among the three corroles, while electron paramagnetic resonance results suggest a shift from corrole- to metal-centered oxidation in moving from 3d and 4d to 5d complexes. For example, the electrochemical data indicated that the metal, rather than the macrocycle, is oxidized only in the case of Ir(III/IV), which contrasts with the most recent findings for analogous cobalt (III) corroles.

Similarly, differences can be seen between the metallocorroles disclosed herein and their metalloporphyrin analogues. For example, the planar macrocyclic framework in both 1-tma and 2-Ir(tma)$_2$ is quite unlike that in the case of porphyrins, which tend to saddle or ruffle when brominated. Similarly, the main structural features of 1-Ir(py)$_2$ are: a very planar macrocyclic framework with a root-mean-square atomic deviation of 0.04 Å out of the plane defined by the N4 coordination core; an in-plane metal ion; and two essentially parallel pyridine rings.

The Ir(III) corroles disclosed herein exhibit long-lived phosphorescence at room temperature, which is very rare for metallocorroles. Moreover, the emission is in the near-infrared (near-IR) range and is readily tuned by the axial ligands and β-pyrrole substituents. Ir(III) corroles phosphoresce in the near infrared at ambient temperatures with lifetimes that are shorter than those of other Ir(III) phosphors. These new compounds may be used for PDT and other medicinal purposes and for development as whole animal imaging agents as well as components of oxygen sensors and OLEDs.

According to embodiments of the present invention, a metallocorrole of Formula I may be synthesized by reacting $H_3$tpfc with excess [M(cod)Cl$_2$] (wherein M is a third row transition metal and cod is cyclooctadiene) and $K_2CO_3$ in hot tetrahydrofuran (THF) under argon ("Ar") to form (tpfc)M(cod), which may be converted to an axially tma-ligated Ir(III) complex upon addition of tma N-oxide and exposure to the atmosphere.

In one exemplary embodiment, the synthesis of 5,10,15-tris-pentafluorophenylcorrole ("$H_3$tpfc") may be accomplished by a modified version of the standard procedure outlined in "Solvent-Free Condensation of Pyrrole and Pentafluorobenzaldehyde: A Novel Synthetic Pathway to Corrole and Oligopyrromethenes" *Organic Letters.* 1999, 1, 599-602, the entire content of which is incorporated herein by reference. For example, $H_3$tpfc may be synthesized by adding a solution of trifluoroacetic acid in $CH_2Cl_2$ to warm pentafluorobenzaldehyde, with rapid stirring. Freshly distilled pyrrole may be added to form a viscous red solution. $CH_2Cl_2$ may also be added with brief stirring. DDQ may be added slowly to oxidize the macrocycle. The product may be purified by successive chromatographic treatments with $CH_2Cl_2$:hexanes on silica, and recrystallization from hot pentane.

According to embodiments of the present invention, a metallocorrole of Formula II may be synthesized by suspending an excess of M(cod)Cl$_2$ (wherein M is a third row transition metal and cod is cyclooctadiene) and $K_2CO_3$ in THF under argon. The suspension may be reacted with $H_3$tpfc heating at reflux until no more red fluorescence is detected. The solution may be evaporated, and the residue may be taken up in $CH_2Cl_2$. Column chromatographic separation in hexanes/$CH_2Cl_2$ may provide solution from which the metallocorrole may be recovered by. An example of such a synthesis is illustrated in Scheme 7 below.

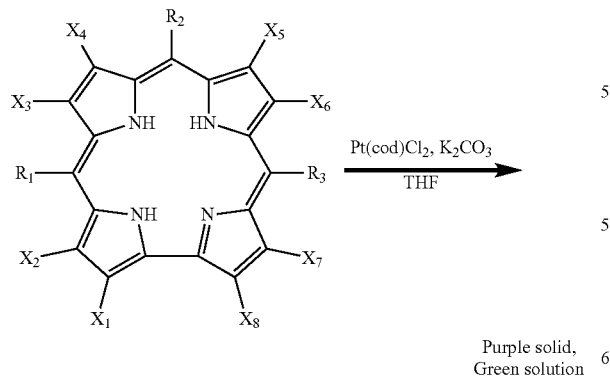

(Scheme 7)

Purple solid, Green solution

According to one embodiment, a metallocorrole complex including tungsten ("W") could be synthesized. In such a synthesis, an excess of W(1,5-cod)(CO)$_4$ and $K_2CO_3$ could be suspended in THF under argon, and $H_3$tpfc could be added. The reaction mixture could be heated at reflux until no more red fluorescence could be detected. The mixture could then be opened to air, and pyridine could be added. After 1 hour, the mixture could be evaporated, and the residue could be taken up in $CH_2Cl_2$. Column chromatographic separation in hexanes/$CH_2Cl_2$ could provide a solution from which (tpfc)W(py)$_2$ could be recovered by evaporation. Based on the behavior of tungsten and osmium in porphyrin complexes, we propose that these metallocorroles might form oxo complexes when exposed to oxygen under certain conditions.

According to another embodiment, a metallocorrole complex including osmium ("Os") could be synthesized. In such a synthesis, an excess of OsCl$_3$ and $K_2CO_3$ could be suspended in THF under argon, and $H_3$tpfc could be added. The reaction mixture could be heated at reflux until no more red fluorescence could be detected. The mixture could then be opened to air, and pyridine could be added. The mixture could then be evaporated, and the residue could be taken up in $CH_2Cl_2$. Column chromatographic separation in hexanes/$CH_2Cl_2$ could provide a solution from which (tpfc)Os(py)$_2$ could be recovered by evaporation.

The following examples are presented for illustrative purposes only and do not limit the scope of the present invention.

Silica gel for column chromatography (Silica Gel 60, 63-200 micron mesh) was purchased from EMD Chemicals. Solvents, such as THF, toluene, $CH_2Cl_2$, hexanes, and methanol, were purchased from EMD Chemicals or the VWR stockroom at the California Institute of Technology. Most starting materials for syntheses were purchased from Sigma-Aldrich and used without further purification. Exceptions include pyrrole and pentafluorobenzaldehyde, which were both purified by vacuum distillation before use. Tetrabutylammonium hexafluorophosphate, which was used as a supporting electrolyte in the CV experiments, was also purchased from Sigma-Aldrich and used without further purification. Electrodes for CV were purchased from CH Instruments.

The synthesis of 5,10,15-tris-pentafluorophenylcorrole ("$H_3$tpfc") was accomplished by a modified version of the standard procedure outlined in "Solvent-Free Condensation of Pyrrole and Pentafluorobenzaldehyde: A Novel Synthetic Pathway to Corrole and Oligopyrromethenes" *Organic Letters.* 1999, 1, 599-602, the entire content of which is incorporated herein by reference. The cobalt(III) and rhodium(III) corroles were available from previous studies. Compounds 1-Ir(tma)$_2$ and 1b-Ir(tma)$_2$ have only been reported in a previous communication, hence their syntheses are summarized below along with those of the new corroles. According to one embodiment, $H_3$tpfc was synthesized by the following route. 140 μL of a solution of 0.5 mL of trifluoroacetic acid in 5 mL of $CH_2Cl_2$ was added to 1.73 mL of warm (liquid) pentafluorobenzaldehyde, with rapid stirring. Addition of 1.46 mL of freshly distilled pyrrole resulted in the rapid formation of a viscous red solution. After 10 minutes, 20 mL of $CH_2Cl_2$ was added and the mixture was allowed to stir briefly, followed by slow addition of 3.84 g of DDQ to oxidize the newly formed macrocycle. Purification was accomplished by successive chromatographic treatments with 6.5:3.5 $CH_2Cl_2$:hexanes and 8.5:1.5 $CH_2Cl_2$:hexanes on silica, followed by recrystallization from hot pentane.

EXAMPLE 1

5,10,15-tris-pentafluorophenylcorrolato-iridium(III) bis-trimethylamine, ("1-Ir(tma)$_2$")

1-Ir(tma)$_2$ was obtained in 27% yield via reaction of $H_3$tpfc with excess [Ir(cod)Cl$_2$] (cod=cyclooctadiene) and $K_2CO_3$ in hot tetrahydrofuran (THF) under argon ("Ar") to form (tpfc)Ir(I)(cod), which was converted to an axially tma-ligated Ir(III) complex upon addition of tma N-oxide and exposure to the atmosphere. $H_3$tpfc (80 mg), [Ir(cod)Cl]$_2$ (335 mg), and $K_2CO_3$ (140 mg) were dissolved/suspended in 150 mL of degassed THF, and the mixture was heated at reflux under argon for 90 min (until corrole fluorescence was negligible to the eye upon long-wave irradiation with a hand-held lamp). Tma N-oxide (110 mg) was added, and the solution was allowed to slowly cool to room temperature while open to the laboratory atmosphere. Column chromatography of the black mixture (silica, 4:1 hexanes:$CH_2Cl_2$) provided an auburn solution, from which purple crystals of (tpfc)Ir(III)(tma)$_2$ (30 mg, 27% yield) could be grown by slow evaporation. $^1$H NMR (CDCl$_3$): δ 8.90 (d, 2H, J=4.2), 8.50 (d, 2H, J=5.1), 8.38 (d, 2H, J=4.5), 8.09 (d, 2H, J=4.2), −2.95 (s, 18H). $^{19}$F NMR (CDCl$_3$): δ −138.38 (m, 6F), −154.89 (m, 3F), −163.27 (m, 6F). MS (ESI): 1105.1 ([M$^+$]), 1046.0 ([M$^+$-tma]), 986.5 ([M$^+$-2tma]). UV-vis (CH$_2$Cl$_2$, nm, ∈×10$^{-3}$M$^{-1}$ cm$^{-1}$): 388 (47), 412 (56), 572 (14), 640 (5.3).

EXAMPLE 2

2,3,7,8,12,13,17,18-octabromo-5,10,15-tris-pentafluorophenylcorrolato-iridium(III)bis-trimethylamine, ("1b-Ir(tma)$_2$")

Compound I-Ir(tma)$_2$ (15 mg) and Br$_2$ (70 μL) were dissolved in 20 mL MeOH and stirred overnight. Column chromatography (silica, 4:1 hexanes:$CH_2Cl_2$) of the red mixture provided a ruddy solution from which purple crystals of 1b-Ir(tma)$_2$ (15 mg, 63% yield) could be grown by addition of methanol followed by slow evaporation. $^1$H NMR (CDCl$_3$): δ −2.60 (s, 18H). $^{19}$F NMR (CDCl$_3$): δ −137.78 (d/d, 2F, $^3$J=35.1, $^4$J=18.3), −138.54 (d/d, 4F, $^3$J=33.9, $^4$J=17.1), −152.89 (m, 3F), −163.38 (m, 4F), −163.70 (m, 2F). MS (ESI): 1616.4 ([M$^+$-2tma]). UV-vis (CH$_2$Cl$_2$, nm, ∈×10$^{-3}$ M$^{-1}$ cm$^{-1}$): 404 (61), 424 (70), 580 (16), 654 (7.3).

As would be understood, although bromination is described, other halogenated corrole macrocycles can be accessed via literature methods.

EXAMPLE 3

5,10,15-tris-pentafluorophenylcorrolato-iridium(III) bis-pyridine, ("1-Ir(py)$_2$")

$H_3$tpfc (40 mg), [Ir(cod)Cl]$_2$ (170 mg), and $K_2CO_3$ (70 mg) were dissolved/suspended in 75 mL of degassed THF, and the mixture was heated at reflux under argon for 90 min. Pyridine (1 mL) was added, and the solution was allowed to slowly cool to room temperature while open to the laboratory atmosphere. Column chromatography of the forest green mixture (silica, 4:1 hexanes:$CH_2Cl_2$ followed by 3:2 hexanes:$CH_2Cl_2$) provided a bright green solution, from which thin, green crystals of 1-Ir(py)$_2$ (26 mg, 50% yield) could be grown by addition of methanol followed by slow evaporation. $^1$H NMR (CDCl$_3$): δ 8.84 (d, 2H, J=4.5), 8.53 (d, 2H, J=4.8), 8.32 (d, 2H, J=4.8), 8.17 (d, 2H, J=4.5), 6.21 (t, 2H, J=7.8), 5.19 (t, 4H, J=7.0), 1.72 (d, 4H, J=5.1). $^{19}$F NMR (CDCl$_3$): δ −138.68 (m, 6F), −154.84 (t, 2F, J=22.2), −155.20 (t, 1F, J=22.2), −163.28 (m, 4F), −163.65 (m, 2F). MS (ESI): 1144.1 ([M$^+$]). UV-vis (CH$_2$Cl$_2$, nm, ∈×10$^{-3}$M$^{-1}$ cm$^{-1}$): 390 (28), 412 (43), 582 (12), 619 (6.5).

EXAMPLE 4

5,10,15-tris-pentafluorophenylcorrolato-iridium(III) triphenylphosphine, ("1-Ir(PPh$_3$)")

$H_3$tpfc (40 mg), [Ir(cod)Cl]$_2$ (170 mg), and $K_2CO_3$ (70 mg) were dissolved/suspended in 75 mL of degassed THF, and the mixture was heated at reflux under argon for 90 min. Triphenylphosphine (260 mg dissolved in 5 mL THF) was added, and the solution was heated at reflux for another half hour under laboratory atmosphere before being allowed to cool to room temperature. Column chromatography of the deep green mixture (silica, 3:1 hexanes:$CH_2Cl_2$) provided a bright red-orange solution, which could be evaporated to give 1-Ir (PPh$_3$) (30 mg, 64% yield) as a ruby-colored solid. $^1$H NMR (CDCl$_3$): δ 8.67 (d, 2H, J=4.5), 8.36 (d, 2H, J=5.1), 8.18 (d, 2H, J=5.1), 8.00 (d, 2H, J=4.5), 6.98 (t, 3H, J=7.2), 6.69 (t, 6H, J=6.9), 4.52 (d/d, 6H, $^3$J=19.5, $^4$J=3.6). $^{19}$F NMR (CDCl$_3$): δ −137.44 (m, 6F), −154.05 (m, 3F), −162.54 (m, 3F). MS (ESI): 1248.1 ([M$^+$]). UV-vis (CH$_2$Cl$_2$, nm, ∈×10$^{-3}$ M$^{-1}$ cm$^{-1}$): 398 (66), 554 (8.8), 588 (6.7).

EXAMPLE 5

5,10,15-tris-pentafluorophenylcorrolato-iridium(III) bis-cyanopyridine, ("1-Ir(CNpy)$_2$")

$H_3$tpfc (40 mg), [Ir(cod)Cl]$_2$ (170 mg), and $K_2CO_3$ (70 mg) were dissolved/suspended in 75 mL of degassed THF, and the mixture was heated at reflux under argon for 90 min. 4-Cyanopyridine (105 mg) was added, and the solution was allowed to slowly cool to room temperature while open to the laboratory atmosphere. Column chromatography of the red-green mixture (silica, 4:1 hexanes:$CH_2Cl_2$ followed by 2:3 hexanes:$CH_2Cl_2$) provided a bright red solution, which upon evaporation provided 1-Ir(CNpy)$_2$ (36 mg, 66% yield) as a purple solid. $^1$H NMR (CDCl$_3$): δ 8.91 (d, 2H, J=4.5), 8.60 (d, 2H, J=5.1), 8.39 (d, 2H, J=4.8), 8.26 (d, 2H, J=4.5), 5.43 (d/d, 4H, $^3$J=6.9, $^4$J=−4.2), 1.75 (d/d, 4H, $^3$J=6.9, $^4$J=−3.9). $^{19}$F NMR (CDCl$_3$): δ −138.38 (d/d, 2F, $^3$J=34.8, $^4$J=17.4), −138.95 (d/d, 4F, $^3$J=34.8, $^4$J=17.4), −153.75 (t, 2F, J=22.5), −154.11 (t, 1F, J=22.2), −162.48 (m, 4F). −162.84 (m, 2F). MS (ESI): 1089.0 ([M$^+$-4-CNpy]), 986.1 ([M$^+$-2(4-CNpy)]) UV-vis (CH$_2$Cl$_2$, nm, ∈×10$^{-3}$ M$^{-1}$ cm$^{-1}$): 388 (8.8), 406 (14), 580 (4.2), 608 (2.8).

EXAMPLE 6

5,10,15-tris-pentafluorophenylcorrolato-iridium(III) bis-4-methoxypyridine, ("1-Ir(MeOpy)$_2$")

$H_3$tpfc (40 mg), [Ir(cod)Cl]$_2$ (170 mg), and $K_2CO_3$ (70 mg) were dissolved/suspended in 75 mL of degassed THF, and the mixture was heated at reflux under argon for 90 min 4-Methoxypyridine (110 mg) was added, and the solution was allowed to slowly cool to room temperature while open to the laboratory atmosphere. Column chromatography of the red-green mixture (silica, 4:1 hexanes:$CH_2Cl_2$ followed by 2:3 hexanes:$CH_2Cl_2$) provided an olive solution, which upon evaporation provided 1-Ir(MeOpy)$_2$ (28 mg, 50% yield) as a dark green solid. $^1$H NMR (CDCl$_3$): δ 8.81 (d, 2H, J=4.2), 8.49 (d, 2H, J=4.5), 8.31 (d, 2H, J=4.5), 8.12 (d, 2H, J=3.9), 4.69 (d/d, 4H, $^3$J=7.2, $^4$J=−4.5), 2.93 (s, 6H), 1.56 (m, 4H). $^{19}$F NMR (CDCl$_3$): δ −138.40 (d/d, 2F, $^3$J=35.7, $^4$J=17.4), −138.64 (d/d, 4F, $^3$J=35.7, $^4$J=17.4), −154.98 (t, 2F, J=22.5), −155.35 (t, 1F, J=22.4), −163.33 (m, 4F). −163.69 (m, 2F). UV-vis (CH$_2$Cl$_2$, nm, ∈×10$^{-3}$M$^{-1}$ cm$^{-1}$): 394 (42), 412 (57), 394 (42), 412 (57).

EXAMPLE 7

5,10,15-tris-pentafluorophenylcorrolato-iridium(III) bis[3,5-bis(trifluoromethyl)pyridine], ["1-Ir((CF$_3$)$_2$py)$_2$"]

H$_3$tpfc (40 mg), [Ir(cod)Cl]$_2$ (170 mg), and K$_2$CO$_3$ (70 mg) were dissolved/suspended in 75 mL of degassed THF, and the mixture was heated at reflux under argon for 90 min. 3,5-bis-trifluoromethylpyridine (215 mg) was added, and the solution was allowed to slowly cool to room temperature while open to the laboratory atmosphere. Column chromatography of the deep green mixture (silica, 4:1 hexanes:CH$_2$Cl$_2$ followed by 100% CH$_2$Cl$_2$) provided a red-green solution, which upon evaporation provided 1-Ir((CF$_3$)$_2$py)$_2$ (13 mg, 20% yield) as a filmy red-purple solid. $^1$H NMR (CDCl$_3$): δ 9.00 (d, 2H, J=4.2), 8.70 (d, 2H, J=4.8), 8.44 (d, 2H, J=4.8), 8.38 (d, 2H, J=4.2), 6.65 (s, 2H), 1.97 (s, 4H). $^{19}$F NMR (CDCl$_3$): δ=−64.29 (t, 12F, J=7.5), −138.47 (m, 6F), −153.52 (t, 2F, J=22.2), −153.82 (m, 1F), −162.35 (m, 6F). UV-vis (CH$_2$Cl$_2$, nm, ∈×10$^{-3}$M$^{-1}$ cm$^{-1}$): 384 (9.7), 406 (15), 580 (4.5), 602 (2.8).

EXAMPLE 8

5,10,15-tris-pentafluorophenylcorrolato-iridium(III) bis(3,5-dichloropyridine], ["1-Ir(Cl$_2$py)$_2$"]

H$_3$tpfc (40 mg), [Ir(cod)Cl]$_2$ (170 mg), and K$_2$CO$_3$ (70 mg) were dissolved/suspended in 75 mL of degassed THF, and the mixture was heated at reflux under argon for 90 min. 3,5-dichloropyridine (150 mg) was added, and the solution was allowed to slowly cool to room temperature while open to the laboratory atmosphere. Column chromatography of the bright green mixture (silica, 4:1 hexanes:CH$_2$Cl$_2$ followed by 100% CH$_2$Cl$_2$) provided a vivid green solution, from which dark green crystals of 1-Ir(Cl$_2$py)$_2$ (27 mg, 47% yield) could be grown by addition of toluene followed by slow evaporation. $^1$H NMR (CDCl$_3$): δ 8.91 (d, 2H, J=4.2), 8.64 (d, 2H, J=4.5), 8.40 (d; 2H, J=4.5), 8.30 (d, 2H, J=4.2), 6.16 (t, 2H, J=1.8), 1.52 (d, 4H, J=1.8). $^{19}$F NMR (CDCl$_3$): δ −137.49 (d/d, 2F, $^3$J=34.8, $^4$J=17.7), −137.71 (d/d, 4F, $^3$J=34.8, $^4$J=17.1), −153.87 (t, 2F, J=22.5), −154.28 (t, 1F, J=22.2), −162.39 (m, 4F). −162.82 (m, 2F). UV-vis (CH$_2$Cl$_2$, nm, ∈×10$^{-3}$M$^{-1}$ cm$^{-1}$): 390 (26), 406 (38), 580 (12), 608 (7.3).

Nuclear Magnetic Resonance Spectroscopy ("NMR"): $^1$H and $^{19}$F NMR spectrometric measurements were performed on CDCl$_3$ solutions of each compound at room temperature using a Varian Mercury 300 MHz NMR spectrometer. $^1$H chemical shifts are reported relative to solvent peaks and $^{19}$F chemical shifts are reported relative to a saved, external CFCl$_3$ standard.

Mass Spectrometry: Mass spectrometric measurements were performed on CH$_3$OH solutions of each compound by electrospray ionization into a Thermofinnigan LCQ ion trap mass spectrometer.

X-Ray Crystallography: Concentrated CH$_2$Cl$_2$/CH$_3$OH solutions of corroles 1-Ir(tma)$_2$, 1b-Ir(tma)$_2$, and 1-Ir(py)$_2$ were allowed to undergo slow evaporation from scintillation vials. The resultant crystals were mounted on a glass fiber using Paratone oil and then placed on a Bruker Kappa Apex II diffractometer under a nitrogen stream at 100 K. The SHELXS-97 program was used to solve the structures.

Cyclic Voltammetry: Cyclic voltammetry ("CV") was carried out with a WaveNow USB Potentiostat/Galvanostat (offered by Pine Research Instrumentation) using Pine Aftermath Data Organizer software. A three electrode system were used and consisted of platinum wire working electrode, a platinum wire counter electrode, and an Ag/AgCl reference electrode. The CV measurements were done at ambient temperature and under argon atmosphere using dichloromethane solutions, 0.1 M in tetrabutylammonium perchlorate (TBAP, Fluka, recrystallized twice from absolute ethanol) and 10$^{-3}$ M in substrate. The scan rate was 100 mV/sec and the E$_{1/2}$ value for oxidation of ferrocene under these conditions was 0.55 V.

Cyclic voltammetry ("CV", FIG. 4) reveals that Ir(III) corroles are very electron-rich: Ir(II) is not electrochemically accessible and Ir(IV) is obtained at relatively low potentials. These particular CV measurements were made in degassed CH$_2$Cl$_2$ solutions under Ar containing 0.3 M NEt$_4$BF$_4$, using a glassy carbon disk working electrode, a Pt wire auxiliary electrode, and a Ag/AgCl quasi-reference electrode. Only 2 could be reduced within the electrochemical window of the solvent and the reversibility of that process (E$_{1/2}$=−1.21V vs. SCE) is consistent with the formation of a corrole radical anion rather than Ir(II), as the latter would rapidly release its axial ligand(s) and most likely also dimerize. All other reversible electron transfer processes are also obtained at quite positive potentials. Guided by the electrochemistry of other metallocorroles, the first and second redox processes of 1 (E$_{1/2}$=+0.66 and +1.28 V vs. SCE, respectively) may tentatively be assigned as metal-centered (Ir$^{III}$/Ir$^{IV}$) and corrole-centered (tpfc/tpfc$^+$), respectively. As full bromination at the β-pyrrole positions is known to upshift the potentials of metallocorroles by a few hundred mV, the feature at +1.19 V can be assigned to the Ir$^{III}$/Ir$^{IV}$ couple in 2. Our data show clearly that Ir(III) is more electron-rich in corroles than in other coordination environments. The E$_{1/2}$ value for the [(tpp)Ir]$^+$/[(tpp)Ir]$^{2+}$ (tpp=tetraphenylporphyrinato) redox couple is about +1.4 V vs. SCE, and Ir$^{III}$/Ir$^{IV}$ processes in cyclometalated bpy complexes also occur at much more positive potentials than in 1.

Electron Paramagnetic Resonance ("EPR"): Solutions for EPR were prepared by adding 25 μL of either a 1 mM CH$_2$Cl$_2$ solution of tris(4-bromophenyl)aminiumhexachloroantimonate ("t-4bpa") or a 1 mM toluene solution of elemental iodine to 150 μL of a 2 mM toluene solution of the corrole being examined. EPR spectroscopy was performed using a Bruker EMX Biospin instrument, with a Gunn diode microwave source. Solutions were glassed by rapid freezing in liquid nitrogen, and spectra were then taken at 20 K using liquid helium as coolant. The SPINCOUNT package was used to simulate EPR parameters.

UV-vis Absorption Spectroscopy: Electronic absorption measurements were performed on solutions of each compound in CH$_2$Cl$_2$, using a Hewlett-Packard 8452A Diode Array Spectrophotometer. Extinction coefficients were calculated from measurements performed on gravimetrically produced CH$_2$Cl$_2$ solutions of each corrole at variable concentrations. UV-visible spectroelectrochemical experiments were performed with an optically transparent platinum thin-layer electrode as working electrode, a platinum wire counter electrode, and an Ag/AgCl reference electrode, at ambient temperature and under argon atmosphere using dichloromethane solutions, 0.5 M in TBAP and 0.1-0.1 mM in substrate. Potentials were applied with a WaveNow USB Potentiostat/Galvanostat. Time-resolved UV-visible spectra were recorded with a Hewlett-packard Model 8453 diode array rapid-scanning spectrophotometer.

Solution state UV-vis absorption spectra were measured using a Cary 50 scanning spectrophotometer with a pulsed xenon lamp as the excitation source. The error in reported wavelength values is at most 0.5 nm. Extinction coefficients were measured for gravimetrically prepared solutions of iridium corroles in toluene, and should be accurate to ±10%.

Steady-state and time-resolved emission measurements were conducted at the Beckman Institute Laser Resource Center. Emission spectra were recorded on samples dissolved in solution (room temperature) or frozen glass (77 K). Samples were degassed by three freeze-pump-thaw cycles. For steady-state emission spectra, the 496.5 nm line of an argon ion laser (Coherent Inova 70) was used to excite samples. Right angle emission was collected via with a Melles Griot Fiber Optic Spectrometer (MGSPEC-2048-SPU). Quantum yields were obtained by comparing signal intensity to a tetraphenylporphyrin standard. Absorption values for the samples at 496.5 nm were recorded on a Hewlett-Packard 8451A diode array spectrophotometer.

For time-resolved measurements, samples were excited at 440 nm. Pulses of 8 ns duration from the third harmonic of a Q-switched Nd:YAG laser (Spectra-Physics Quanta-Ray PRO-Series) operating at 10 Hz were used to pump an optical parametric oscillator (OPO, Spectra-Physics Quanta-Ray MOPO-700) to provide laser pulses at 440 nm. Emitted light was detected with a photomultiplier tube (PMT, Hamamatsu R928). PMT current was amplified and recorded using a transient digitizer (Tektronix DSA 602).

Excitation spectra were recorded on a Jobin Yvon Spex Fluorolog-3-11. Sample excitation was achieved via a xenon arc lamp with a monochromator providing wavelength selection. The excitation wavelength was scanned between 300 nm and 700 nm and recorded at 790 nm and 890 nm. Slits of 2 and 10 nm bandpass were used for excitation and emission, respectively. Right angle light emission was sorted using a monochromator and fed into a Hamamatsu R928P photomultiplier tube with photon counting. Short and long pass filters were used where appropriate.

Resonance Raman spectra were recorded using the 488 nm line of an argon ion laser (Coherent Inova 70). Scattered light was sorted by a 0.75 m spectrograph (Spex 750M) and detected with a liquid-nitrogen-cooled CCD (Princeton Instruments).

The refraction of the sodium D line at 20° C. in a given solvent was taken to represent its refractive index, $n_D^{20}$, or simply n. The polarizability of a solvent [f(n)] is related to its refractive index via the following relationship: $f(n)=(n^2-1)/(2n^2+1)$ [Lakowicz, Joseph R. *Principles of Fluorescence Spectroscopy*, $2^{nd}$ Ed. 1999, pg. 189]. The extent of the solvatochromic effect exhibited by an absorbing species in a given solvent is then determined by the slope of the line $E_f=E_v-(solv)[f(n)]$, where $E_f$ is the absorption energy in the solvent, $E_v$ is the absorption energy in vacuum, and (solv) is a factor related to the magnitude of the change in the dipole moment of the chromophore upon excitation. In this formalism, the y-intercept of the line is equal to the theoretical gas-phase absorption energy of the transition under examination. We have made our solvatochromism plots by setting this value equal to zero and plotting the extent of red-shifting in a variety of solvents. This allows for facile comparison of the three corroles, such that the steepness of the slope scales with the magnitude of the separation between the ground and excited state dipole moments. In all cases, the excited state is more polar than the ground state.

A stable six-coordinate (tpfc)Ir(tma)$_2$ complex (1-Ir(tma)$_2$, Scheme 1) was obtained as described above. As described above, an octabrominated complex ((Br$_8$-tpfc)Ir(tma)$_2$ (1b-Ir(tma)$_2$, Scheme 1) was obtained from 1-Ir(tma)$_2$. Both iridium(III) derivatives were characterized by nuclear magnetic resonance (NMR) spectroscopy, mass spectrometry (MS), X-ray crystallography, UV-vis spectroscopy, and cyclic voltammetry (CV). The planar macrocyclic framework in both 1-Ir(tma)$_2$ and 1b-Ir(tma)$_2$ is quite unlike that in the case of porphyrins, which tend to saddle or ruffle when brominated. In addition, the electrochemical data indicated that the metal, rather than the macrocycle, is oxidized to Ir(IV) in both complexes, which contrasts with most recent findings for analogous cobalt(III) corroles.

Figure 13:
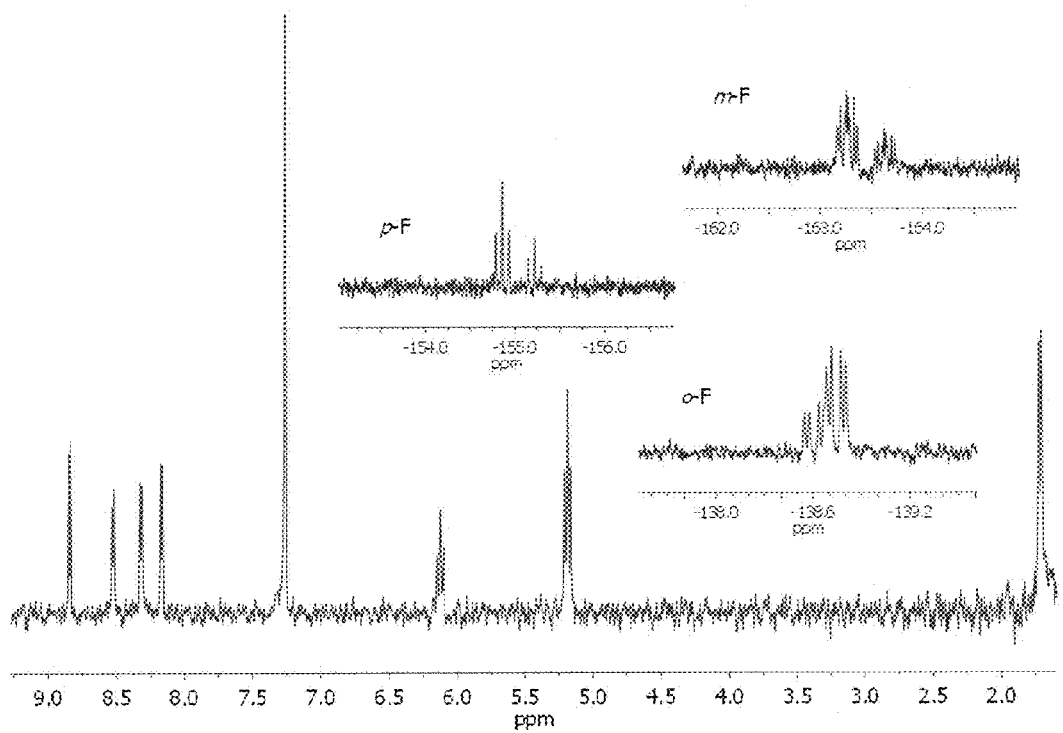
FIG. 13 is a graph of a $^1$H NMR spectrum (red) and a graph of a $^{19}$F NMR spectra (blue inserts) of 1-Ir(py)$_2$.

Owing to their low-spin $d^6$ electronic configuration, iridium(III) corroles display highly resolved NMR spectra characteristic of diamagnetic complexes. This is shown in FIG. 13 for 1-Ir(py)$_2$, where the $^1$H NMR spectra disclose the four β-pyrrole CH proton resonances as doublets with J coupling constants of about 4.5 Hz at 8-9 ppm and the axial ligand resonances at high field due to the diamagnetic ring current effect of the aromatic corrole. The pyridine proton resonances for 1-Ir(py)$_2$ are more shifted than those of the PPh$_3$ moiety in Ir(PPh$_3$) (both relative to their position in the absence of a metal center) due to the much closer proximity of these former protons to the corrole ring. The coordination number (6 for the bis-pyridine complex 1-Ir(py)$_2$ and 5 for the triphenylphosphine complex 1-Ir(PPh$_3$)) can be deduced from the $^1$H NMR spectra via integration of the relevant proton resonances. The same information is also accessible from the $^{19}$F NMR spectra (FIG. 13, inset), since the $C_{2v}$ symmetry of 1-Ir(py)$_2$ dictates an equivalence between the above- and below-plane ortho- and meta-fluorine atoms on each $C_6F_5$ ring, resulting in six total $^{19}$F NMR peaks for the complex.

The red shifts of the principal features in the electronic spectrum of 2 relative to 1 (8-16 nm, FIG. 3) are similar to those observed upon bromination of other metallocorroles, but the intense Soret band system is uniquely split, as are the Q-bands (roughly 70 nm). Without being limited by theory, the shoulders at 448 and 458 nm for 1 and 2, respectively, may be attributable to MLCT transitions, and the couplings to these excited states may give rise to large splittings of the corrole-based π-π* states. Based on HOMO and LUMO energies extracted from the redox potentials of 2, the MLCT transitions should fall in the 400-500 nm region of the visible spectrum.

The molecular structures of 1 and 2 (FIG. 5) reveal that their macrocyclic frameworks are isostructural, with the iridium atom located in the plane of an essentially flat corrole. The Ir—N axial bonds are about 0.2 Å longer than the in-plane Ir—N equatorial bonds, as might be expected. One notable difference between 1 and 2 is that the aryl rings are nearly perpendicular with respect to the corrole in the latter, possibly to avoid steric clash with the bromine atoms. The structure of 2 is distinctly different from those of analogous tetraarylporphyrins, where β-pyrrole bromination induces large distortions of the macrocycle that produce dramatic red shifts in UV-vis absorptions and higher reduction potentials. For iridium corroles, the 530 mV upshift in the potential of 2 vs. 1 may imply major Br-induced electronic effects.

Figure 6:
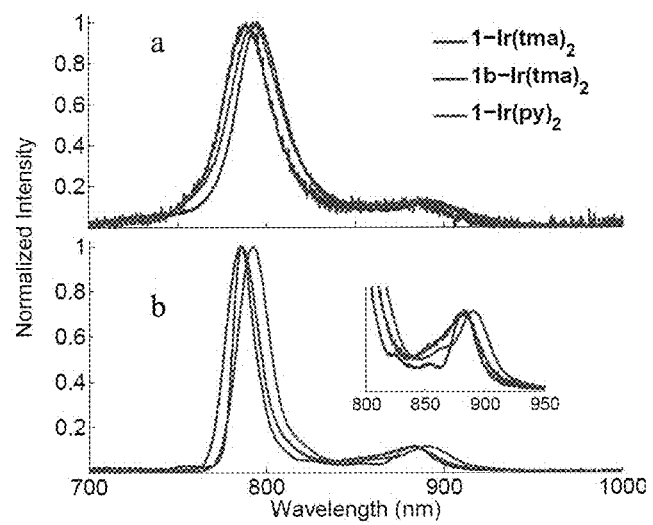
FIG. 6 is a graph of emission spectra of Ir(III) corroles in degassed toluene solution $\lambda_{ex}$–496.5 nm); a. was measured at 298 K; b. was measured at 77 K.

Emission spectra were recorded in toluene at 298 and 77 K (FIG. 6). The spectra display two intense features separated by approximately 1400 cm$^{-1}$. It is likely that a ring-based vibration is excited in the transition to the lower energy component.

According to embodiments of the present invention, a corrole can readily accommodate a 5d transition metal. The electron transfer processes demonstrated for 1 and 2 suggest that they may prove useful as redox catalysts.

At low temperature, the higher energy emission maximum of each Ir(III) corrole blue shifts by 10 nm (a rigidochromic effect indicating that the transition involves charge transfer) (FIG. 6b). The narrow linewidth and ~1400 cm$^{-1}$ spacing suggest that the emission is from a π→π* excited state. Electronic structure calculations place an occupied orbital with metal character close to the HOMO in related Ir(III) corroles, indicating that $^3$MLCT states will be near those of the lowest corrole-localized excited states. The $^3$MLCT state may also be the emissive state in other cyclometalated Ir(III) complexes.

Luminescence quantum yields and lifetimes in degassed and aerated toluene solutions at room temperature (and lifetimes at 77 K) are set out in Table 1. 1-Ir(tma)$_2$ and 1b-Ir(tma)$_2$ have relatively short lifetimes and low quantum yields. 1-Ir(py)$_2$ exhibits a much higher luminescence quantum yield (1.2%) and a longer lifetime. These results indicate that Ir(III)-corrole photophysical properties may depend on the nature of the axial ligand.

TABLE 1

Photophysical data for Ir(III) corroles in toluene solutions, measured at 298 K unless noted otherwise.

| Compound | 1-Ir(tma)$_2$ | 1b-Ir(tma)$_2$ | 1-Ir(py)$_2$ |
|---|---|---|---|
| $\Phi_{ph}{}^b$ | 3.3 × 10$^{-4}$ | 3.9 × 10$^{-3}$ | 1.2 × 10$^{-2}$ |
| $\lambda_{Ar}$(nm)/$\tau_{Ar}$ (μs) | 788/0.220 | 795/1.19 | 792/4.91 |
| $\tau_{air}{}^c$ (μs) | 0.170 | 0.760 | 0.380 |
| $\lambda_{77K}$(nm)/$\tau_{Ar}$ (μs) | 786/2.77 | 786/4.72 | 793/7.69 |
| $k_r$ (s$^{-1}$) | 1.5 × 10$^3$ | 3.28 × 10$^3$ | 2.44 × 10$^3$ |
| $k_{nr}$ (s$^{-1}$) | 4.54 × 10$^6$ | 8.4 × 10$^5$ | 2.0 × 10$^5$ |

$^b$Luminescence quantum yields were standardized against free-base tetraphenylporphyrin ($\Phi_f$ = 0.13 in toluene solution at 298 K).
$^c$Measured under atmospheric conditions.

UV-vis absorption spectra (FIG. 7) of the three Ir(III) corroles exhibit split Soret (S$_0$→S$_2$) and Q (S$_0$→S$_1$) bands. The splitting of the Soret bands is 1400-1700 cm$^{-1}$ in all cases; the Q bands are split by roughly 1800 cm$^{-1}$ in the spectra of 1-Ir(tma)$_2$ and 1b-Ir(tma)$_2$ but only by 1000 cm$^{-1}$ in the spectrum of 1-Ir(py)$_2$.

The effect of solvent polarizability on Ir(III)-corrole spectra was investigated to probe the extent of charge transfer in initially formed electronic excited states. UV-vis spectra were obtained in a variety of solvents: Soret band maxima were plotted against polarizability f (FIG. 8), defined as f(n)=(n$^2$−1)/(2n$^2$+1), where n is the refractive index of the solvent. (The ground states are relatively nonpolar, so inclusion of a solvent dielectric term is not appropriate.) The strong negative correlation (R$^2$>0.9) between the polarizability of the solvent and the energy of the Soret transition indicates that in each case the excited state is substantially more polar than the ground state. The Q band maxima display a similar trend. The striking solvatochromic behavior of Ir(III) corroles may be exploited in optical sensors as well as other applications requiring solvent-based tuning of absorption and emission properties.

Although the Soret solvatochromic shifts of 1-Ir(tma)$_2$ and 1-Ir(py)$_2$ are similar, 1b-Ir(tma)$_2$ exhibits a somewhat weaker trend. Without being limited by theory, this trend may be attributable to bromine atom "prepolarization" of the electron density on the corrole, thereby decreasing the change in dipole moment upon excitation. Alternatively, the observed trend may result from differences in the polarity of the excited state initially formed by each of the compounds.

According to embodiments of the present invention, Ir(III) corroles phosphoresce in the near infrared region at ambient temperatures with lifetimes and quantum yields that may depend on the nature of the axial ligands. According to the emission band shapes and vibronic splittings taken together with results from electronic structure calculations, the phosphorescence of the compounds according to the present invention may be attributable to a transition from a corrole π→π* triplet state that likely has some $^3$MLCT character.

TABLE 2

Slopes and fitting values for solvatochromic effects on each absorption band in the iridium(III) corroles; the correlation values for the Q bands of 1b-Ir(tma)$_2$ are probably poor due to the low intensities of those bands at the concentrations examined.

| Comound | Band | Slope of Shift (f/cm$^{-1}$) | Correlation R$^2$ |
|---|---|---|---|
| 1-Ir(tma)$_2$ | First Soret | −3200 | 0.90 |
| | Second Soret | −4600 | 0.90 |
| | First Q band | −2100 | 0.77 |
| | Second Q band | −1800 | 0.91 |
| 1b-Ir(tma)$_2$ | First Soret | −2500 | 0.78 |
| | Second Soret | −2900 | 0.95 |
| | First Q band | −1000 | 0.60 |
| | Second Q band | −850 | 0.25 |
| 1-Ir(py)$_2$ | First Soret | −4300 | 0.90 |
| | Second Soret | −5000 | 0.94 |
| | First Q band | −2100 | 0.75 |
| | Second Q band | −2000 | 0.89 |

TABLE 3

Luminescence lifetimes of Ir(III) corroles in methanol at 298 K; this illustrates that a non-polar solvent such as toluene is not required by any means to achieve luminescence in our systems.

| Compound | $\tau_{Ar}$ (μs) [77 K] |
|---|---|
| 1-Ir(tma)$_2$ | 0.103 [2.82] |
| 1b-Ir(tma)$_2$ | 0.668 [3.95 |
| 1-Ir(py)$_2$ | 0.470 [7.57] |

TABLE 4

Refractive indices (nD$^{20}$), solvent polarizabilities [f(n)], and Ir(III) corrole absorbance maxima (in cm$^{-1}$) of the solvents used in our solvatochromic experiments (py = 1-Ir(py)$_2$, br = 1b-Ir(tma)$_2$, tm = 1-Ir(tma)$_2$; S1 and S2 = blue and red Soret bands, respectively; Q1 and Q2 = blue and red Q bands, respectively).

| Solvent | $n_D{}^{20}$ | f(n) | pyS1 | pyS2 | pyQ1 | pyQ2 | brS1 |
|---|---|---|---|---|---|---|---|
| MeOH | 1.33 | 0.169 | 25674 | 24528 | 17244 | 16202 | 24894 |
| CH3CN | 1.34 | 0.173 | 25720 | 24528 | 17253 | 16250 | 24839 |
| Acetone | 1.36 | 0.181 | 25674 | 24492 | 17227 | 16202 | 24808 |
| Ethanol | 1.36 | 0.181 | 25634 | 24474 | 17227 | 16194 | 24857 |
| Hexanes | 1.37 | 0.184 | 25654 | 24528 | 17215 | 16250 | 24894 |

TABLE 4-continued

Refractive indices ($nD^{20}$), solvent polarizabilities [f(n)], and Ir(III) corrole absorbance maxima (in $cm^{-1}$) of the solvents used in our solvatochromic experiments (py = 1-Ir(py)$_2$, br = 1b-Ir(tma)$_2$, tm = 1-Ir(tma)$_2$; S1 and S2 = blue and red Soret bands, respectively; Q1 and Q2 = blue and red Q bands, respectively).

| | | | | | | | |
|---|---|---|---|---|---|---|---|
| THF | 1.41 | 0.199 | 25562 | 24390 | 17197 | 16160 | 24789 |
| DCM | 1.42 | 0.202 | 25523 | 24355 | 17147 | 16168 | 24759 |
| DMF | 1.43 | 0.205 | 25582 | 24390 | 17215 | 16179 | 24734 |
| CHCl3 | 1.45 | 0.212 | 25465 | 24301 | 17112 | 16124 | 24734 |
| CCl4 | 1.46 | 0.215 | 25465 | 24278 | 17109 | 16145 | 24808 |
| Benzene | 1.5 | 0.227 | 25465 | 24254 | 17138 | 16098 | 24734 |
| Toluene | 1.5 | 0.227 | 25465 | 24278 | 17138 | 16108 | 24734 |
| Pyridine | 1.51 | 0.23 | 25465 | 24254 | 17147 | 16108 | 24697 |

| Solvent | brS2 | brQ1 | brQ2 | tmS1 | tmS2 | tmQ1 | tmQ2 |
|---|---|---|---|---|---|---|---|
| MeOH | 23747 | 17235 | 15305 | 25760 | 24438 | 17535 | 15723 |
| CH3CN | 23702 | 17235 | 15256 | 25786 | 24390 | 17516 | 15708 |
| Acetone | 23685 | 17227 | 15242 | 25760 | 24390 | 17516 | 15708 |
| Ethanol | 23702 | 17227 | 15316 | 25740 | 24390 | 17516 | 15723 |
| Hexanes | 23764 | 17253 | 15434 | 25813 | 24450 | 17516 | 15765 |
| THF | 23652 | 17179 | 15218 | 25674 | 24301 | 17492 | 15669 |
| DCM | 23635 | 17188 | 15279 | 25654 | 24254 | 17434 | 15657 |
| DMF | 23618 | 17188 | 15218 | 25674 | 24301 | 17492 | 15669 |
| CHCl3 | 23635 | 17188 | 15309 | 25615 | 24201 | 17416 | 15642 |
| CCl4 | 23618 | 17206 | 15366 | 25634 | 24143 | 17391 | 15635 |
| Benzene | 23557 | 17164 | 15232 | 25615 | 24184 | 17416 | 15610 |
| Toluene | 23557 | 17164 | 15232 | 25634 | 24201 | 17434 | 15635 |
| Pyridine | 23540 | 17209 | 15218 | 25543 | 24160 | 17434 | 15603 |

According to embodiments of the present invention, axially ligated five- and six-coordinate iridium(III) corroles have been synthesized and fully characterized. Further, the isostructural Group 9 metallocorroles (1-M(PPh$_3$) and 1-M(py)$_2$, where M=cobalt(III), rhodium(III), or iridium(III) and 1 denotes the trianion of 5,10,15-tris-pentafluorophenylcorrole) have been investigated by X-ray crystallography and cyclic voltammetry. Both chemical and electrochemical oxidation products have been characterized by absorption and electronic paramagnetic resonance spectroscopic methods. The average metal-N(pyrrole) bond lengths increase from Co (1.886 Å) to Rh (1.957 Å)/Ir (1.963 Å); and the average metal-N(pyridine) bond lengths also increase from Co (1.995 Å) to Rh (2.065 Å)/Ir (2.059 Å). There is a surprising invariance in the first reduction potentials within the five- and six-coordinate corrole series, and even between them; the average half-wave potential of 1-M(PPh$_3$) is 0.78 V vs. Ag/AgCl in CH$_2$Cl$_2$ solution, whereas that of 1-M(py)$_2$ is 0.70 V under the same conditions. These Group 9 metallocorroles exhibit dramatically different absorption spectral changes upon chemical or electrochemical oxidation in CH$_2$Cl$_2$ solutions, indicating striking differences in electronic structures. Electronic structural variations have been assigned by analysis of EPR spectroscopic measurements on chemically oxidized 1-M(py)$_2$ corroles. The g tensor is isotropic for 1-Co(py)$_2$ (2.006); for 1-Rh(py)$_2$, $g_\parallel$=2.032, $g_\perp$=2.001, $g_{av}$=2.016; for 1-Ir(py)$_2$, $g_{zz}$=2.044, $g_{yy}$=1.993 $g_{xx}$=1.836, $g_{av}$=1.958: oxidation is corrole-centered for 1-Co(py)$_2$; corrole-metal delocalized for 1-Rh(py)$_2$; and primarily metal-centered for 1-Ir(py)$_2$. There also is a clear trend in ligand substitution behavior within the Group 9 metallocorroles: ligand affinities at the 1-M(PPh$_3$) open coordination sites differ by three to four orders of magnitude in the order 1-Co(PPh$_3$)<1-Rh(PPh$_3$)<1-Ir(PPh$_3$).

According to embodiments of the present invention, corroles of 1-Ir(py)$_2$ and 1-Ir(PPh$_3$) have been synthesized and characterized, and their properties have been compared with those of isoelectronic and isostructural cobalt(III) and rhodium(III) analogs 1-Co(py)$_2$, 1-Rh(py)$_2$, 1-Co(PPh$_3$), and 1-Rh(PPh$_3$) (Scheme 5). This series represents quite a rare example of an entire transition metal group of complexes with the same oxidation state and coordination number. Another group that fulfills these conditions is comprised of the (por) M-CO complexes of Group 8 transition metals. The substitutional lability of the Group 9 metallocorroles and the sites of oxidation reactions have been investigated, revealing that both variables change significantly within the group. According to spectroelectrochemistry, EPR, and UV-visible spectroscopic data it appears that: cobalt(III) corroles may be substitutionally labile compared to either Rh(III) derivatives or Ir(III) corroles of the present invention; the affinity of 5-coordinate derivatives for a sixth ligand increases dramatically down the row; and oxidation occurs unambiguously on the metal rather than on the corrole only in the case of iridium (i.e., Ir(III/IV)).

The electronic spectra of the 6-coordinate cobalt(III) and rhodium(III) corroles are quite similar to one another, while those of the iridium(III) complexes are significantly different (FIG. 14). 1-Co(py)$_2$ and 1-Rh(py)$_2$ display one major Soret band with almost the same $\lambda_{max}$ and two Q bands at about 580 and 600 nm, while 1-Ir(py)$_2$ displays a highly anisotropic Soret band and its Q bands are red-shifted by about 20 nm compared to those of the 3d and 4d complexes. It should be noted that 1-Co(py)$_2$ is in equilibrium with the mono-pyridine complex 1-Co(py) in CH$_2$Cl$_2$ solution [which is not the case for 1-Rh(py)$_2$ or 1-Ir(py)$_2$], and this latter species is responsible for the split Soret in the spectrum below. The spectrum of 1-Co(py)$_2$ in 5% pyridine (where only the bis-ligated form exists in solution) appears in FIG. 15 (at the top) and FIG. 34. As the primary components of the electronic spectra are corrole-based π-π* transitions in all cases, the differences may be attributed to more significant mixing of MLCT transitions in the order Co<Rh<Ir. Red shifted Q bands are also exhibited by the 5-coordinate 1-Ir(PPh$_3$), while the Soret bands differ very much within the series: 1-Co(PPh$_3$) has a highly split Soret band, 1-Rh(PPh$_3$) displays less splitting but is red-shifted, and 1-Ir(PPh$_3$) shows a single, broad Soret band.

Figure 16:
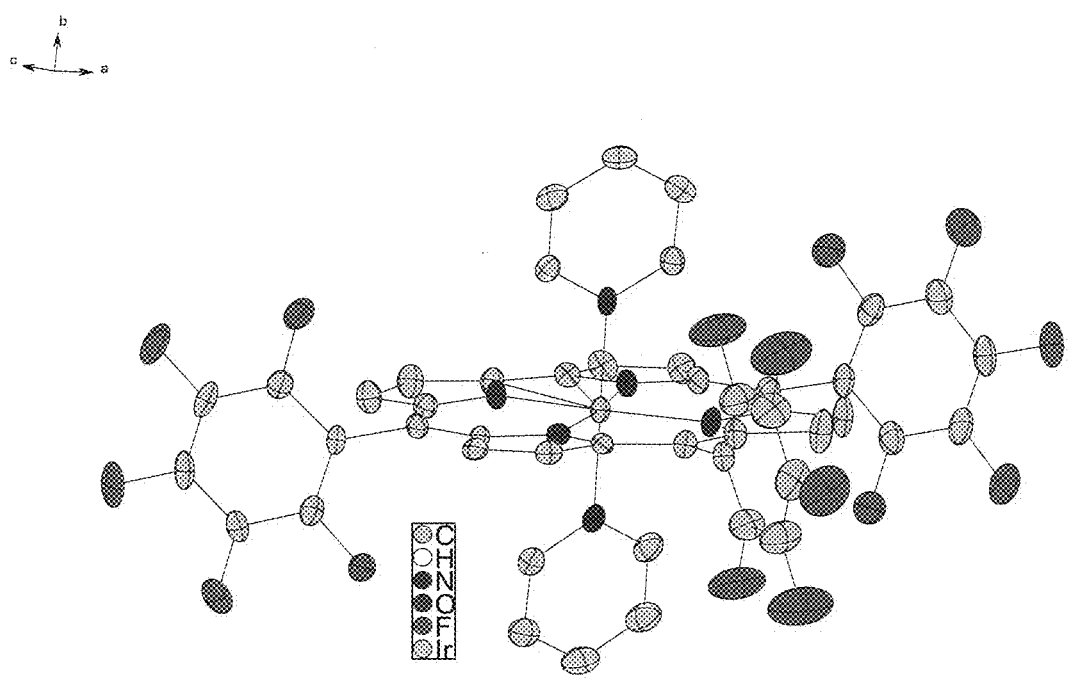
FIG. 16 is an illustration of the molecular structure of the bis-pyridine Ir(III) corrole 1-Ir(py)$_2$ (hydrogen atoms omitted).

The structures of 1-Ir(tma)$_2$ 1b-Ir(tma)$_2$ and 1-Ir(py)$_2$ have been compared with the structures of 1-Co(py)$_2$ and 1-Rh (py)$_2$ analogues. The main structural features of 1-Ir(py)$_2$ are: a very planar macrocyclic framework with a root-mean-square atomic deviation of 0.04 Å out of the plane defined by the N4 coordination core; an in-plane metal ion; and two essentially parallel pyridine rings (FIG. 16). The information compiled in Table 5 allows for a comparison of the metal-nitrogen bonds in 1-Ir(py)$_2$, 1-Co(py)$_2$, and 1-Rh(py)$_2$. The smaller cobalt(III) ion turns out to form considerably shorter bonds with both the corrole and the pyridine nitrogen atoms, while the differences between the rhodium(III) and the iridium(III) ions are not as great. The somewhat shorter Rh—N (pyrrole) bonds are consistent with the smaller ionic radius of rhodium(III) relative to iridium(III), while the shorter Ir—N (pyridine) bonds indicate that iridium(III) is a stronger Lewis acid than rhodium(III) within the coordination environment of the corrole.

TABLE 5

Comparison of metal-nitrogen bond lengths (Å) in 1-Co(py)$_2$, 1-Rh(py)$_2$, and 1-Ir(py)$_2$.

|  | M-N(corrole) | M-N(pyridine) |
|---|---|---|
| 1-Co(py)$_2$ | 1.873(4)-1.900(4) | 1.994(4)-1.995(4) |
| 1-Rh(py)$_2$ | 1.938(5)-1.976(5) | 2.060(5)-2.071(5) |
| 1-Ir(py)$_2$ | 1.947(2)-1.979(2) | 2.052(2)-2.066(2) |

1-Co(PPh$_3$) and 1-Rh(PPh$_3$) undergo different chemical reactions with pyridine: ligand substitution and addition to form 1-Co(py)$_2$ in the former case and addition only as to form 1-Rh(PPh$_3$)(py) in the latter case. The 1-Ir(PPh$_3$) complex behaves similarly to the rhodium(III) analog in this sense, i.e., addition of pyridine leads to a mixed-ligand complex. The substitutional lability of the cobalt(III) corrole is further exemplified in FIG. 15 (at the top), which shows that addition of PPh$_3$ to 1-Co(py)$_2$ leads to 1-Co(PPh$_3$) and that the former is re-formed upon addition of pyridine to the latter [notice that the spectrum changes slightly due to the elimination of any significant 1-Co(py) under excess pyridine]. Complementary information was obtained via the examination of spectral changes upon the addition of triphenylphosphine to the 5-coordinated metallocorroles. While addition of even a 100.000-fold excess of triphenylphosphine induced only minor changes in the spectrum of 1-Co(PPh$_3$), the major spectral changes of 1-Rh(PPh$_3$) (FIG. 15, middle) and 1-Ir (PPh$_3$) (FIG. 15, bottom) were complete after the addition of 6300 and 350 equivalents, respectively. The similarity of the visible spectra obtained upon addition of triphenylphosphine to 1-Rh(PPh$_3$) and 1-Ir(PPh$_3$) to those of 1-Rh(py)$_2$ and 1-Ir (py)$_2$, respectively, suggest that PPh$_3$ addition to the former complexes produces the six-coordinate bis-triphenylphosphine species 1-Rh(PPh$_3$)$_2$ and 1-Ir(PPh$_3$)$_2$. While various corrolato-chelated metal(III) ions have been observed to possess surprisingly low affinity for a sixth ligand, these results demonstrate that this effect becomes much less pronounced upon moving downwards within the periodic table. This may be attributed to the stronger Lewis acidity of 4d and especially 5d metal ions, such that coordination of a sixth σ-donating ligand becomes much more favorable moving down the group. This phenomenon plays a role in understanding the results presented in the following sections.

Figure 17:
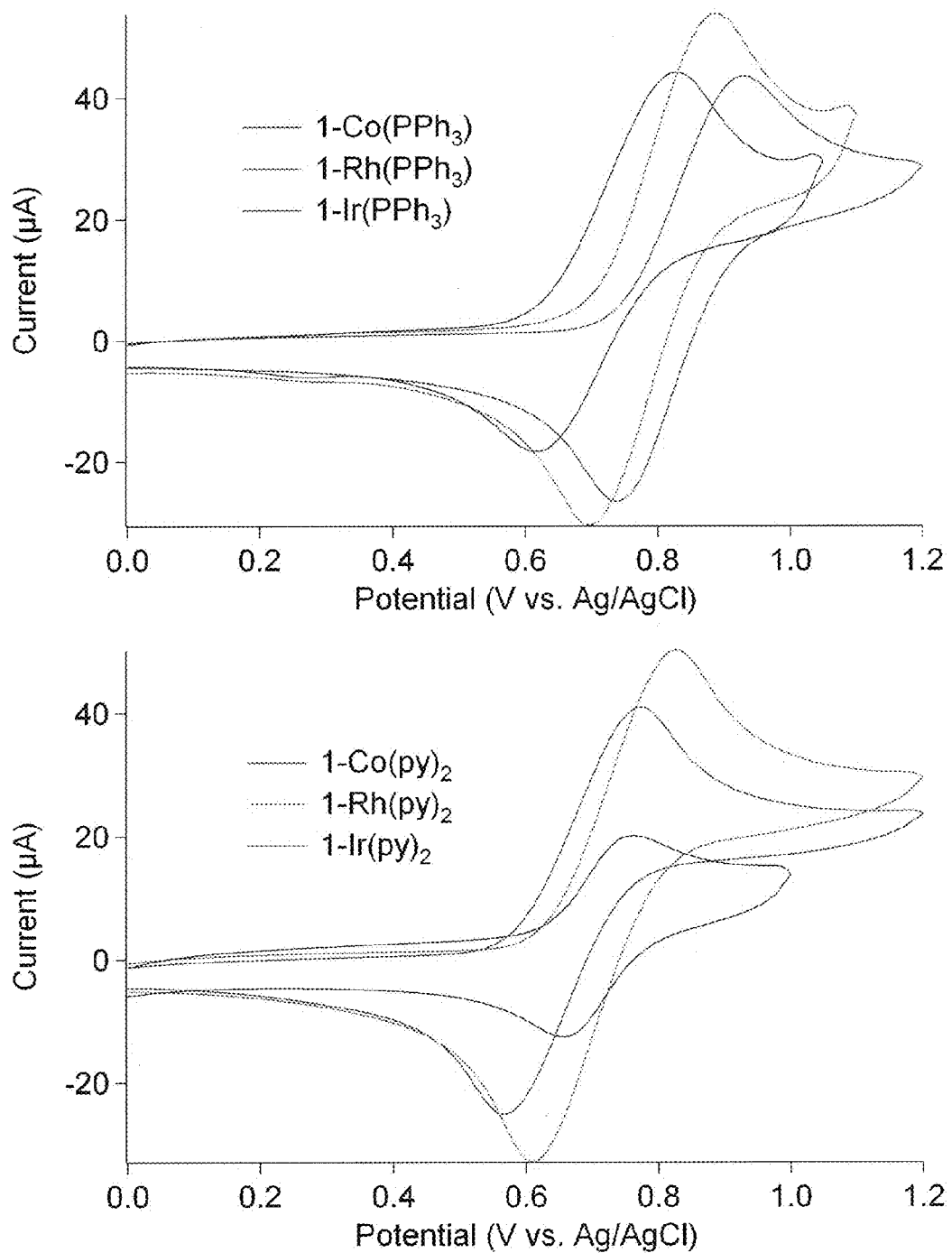
FIG. 17 is a series of graphs of CV traces of CH$_2$Cl$_2$ solutions of the 1-M(PPh$_3$) and 1-M(py)$_2$ complexes.

Electrochemistry. Investigation of the differences between the β-pyrrole-unsubstituted complex 1-Ir(tma)$_2$ and its fully brominated analog 1b-Ir(tma)$_2$ reveals that the latter displays one oxidation and one reduction within the solvent potential window of CH$_2$Cl$_2$, while no reduction and two reversible oxidations were observed for the former. The first positive redox potentials of the complexes might reflect either metal-centered (M(III)/M(IV), where M=Co, Rh, or Ir) or ligand-centered (tpfc/tpfc$^+$) processes. The cyclic voltammograms of all complexes are shown in FIG. 17, while Table 6 lists the corresponding half-wave potentials. The results reveal that the 6-coordinated 1-M(py)$_2$ complexes are oxidized at lower potentials than the 5-coordinated 1-M(PPh$_3$) complexes and that the difference becomes smaller in the order of Ir<Rh<Co. The most surprising result is the very small difference in redox potentials for the differently metallated compounds: 0.70±0.03 for 1-M(py)$_2$ and 0.78±0.06 for 1-M(PPh$_3$). A metal-based process (M$^{III}$/M$^{IV}$) throughout the series may be ruled out because of the very large effects that would be expected in such a case, as may be exemplified by the 0.2-0.3 V more positive redox potentials of the Rh$^{III/IV}$ couple relative to the Ir$^{III/IV}$ couple in cyclometalated complexes. On the other hand, the central metal ion should have a pronounced effect even if the macrocycle is oxidized, as has been observed for both corroles and porphyrins. This emphasized the need for a more detailed investigation of the processes, which was performed via spectroscopic examination of the oxidation products.

TABLE 6

Redox potentials (CH$_2$Cl$_2$, TBAP, vs. Ag/AgCl) for the first oxidation processes of the Group 9 metal(III) corrole complexes. Under identical conditions, the E$_{1/2}$ for ferrocene was 0.55 V; and iodine displayed an E$_{pa}$ of 0.89 V and an E$_{pc}$ of 0.39 V.

| 1-M(PPh$_3$)$_2$ | E$_{1/2}$ | 1-M(py)$_2$ | E$_{1/2}$ |
|---|---|---|---|
| M = Co | 0.83 | M = Co | 0.67 |
| M = Rh | 0.79 | M = Rh | 0.72 |
| M = Ir | 0.72 | M = Ir | 0.71 |

Figure 18:
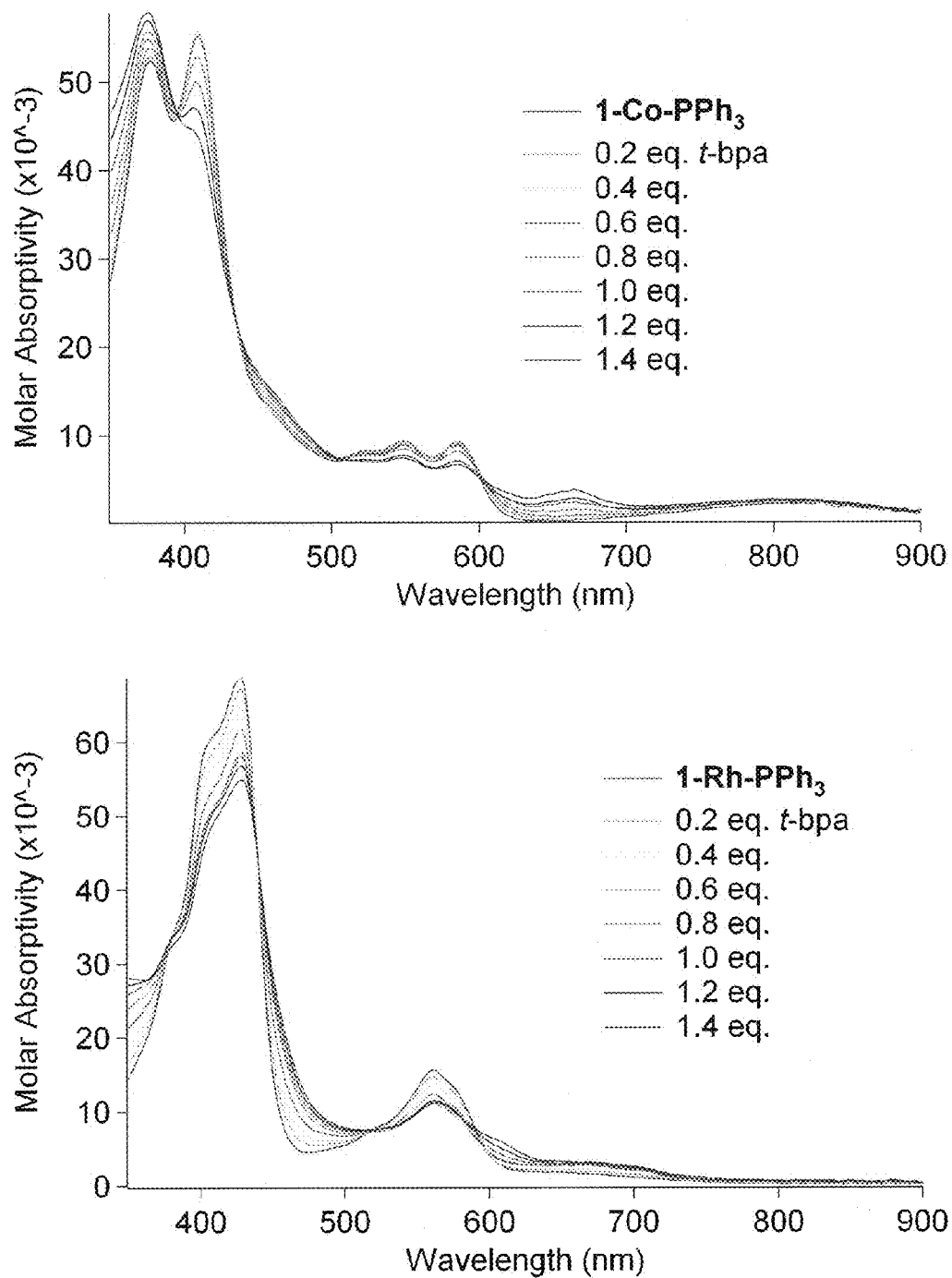
FIG. 18 is a series of graphs illustrating changes in the electronic spectra indicating oxidation of 1-Co(PPh$_3$) (top) and 1-Rh(PPh$_3$) (bottom) by tris(4-bromophenyl)aminium-hexachloroantimonate (t-4bpa) in CH$_2$Cl$_2$.
Figure 19:
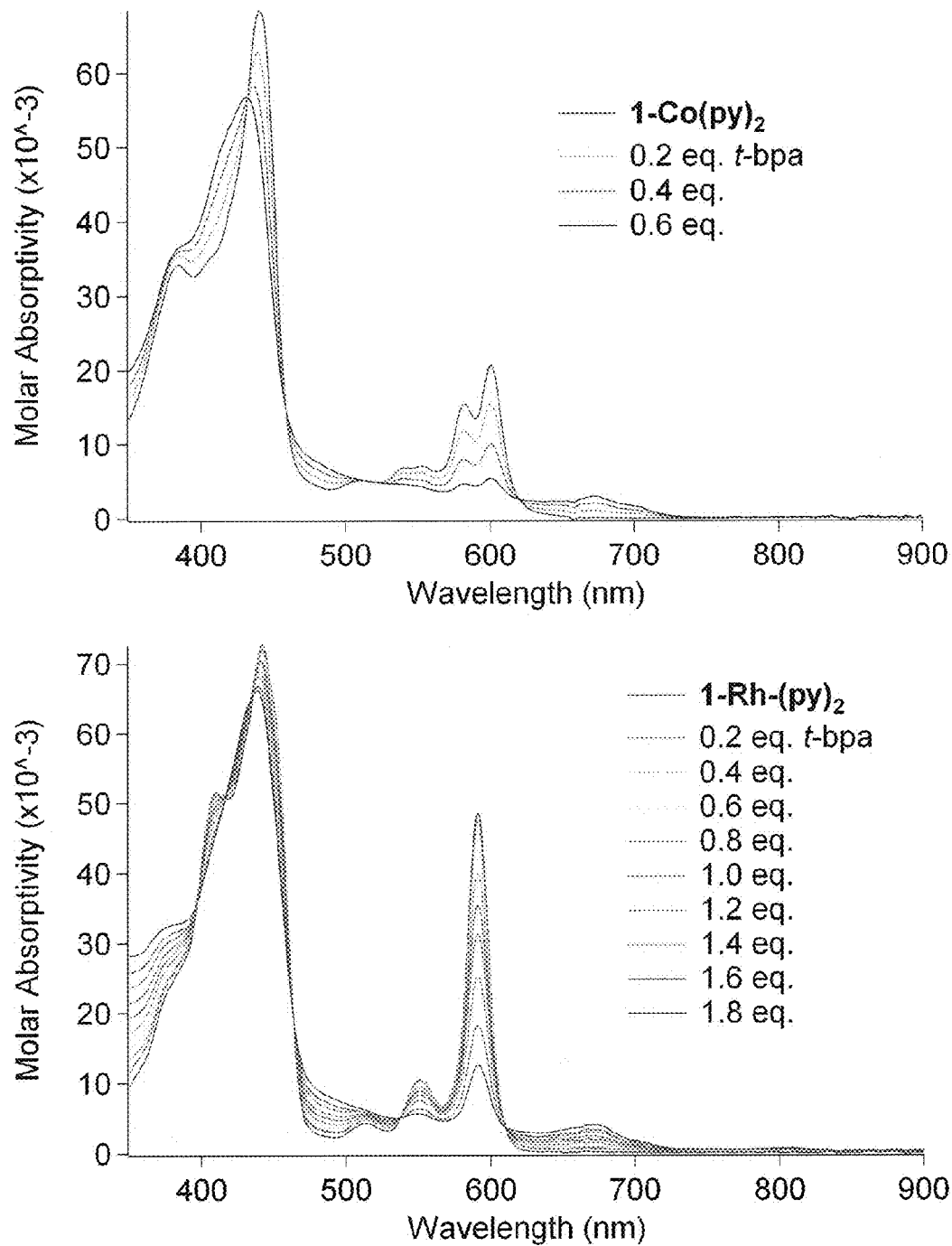
FIG. 19 is a series of graphs illustrating changes in the electronic spectra indicating oxidation of 1-Co(py)$_2$ (top) and 1-Rh(py)$_2$ (bottom) by t-4bpa in CH$_2$Cl$_2$.

Visible Spectroscopy of the One-electron-oxidized Metal (III) Corroles: Changes in the electronic spectra upon oxidation were used as a tool for analyzing whether the metal or the corrole is the center of the redox reactions, relying on two different chemical oxidants (iodine and t-4bpa) and spectro-electrochemistry. The advantage of using molecular iodine is that it should not be able to induce double oxidation (Table 6), while the t-4bpa cation is a good choice of oxidant because (unlike iodine) its reduced products do not interact with the metal center. One-electron oxidation of 1-Co(PPh$_3$) and 1-Rh (PPh$_3$) by either iodine (FIGS. 31 and 32) or t-4bpa (FIG. 18) induced a significant reduction of the intensity of the original Soret and Q bands and the formation of a new broad band that appears at 690 nm (∈=4000) for the cobalt complex and at 710 nm (∈=2300) for the rhodium complex. These characteristics are consistent with corrole-centered oxidation, i.e., formation of corrole radicals. Despite their less positive redox potentials, the six-coordinate complexes 1-Co(py)$_2$ and 1-Rh (py)$_2$ seemed inert to iodine oxidation, but could still be oxidized with t-4bpa (FIG. 19). The indications for formation of corrole radicals upon oxidation are even stronger in these complexes than in the five-coordinate cases, as the new bands at long wavelength are more pronounced and the Soret bands undergo small hypsochromic shifts.

Figure 14:
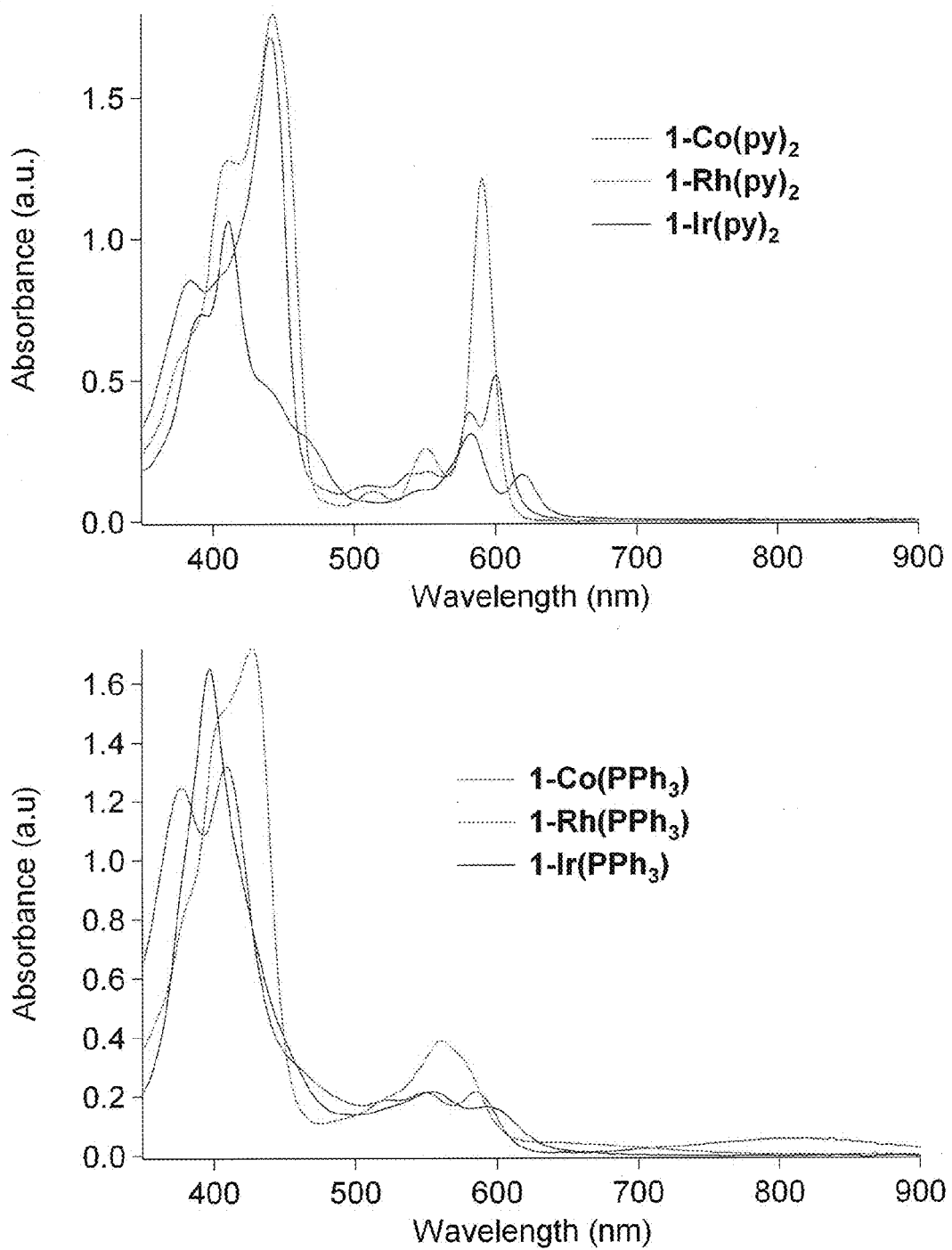
FIG. 14 is a graph of electronic spectra of the 6-coordinate bis-pyridine metal (III) corroles (top) and the 5-coordinate PPh$_3$-coordinated metal(III) corroles (bottom), at 2.5 µM concentration in CH$_2$Cl$_2$.
Figure 15:
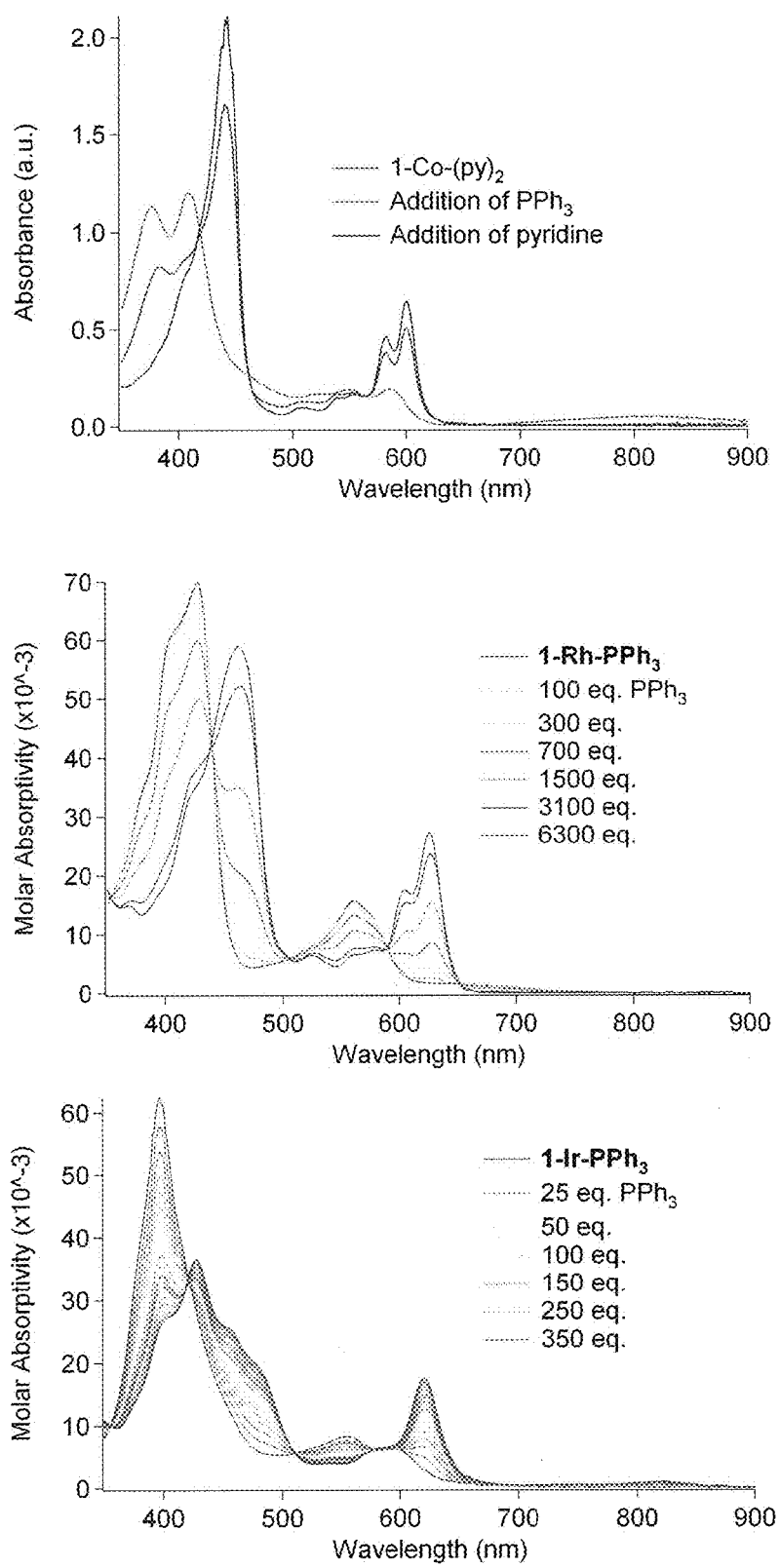
FIG. 15 is a series of graphs illustrating the changes in the electronic structure in CH$_2$Cl$_2$ that demonstrate (from top): the reversible transformations between 1-Co(py)$_2$ and 1-Co(PPh$_3$) upon addition of PPh$_3$ and pyridine; formation of 1-Rh(PPh$_3$)$_2$ from 1-Rh(PPh$_3$); and formation of 1-Ir(PPh$_3$)$_2$ from 1-Ir(PPh$_3$).

The spectral changes upon oxidation of the iridium(III) corroles are significantly different from those of their 3d and 4d analogs. Oxidation of 1-Ir(PPh$_3$) by iodine results in a severe decrease in the intensity of the Soret band, accompanied by splitting and broadening, as well as almost complete disappearance of the Q bands. Concomitantly, two new absorption bands arise at and above 700 nm, of which the more intense one, at 840 nm (∈=5000), may be assigned as an LMCT transition from the corrole to a newly formed iridium (IV) center. Oxidation of the same complex by t-4bpa instead of iodine results in two distinct oxidation processes with their own sets of isosbestic points (FIGS. 20a and b). The first process, which appears to occur with near exclusivity up to about 0.6 equivalents of t-4bpa, results in a less intense Soret band, the total disappearance of any Q-band structure, and the rise of small bands at 695 nm ($\in$=2800) and 821 nm ($\in$=2000). One important aspect of the spectral changes is that the Soret band of singly oxidized 1-Ir(PPh$_3$) strongly resembles those of the six-coordinate iridium(III) corroles 1-Ir(py)$_2$ (FIG. 14, top) and 1-Ir(PPh$_3$)$_2$ (FIG. 15, middle). The second process results in the rise of a weak, bathochromically shifted Soret band at 460 nm ($\in$=30000) coincident with the growth of a new Q-band at 580 nm ($\in$=5700) as well as a red-shifted and more intense LMCT band at 833 nm ($\in$=4500). In contrast with 1-Ir(PPh$_3$), but similarly to the cases of 1-Co(py)$_2$ and 1-Rh(py)$_2$, 1-Ir(py)$_2$ seems not to react with iodine according to visible spectroscopy. Its oxidation by t-4bpa reveals isosbestic points up when up to 1.1 equivalents of oxidant are used, leading to a spectrum that displays diminished Soret and Q bands and new bands with about equal intensity at 683 and 793 nm that seem similar to the LMCT bands observed in the spectra of oxidized 1-Ir(PPh$_3$) (FIG. 20c). Larger amounts of t-4bpa were used as well, but this led to an uninterpretable spectrum, possibly due to decomposition of the corrole. The different results obtained with iodine vs. t-4bpa as an oxidant for the two types of complexes, as well as the apparent changes that occur during oxidation of the iridium(III) corroles by even less than one equivalent of t-4bpa, were investigated by spectroelectrochemistry.

Figure 31:
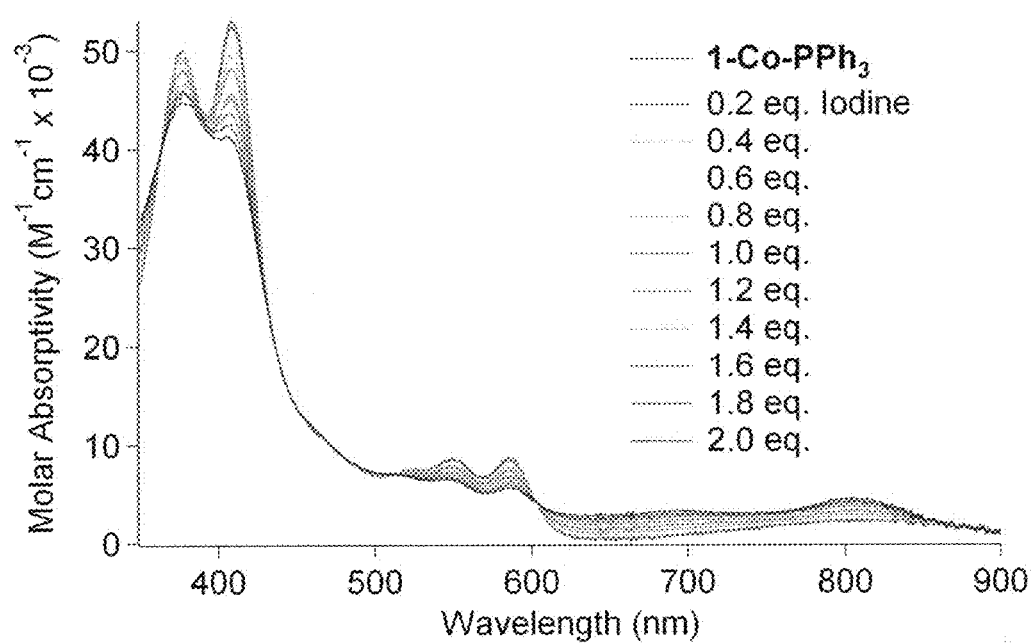
FIG. 31 is a graph illustrating changes to the electronic absorption spectrum of 1-Co(PPh$_3$) in CH$_2$Cl$_2$ upon reaction with iodine.

The changes in the visible spectrum of 1-Ir(PPh$_3$) were examined at 1.0 V, which is high enough to assure full oxidation, but low enough to avoid double oxidation. Nevertheless, two complexes are clearly formed (FIG. 31): the first, with a new band at 811 nm and a relatively simple Soret band, is later transformed into a species whose Soret band is heavily split, which has a new Q band at 580 nm, and which displays a low energy band at 844 nm (FIG. 31, inset). These results confirm the proposed mechanism of chemical oxidation, as virtually identical changes were observed for the combination of 1-Ir(PPh$_3$) with t-4bpa. The first band that appears at 811 nm clearly represents the one-electron oxidation product, but the initial product is clearly unstable: it transforms into a new molecular species even when a second oxidation is arrested by either controlling the electrochemical potential or by adding less than one equivalent of chemical oxidant. The similarity of the final Soret band obtained upon both chemical and electrochemical oxidation of 1-Ir(PPh$_3$) to those of 6-coordinated iridium(III) corroles seems to suggest that the apparent instability of the initial oxidation product is due to the increased ligand affinity of iridium(IV), resulting in binding of a sixth ligand from the electrolyte, the oxidant or solvent impurities.

Figure 22:
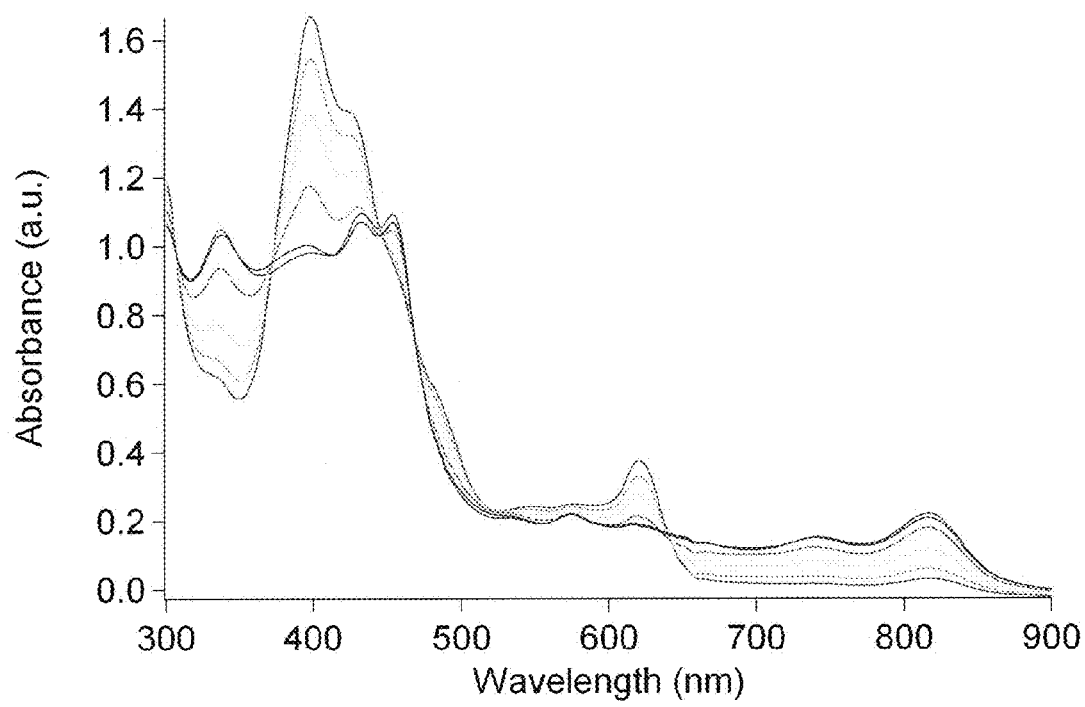
FIG. 22 is a graph of spectroelectrochemical results for a CH$_2$Cl$_2$ solution of 1-Ir(PPh$_3$) containing 5 equivalents of PPh$_3$ at 1.0 V vs. Ag/AgCl; where the starting material is red and the final product is purple.

The above hypothesis regarding the apparent instability of the one-electron oxidation product was examined by performing the spectroelectrochemistry of 1-Ir(PPh$_3$) in the presence of 5 equivalents of PPh$_3$ (FIG. 22). This resulted in an almost perfectly clean conversion to the final product obtained in the absence of PPh$_3$, thus indicating that the initially formed complex has a large affinity for a sixth ligand and becomes much more stable when it is supplied. All the results are consistent with expectations for a genuine iridium (IV) complex, which would not necessarily display significant changes in the Soret band unless its coordination number changes, but should have increased affinity for a sixth ligand and show an LMCT transition at above 800 nm.

EPR Spectra of oxidized iridium(III) corroles. Both organic radicals and d$^5$ iridium ions are paramagnetic, S=½ systems, but EPR spectroscopy can almost always be used to distinguish between the two. Carbon-centered organic radicals, such as that of H$_3$tpfc or its gallium(III) complex, tend to have g tensor values very close to the free electron value of g=2.0023, with little hyperfine coupling and no g tensor anisotropy. On the other hand, iridium(IV) compounds display highly anisotropic signals, often accompanied by hyperfine couplings to the metal nucleus and/or other EPR-active nuclei.

In order to facilitate characterization of their singly oxidized forms, complexes 1-Co(py)$_2$, 1-Rh(py)$_2$, and 1-Ir(py)$_2$ were oxidized chemically, and their EPR spectra were then recorded in frozen toluene solutions. With t-4bpa as oxidant, the spectrum of the oxidized cobalt complex displays one narrow band centered at g=2.006 (FIG. 23a), clearly indicating that this species is a delocalized corrole radical. The oxidized rhodium complex displays a broader line with some additional features in its EPR spectrum (FIG. 23b), which can best be modeled as a largely corrole-based radical with moderate spin density on the rhodium nucleus (g$_\parallel$=2.032, g$_\perp$=2.001, g=2.016). Similar results, i.e., both pure corrole radicals and metal-coupled corrole radicals, have been previously observed for high valent cobalt corroles and corrolazines (5,10,15-triazacorroles). A more uncommon result was obtained in the case of the six-coordinated iridium(III) corrole. Iodine, though not producing UV-vis spectral changes upon its addition to 1-Ir(py)$_2$, was used in the EPR: experiments in order to confirm the hypothesis that it nevertheless affects oxidation. Addition of iodine to a toluene solution of the corrole (FIG. 23c) results in a highly rhombic spectrum (g$_{zz}$=2.044, g$_{yy}$=1.993 g=1.836, g=1.958) that is clearly inconsistent with oxidation centered on the corrolato ligand. On the other hand, the spectrum is very similar to those of low-spin d$^5$ metalloporphyrinoids such as bis-amine-iron(III) porphyrins and (tpfc)Fe(py)$_2$, the bis-pyridine-iron(III) complex of the same corrole that was utilized in the current studies. These data indicate that the first oxidation process in 1-Ir(py)$_2$ occurs at the metal, resulting in an iridium(IV) complex. Meanwhile, the cobalt corrole becomes an unambiguous organic radical upon oxidation, and the rhodium complex displays an EPR spectrum consistent with a highly coupled organic radical system.

The EPR results from oxidation of the five-coordinate complexes [1-Co(PPh$_3$), 1-Rh(PPh$_3$), and 1-Ir(PPh$_3$)] were less straightforward due to apparent problems with decomposition and/or binding of oxidants, although the spectra of singly oxidized cobalt and rhodium corroles are quite similar to those of their hexacoordinate analogs. Much more ambiguous results were obtained for the (triphenylphosphine)iridium (III) corrole complex, compounding the evidence that the oxidized form of 1-Ir(PPh$_3$) undergoes chemical reactions due to increased affinity for a sixth ligand upon oxidation.

The investigation of the reactivity patterns of an isostructural series of transition metal corroles is highly illuminating in terms of chemical reactivity and the stability of high oxidation states. There is a clear trend within the series in terms of ligand substitution (only cobalt(III) corroles undergo it at room temperature) and ligand addition (Co<Rh<Ir), while all complexes display virtually identical electrochemical redox potentials. The unexpected insensitivity of the oxidation potentials to the metal ions has been resolved for the six-coordinated complexes by invoking different centers of oxidation for each complex. Spectral data demonstrate that the first oxidation is corrole-centered for cobalt, corrole-based with some metal contribution for rhodium, and metal-centered for iridium. Regarding the five-coordinate complexes, the results imply that these compounds increase in affinity for a sixth ligand by three to four orders of magnitude as one moves from cobalt to rhodium and then to iridium. These results indicate that iridium corroles behave very differently from their 3d and 4d analogs.

The electronic structures of metallocorrole complexes (tpfc)M$^{III}$(NH$_3$)$_2$, where tpfc is the anion of 5,10,15-(tris) pentafluorophenylcorrole and M=Co, Rh, a) have been computed by DFT methods (B3LYP with Poisson-Boltzmann continuum solvation). In each case, one-electron oxidation is calculated to occur from a ligand-based orbital (HOMO of B$_1$ symmetry). Variations in the calculated M(IV/III) reduction potentials (0.64, 0.67, and 0.56 V vs SCE for M=Ir, Rh and Co, respectively) are small compared to expectation for metal-based oxidations. Excited states with substantial metal character are well separated from the ground state in the one-electron-oxidized cobalt corrole.

Electronic structure calculations may provide insight into the factors that determine the stability and reactivity of metal complexes in high oxidation states and could in principle facilitate the design of catalysts for substrate oxidation reactions. One issue that such calculations may address is that the metal-chelating ligands themselves often undergo redox changes during catalysis. Such noninnocent ligand behavior may be a hallmark of oxidative catalytic cycles of heme enzymes, where a highly reactive intermediate formed by two-electron oxidation of an iron(III) precursor is better described as an oxoiron(IV) ligand radical than as an iron(V) complex. Depending on the particular enzyme, one unpaired electron is located on either an orbital of the chelating porphyrin or on a nearby amino acid residue. Notably, advances in synthesis, together with high level spectroscopy and theory, have continued to provide insights into these and related issues, with surprising findings in certain cases: for example, the likelihood of a role for electronic excited-state coupling in promoting catalytic hydroxylations by heme and nonheme-iron enzymes.

The successful syntheses of five- and six-coordinate iridium(III) corroles completed a very rare isostructural 3d ($Co^{III}$), 4d ($Rh^{III}$) and 5d ($Ir^{III}$) series, and prompted the development of electronic structural descriptions of analogous 3d-4-d-5d Group 9 metallocorroles. Surprisingly, the measured redox potentials show slight variation among the three corroles, while EPR results suggest a shift from corrole- to metal-centered oxidation in moving from 3d and 4d to 5d complexes. In particular, electronic structure calculations may provide an explanation for the small differences in Co(IV/III), Rh(IV/III) and Ir(IV/III) reduction potentials, and the greatly enhanced metal character indicated by EPR experiments in going from "Rh(IV)" to "Ir(IV)".

Density functional theory (DFT) was used for the determination of metallocorrole electronic structures. The structural parameters of $(tpfc)Ir(NH_3)_2$ (tpfc=5,10,15-tris-pentafluorophenylcorrole) from the calculation are consistent with those obtained from X-ray diffraction crystallographic measurements. Calculations were made of the redox potentials as well as the electronic structures of $[(tpfc)M(NH_3)_2]^{0/+}$. Additionally, less computationally taxing $[(tfc)M(NH_3)_2]^{0/+}$ (tfc=5,10,15-trifluorocorrole) models were examined. Of special interest is that computational results show that the very small nd (n=3,4,5) dependence of the reduction potentials of Group 9 metallocorroles is accompanied by a marked decrease in metal orbital energies (compared with those of the corrole) in the order 3d to 4d to 5d.

All computations were conducted with the Jaguar 7.0 package (release 207), applying the hybrid density functional B3LYP. Although no single functional has been shown to be superior for applications to spectroscopy, magnetic properties and transition metal thermochemistry, B3LYP has proved useful in the calculation of oxidation potentials and yielded spin density distributions and excited state orderings similar to CASPT2 results for an iron-heme model. Free energies used in the calculation of oxidation potentials are equal to:

$$G=E_{el,gas}+G_{solv}+ZPE+H_{vib}-S_{vib}T$$

where $E_{el,gas}$ is the gas phase electronic energy, $G_{solv}$ is the solvation energy of the compound in dichloromethane, ZPE is the zero-point energy of the complex, $H_{vib}$ is the vibrational enthalpy, and $S_{vib}$ is the vibrational entropy. The temperature was set to 298 K for all calculations. Geometries were optimized and hessians for vibrational spectra were calculated in vacuum using the Los Alamos effective core potential with 2-ζ valence functions for the metals and 6-31G for all other atoms. Single point energies were then calculated using a 3-ζ contraction of the Los Alamos valence functions augmented with two f-functions for metals and 6-311G++ for other atoms. Solvation energies were obtained at the vacuum-optimized geometries with the Poisson-Boltzmann continuum solvation model using a dielectric constant of ∈=8.93 and probe radius of 2.33 Å to represent dichloromethane. The oxidation potentials (in V) relative to the standard hydrogen electrode (SHE) were calculated according to the equation $$E_{SHE}=(G_{ox}-G_{red})/(N_{el})(23.06\ kcal/mol\cdot eV)-4.29V,$$

and the corresponding potentials relative to the saturated calomel electrode (SCE) are $$E_{SCE}=E_{SHE}-0.24V,$$

where $G_{ox}$ is the Gibbs free energy (in kcal/mol) of the oxidized form of the complex and $G_{red}$ is that of the reduced form.

To simplify orbital analysis of excited states, geometries of the $(tpfc)M^{III}(NH_3)$ and $(tfc)M^{III}(NH_3)_2$ complexes were optimized with $C_{2v}$ symmetry enforced. Then, single point energy calculations using the 2-ζ basis were performed on the corresponding "M(IV)" complexes to obtain the energies of various states with the electron taken from different orbitals of the M(III) complexes. Level-shifting was applied to aid convergence of the excited states. The spin densities and charges on the metals were also obtained through Mulliken analysis. Unless otherwise stated in the text, upper-case symmetry labels (e.g. $^1A_2$) denote excited states with the electron ionized from an orbital of the corresponding symmetry. The orbitals themselves are denoted by lower-case symmetry labels (e.g. $^1a_2$).

Figure 38:
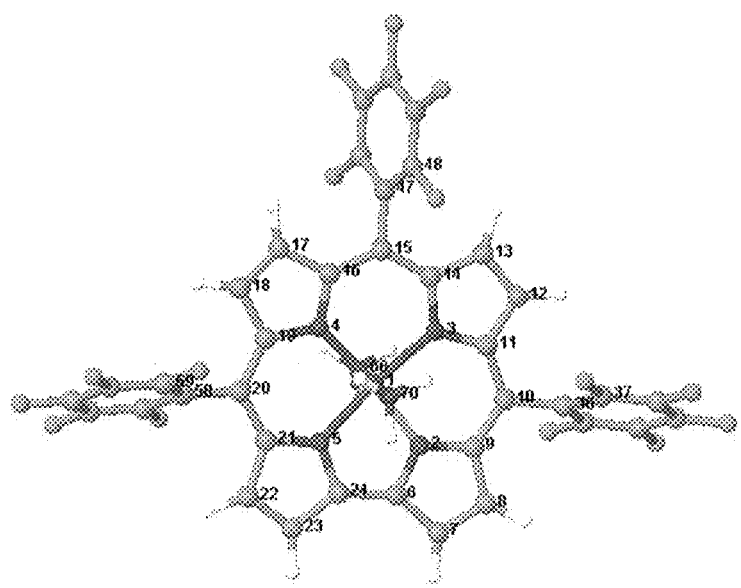
FIG. 38 is an illustration of the atom numbering scheme used in electronic structure calculations for compounds according to embodiments of the present invention; hydrogen atoms are in white, carbon atoms are in grey, nitrogen atoms are in blue, fluorine atoms are in green, and the metal is in lighter blue; note that the numbering of the corrole ring is different from the numbering convention of molecular nomenclature.

The crystal structure of $(tpfc)Ir(NH_3)_2$ shows a quasi-C2v symmetry around the metal center with the principal axis passing through Ir and C15 (FIG. 38). The experimental Ir—N(ammine) bond lengths are 2.074 Å each, and the average Ir—N(pyrrole) bond length is 1.964 Å. The computed Ir—N(ammine) and Ir—N(pyrrole) bond length are, respectively 2.112 and 1.976-1.996 Å, in good agreement with the crystallographic data. Dihedral angles of the pentafluorophenyl groups in vacuum-optimized structures were 66-76 degrees. The energy change caused by rotation of the pentafluorophenyl groups away from perpendicular averages 0.03 eV, which is on the same order of magnitude as the uncertainty in energy computations. This small energy penalty is consistent with dihedral angles in practically all triarylcorrole structures.

The computed increases in the length of the bonds C10-C11 and C6-C24 Table 7) upon removal of an electron from the neutral complexes are consistent with the description in a previous publication of bond length changes upon formation of a corrole-based cation radical of $B_1$ symmetry. Changes in both types of metal-nitrogen bond lengths (M-$N_{pyrrole}$ and M-$NH_3$) are much smaller, suggesting that the oxidation state of the metal stays the same upon removal of one electron from these complexes.

TABLE 7

Key bond lengths of [(tpfc)M(NH3)2]0/+, for M = Co, Rh, and Ir. The number in parenthesis following the atomic symbol of the metal is the formal oxidation state of the metal in the corresponding complex, i.e., considering the corrole ligand as non-oxidized.

| tpfc | Co(III) | Co(IV) | delta | Rh(III) | Rh(IV) | delta | Ir(III) | Ir(IV) | delta |
|---|---|---|---|---|---|---|---|---|---|
| M-N66 | 1.988 | 1.995 | 0.007 | 2.107 | 2.114 | 0.007 | 2.112 | 2.119 | 0.007 |
| M-N70 | 1.987 | 1.992 | 0.005 | 2.108 | 2.116 | 0.008 | 2.112 | 2.120 | 0.008 |
| Average M-N (NH3) | 1.988 | 1.994 | 0.006 | 2.108 | 2.115 | 0.007 | 2.112 | 2.120 | 0.008 |
| M-N2 | 1.887 | 1.888 | 0.001 | 1.967 | 1.968 | 0.001 | 1.976 | 1.976 | 0.000 |
| M-N3 | 1.916 | 1.913 | −0.003 | 1.993 | 1.991 | −0.002 | 1.997 | 1.996 | −0.001 |
| N2-C6 | 1.37 | 1.356 | −0.014 | 1.369 | 1.355 | −0.014 | 1.371 | 1.356 | −0.015 |
| N2-C9 | 1.36 | 1.371 | 0.011 | 1.356 | 1.365 | 0.009 | 1.36 | 1.367 | 0.007 |
| N3-C11 | 1.386 | 1.373 | −0.013 | 1.38 | 1.368 | −0.012 | 1.383 | 1.37 | −0.013 |
| N3-C14 | 1.371 | 1.375 | 0.004 | 1.365 | 1.369 | 0.004 | 1.368 | 1.371 | 0.003 |
| C6-C24 | 1.425 | 1.442 | 0.017 | 1.446 | 1.466 | 0.020 | 1.45 | 1.471 | 0.021 |
| C9-C10 | 1.414 | 1.401 | −0.013 | 1.428 | 1.414 | −0.014 | 1.429 | 1.415 | −0.014 |
| C10-C11 | 1.408 | 1.431 | 0.023 | 1.422 | 1.447 | 0.025 | 1.425 | 1.449 | 0.024 |
| C14-C15 | 1.410 | 1.414 | −0.004 | 1.424 | 1.428 | −0.004 | 1.426 | 1.429 | −0.003 |

Figure 39:
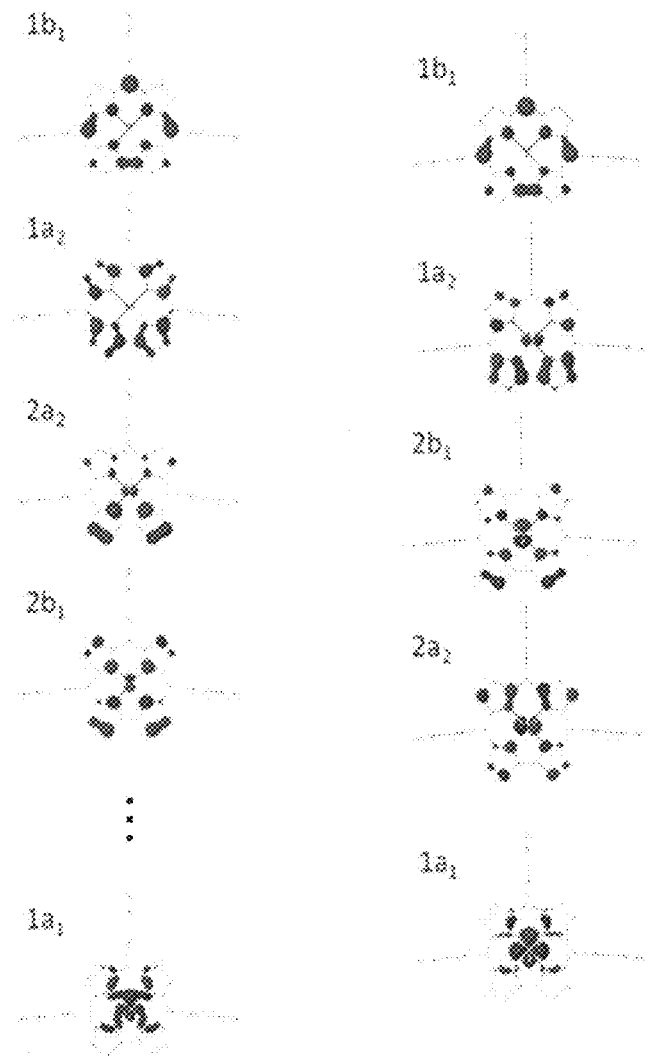
FIG. 39 is an illustration of the molecular orbital (MO) surfaces (isovalue=−0.05) calculated for (tpfc)M(NH$_3$)$_2$, where M=Rh (left; Co shows similar results) and Ir (right); the topmost MO is the HOMO, which is followed by HOMO-1, and so on, until the MO above 1a$_1$ is reached; 1a$_1$ is HOMO-13 when M=Rh, HOMO-14 when M=Co, and HOMO-4 when M=Ir.

As expected, the ground state of [(tpfc)Ir(NH$_3$)$_2$] displays six dπ electrons and a closed-shell corrole π-system (FIG. 39). In the ground state of [(tpfc)Ir(NH$_3$)$_2$]$^+$, the d$^6$ configuration on Ir remains intact while the 1b$_1$ orbital of the corrole is singly occupied. There is effectively no spin density on the metal, and the atomic charge of Ir from Mulliken population analysis remains essentially constant (0.87 to 0.89). Co and Rh present similar features.

Figure 40:
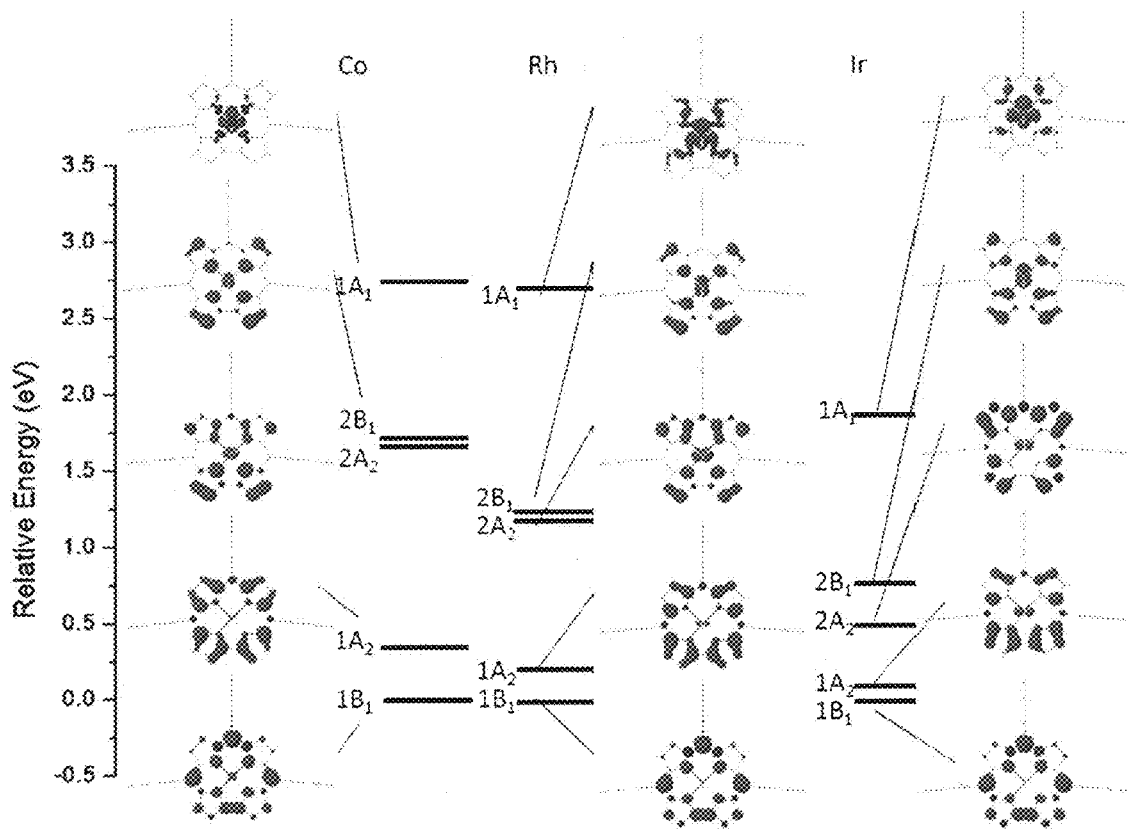
FIG. 40 is an illustration of the relative energies and spin density surfaces (isovalue=0.002) calculated for [(tpfc)M(NH$_3$)$_2$]$^+$ (M=Co, Rh, Ir).

The relative energies as well as the metal spin densities of excited states of [(tpfc)M(NH$_3$)$_2$]$^+$ are compared in Table 8. The spin density plots in FIG. 40 show that the higher-energy excited states for each metal, particularly for iridium, contain significant metal character. Although the pentafluorophenyl group (C$_6$F$_5$) was the meso-substituent used in experiments, the imaginary [(tfc)M(NH$_3$)$_2$]$^+$ complexes were also calculated because simpler meso-substituents greatly reduce the time required for computation. The tpfc complexes also often ended up on a saddle point due to a shallow potential energy surface caused by rotation of the C$_6$F$_5$ groups. Parameters for the tfc complexes can be found in Table 9, and the spin density surfaces and energy levels of these complexes can be viewed in FIG. 41.

TABLE 8

Spin densities and energies of the excited states of the tpfc complexes. The symmetry label of the state is the symmetry of the orbital from which the electron has been ionized. Relative energy is the energy of the state in question minus that of the lowest energy ionized state of the same compound. Metal spin density represents the spin density on the metal, in total unpaired electron spins. There are other states with the unpaired electron on corrole-based orbitals between 2B$_1$ and 1A$_1$ for Rh and Co.

| | Co | | Rh | | Ir | |
|---|---|---|---|---|---|---|
| tpfc State | Relative energy (eV) | Metal spin density | Relative energy (eV) | Metal spin density | Relative energy (eV) | Metal spin density |
| 1B$_1$ | 0.00 | −0.02 | 0.00 | −0.01 | 0.00 | −0.01 |
| 1A$_2$ | 0.27 | 0.00 | 0.24 | 0.02 | 0.15 | 0.07 |
| 2A$_2$ | 1.63 | 0.10 | 1.23 | 0.21 | 0.59 | 0.08 |
| 2B$_1$ | 1.71 | 0.12 | 1.27 | 0.24 | 0.86 | 0.38 |
| 1A$_1$ | 2.74 | 1.13 | 2.71 | 0.75 | 2.06 | 0.89 |

TABLE 9

Spin densities and energies of the excited states of the tfc complexes. The symmetry label of the state is the symmetry of the orbital from which the electron has been ionized. Relative energy is the energy of the state in question minus that of the lowest energy ionized state of the same compound. Metal spin density represents the spin density on the metal, in total unpaired electron spins. There are other states with the unpaired electron on corrole-based orbitals between 3B$_1$ and 1A$_1$ for Rh and Co.

| | Co | | Rh | | Ir | |
|---|---|---|---|---|---|---|
| tfc State | Relative energy (eV) | Metal spin density | Relative energy (eV) | Metal spin density | Relative energy (eV) | Metal spin density |
| 1B$_1$ | 0.00 | −0.02 | 0.00 | −0.01 | 0.00 | −0.01 |
| 1A$_2$ | 0.67 | 0.00 | 0.63 | 0.02 | 0.54 | 0.07 |
| 2A$_2$ | 1.94 | 0.08 | 1.58 | 0.19 | 1.21 | 0.24 |
| 2B$_1$ | 2.02 | 0.10 | 1.62 | 0.22 | 1.21 | 0.35 |
| 3B$_1$ | 2.33 | −0.01 | 2.28 | 0.00 | 2.27 | 0.00 |
| 1A$_1$ | 3.19 | 1.16 | 3.19 | 0.77 | 2.53 | 0.91 |

Figure 41:
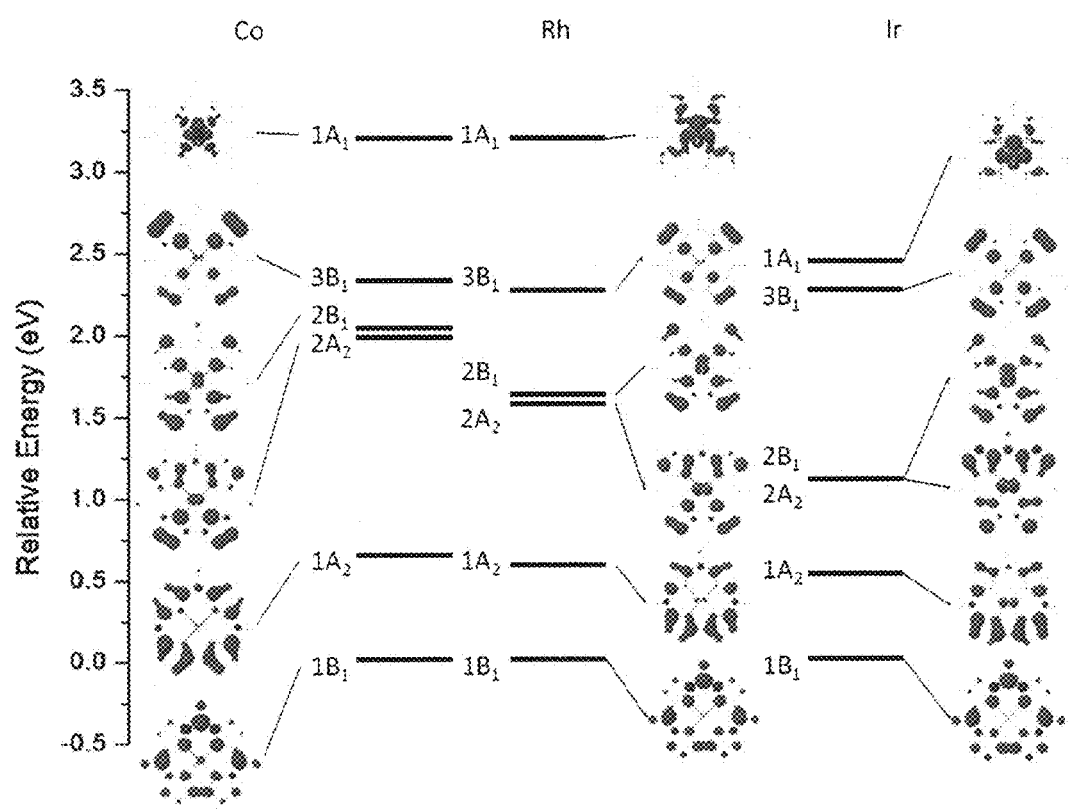
FIG. 41 is an illustration of the relative energies and spin density surfaces (isovalue=−0.002) calculated for [(tfc)M(NH$_3$)$_2$]+(M=Co, Rh, Ir).

From observation of the energy levels in both the tpfc and the tfc systems, it is apparent that the dispersion between states decreases in the order Co>Rh>Ir for each corrole system. Also, it is noteworthy that the spin density localized on the metal generally increases in the order Co<Rh<Ir for a given orbital level, except for the high-lying 1A$_1$ state, which is in the order Rh<Ir<Co. States classified as 3B$_1$ only appear in the tfc complexes because they are pushed upward in energy when the ligand is tpfc. FIG. 41 shows that the energy of the 3B$_1$ state relative to the 1B$_1$ state in the three tfc complexes is roughly the same for all three metals.

For a given metal center, the tpfc complex has smaller energy gaps between different states than the tfc complex. An exception is the gap between the nearly degenerate 2B$_1$/2A$_2$ states and the adjacent 1A$_2$ state, which is actually increased by around 0.04 eV in the tpfc case due to stabilization of the 1A$_2$ state by the pentafluorophenyl substituents on tpfc. The contraction observed between the lowest two energy states for the different corrole ligands is of a greater order than the difference brought about by changing the metal center for each corrole, presumably because the ground 1B$_1$ state is more effectively stabilized by fluorine than by pentafluorophenyl meso-substituents. [(tpfc)Ir(NH$_3$)$_2$]$^+$ has the smallest dispersion of all compounds under study, such that the energy gap between the 1B$_1$ and 1A$_2$ states is only approximately 0.15 eV in vacuum, dropping to 0.10 eV if dichloromethane solvation is added to the model. Solvation with dichloromethane decreases dispersion in a general fashion.

The calculated reduction potential of [(tpfc)Ir(NH$_3$)$_2$]$^{0/+}$ accords with the experimental value (0.53V vs. SCE) obtained via cyclic voltammetry. The computed reduction potentials of [(tpfc)M(NH$_3$)$_2$]$^{0/+}$ are 0.64, 0.67, and 0.56 V vs. SCE for M=Ir, Rh, and Co, respectively.

These DFT calculations point toward a common description of the positively charged cobalt, rhodium and iridium corroles as metal(III) complexes chelated by an oxidized, open-shell corrole macrocycle, with an unpaired electron that resides in a corrole-based B$_1$ symmetry orbital. Nevertheless, there are significant differences between the two investigated corrole ligands. For a given metal center, substitution by C$_6$F$_5$ as opposed to F at the meso-positions decreases the energetic difference between the vertically excited states of the cations. This energetic dispersion is also strongly affected by the metal, in the order of Co>Rh>Ir. The effect of the metal center and that of the meso-substituents on the energetic states of the system are largely decoupled for the rhodium and cobalt complexes. However, in the case of iridium, the excited tfc complex has degenerate energetic states (2B$_1$/2A$_2$) that become nondegenerate in the corresponding tpfc complex.

Without being limited by theory, the remarkable effects that the meso-substituents have on the energy levels of the corrole complexes may be rationalized by the following arguments: While pentafluorophenyl is a poorer electron-withdrawing group (EWG) than fluoride regarding its inductive effect, the inductive electron-withdrawing effect of the latter substituent is mitigated by its ability to donate electron density from filled fluorine 2p orbitals into the π-system of the corrole, resulting in an overall greater electron-withdrawing effect of the C$_6$F$_5$ substituent on the electronic structure of the corrole complex. This is confirmed by the fact that the bonds immediately adjacent to the fluorine are shorter than the corresponding bonds in tpfc, but the bonds farther away from the meso substituents are similar in the two corrole scaffolds. The contraction of energy dispersion implies that pentafluorophenyl is more capable of lowering the energy of those states that have a high percentage of metal character than of stabilizing those that have more corrole character. There is also a computed contraction of energy dispersion upon moving from Co to Rh to Ir, and the combined effects of having a C$_6$F$_5$ meso-substituent and the 5d metal ion in [(tpfc)Ir(NH$_3$)$_2$]$^+$ leads to a situation where the 1A$_2$ state (which has significant unpaired spin density on the metal ion) is as little as 0.1 eV above the lowest energy B$_1$ state when solvation effects are included (or 0.15 eV in vacuum).

Without being limited by theory, these observations help to explain the experimental finding of increased metal character in singly oxidized (tpfc) M$^{III}$(NH$_3$)$_2$ complexes going from Co to Rh to Ir, especially when the general trend that spin-orbit coupling increases down a Group is added to the analysis. Addition of spin-orbit effects into the DFT models would require computationally intensive valence-bond configuration interaction calculations, but given that spin-orbit coupling in 5d metals is known to be on the order of nearly half an eV, the 1A$_2$ state of [(tpfc)Ir(NH$_3$)$_2$]$^+$ could easily drop lower in energy than the 1B$_1$ corrole n-cation state. In fact, the experimental EPR spectrum of [(tpfc)Ir(NH$_3$)$_2$]$^+$ displays rhombic splitting of the g-tensor that can only arise if significant metal character is mixed into the ground state. For cobalt and rhodium, on the other hand, the energy difference between the 1A$_2$ and 1B$_1$ states is larger than for iridium and moreover spin-orbit effects on the 1A$_2$ states of the 3d and 4d corroles are likely to be negligible.

The calculated reduction potentials are very similar among the series of [(tpfc)M(NH$_3$)]$^{0/+}$ redox pairs. Considering the fact that oxidation of the M(III) corrole complexes always involves ionization of one electron from the HOMO, calculated to be a pure corrole orbital, without being limited by theory, there might be two explanations for this phenomenon. It is possible that the metal centers simply have very minor effects on the energy of the corrole-based HOMO of each complex because of poor orbital overlap, leading to the computed result that their energies (and therefore their reduction potentials) are the same regardless of the metal center. It seems that the metal center would perturb the energy levels of the corrole orbitals by providing an altered electric field regardless of orbital interaction, and that the differences among the effective electronic shielding of each metal would lead to large changes in the reduction potentials of the complexes. However, only fairly minor differences are observed among the computed reduction potentials of the three Group 9 corrole complexes, consistent with experimental data.

DFT calculations (B3LYP with Poisson-Boltzmann continuum solvation) applied to the series of Group 9 metallocorrole complexes (tpfc) M$^{III}$(NH$_3$)$_2$ (M=Co, Rh, Ir) and the corresponding cations predict a common, ligand-based one-electron oxidation in each case. Wavefunctions for the neutral M(III) molecules share a HOMO of B$_1$ symmetry with insignificant contribution from the metal, and lowest-energy wavefunctions for the cations yield spin densities with little contribution (~0.01 electron) from the metals. Calculated oxidation potentials (0.64 V, 0.67 V, and 0.56 V vs. SCE for M=Ir, Rh and Co, respectively) appear to be insensitive to the metal within the accuracy of the calculation, and are consistent with the measured oxidation potential of [(tpfc)Ir(NH$_3$)$_2$]$^{0/+}$ (0.53 V vs. SCE).

In the cations, however, vertical excitation energies to states with significant metal character decrease in the order Co>Rh>Ir, and are as low as 0.15 eV in (tpfc)Ir(NH$_3$)$_2$$^+$. Spin-orbit coupling, omitted in the calculations at this level of theory, could conceivably mix the low-lying states incorporating Ir d$_{xz}$ and d$_{yz}$ character to yield a mixed metal-ligand radical ground state as the experimental evidence suggests.

TABLE 10

Generated excited-state orbitals of (tfc)Ir$^{III}$(NH$_3$)$_2$.

| Symmetry of ionized orbital | Orbital number in Ir$^{III}$ | Resulting spin density on Ir | Resulting atomic charge on Ir | Energy relative to Ir$^{IV}$ ground state (eV) |
|---|---|---|---|---|
| B$_1$ | 107 | −0.01 | 0.88 | 0.00 |
| A$_2$ | 106 | 0.07 | 0.91 | 0.54 |
| A$_2$ | 104 | 0.24 | 0.92 | 1.21 |
| B$_1$ | 105 | 0.35 | 0.97 | 1.21 |
| B$_1$ | 103 | 0.00 | 0.89 | 2.27 |
| A$_1$ | 102 | 0.91 | 1.18 | 2.53 |

TABLE 11

Generated excited-state orbitals of (tfc)Rh$^{III}$(NH$_3$)$_2$.

| Symmetry | Orbital number | Spin density on Rh | Atomic charge on Rh | Relative energy (eV) |
|---|---|---|---|---|
| B$_1$ | 107 | −0.01 | 0.79 | 0.00 |
| A$_2$ | 106 | 0.02 | 0.81 | 0.63 |
| A$_2$ | 105 | 0.19 | 0.84 | 1.58 |
| B$_1$ | 104 | 0.22 | 0.85 | 1.62 |
| B$_1$ | 103 | 0.00 | 0.80 | 2.28 |
| A$_1$ | 99 | 0.77 | 1.05 | 3.19 |

TABLE 12

Generated excited-state orbitals of (tfc)Co$^{III}$(NH$_3$)$_2$.

| Symmetry | Orbital number | Spin density on Co | Atomic charge on Co | Relative energy (eV) |
|---|---|---|---|---|
| B$_1$ | 107 | −0.02 | 0.48 | 0.00 |
| A$_2$ | 106 | 0.00 | 0.49 | 0.67 |
| A$_2$ | 105 | 0.08 | 0.50 | 1.94 |
| B$_1$ | 104 | 0.10 | 0.50 | 2.02 |
| B$_1$ | 103 | −0.01 | 0.49 | 2.33 |
| A$_1$ | 98 | 1.16 | 0.69 | 3.19 |

TABLE 13

Generated excited-state orbitals of (tpfc)Ir$^{III}$(NH$_3$)$_2$.

| Symmetry | Orbital number | Spin density on Ir | Atomic charge on Ir | Relative energy (eV) |
|---|---|---|---|---|
| B$_1$ | 215 | −0.01 | 0.88 | 0.00 |
| A$_2$ | 214 | 0.07 | 0.90 | 0.15 |
| A$_2$ | 212 | 0.08 | 0.85 | 0.59 |
| B$_1$ | 213 | 0.38 | 0.97 | 0.86 |
| A$_1$ | 211 | 0.89 | 1.17 | 2.06 |

TABLE 14

Generated excited-state orbitals of (tpfc)Rh$^{III}$(NH$_3$)$_2$.

| Symmetry | Orbital number | Spin density on Rh | Atomic charge on Rh | Relative energy (eV) |
|---|---|---|---|---|
| B$_1$ | 215 | −0.01 | 0.79 | 0.00 |
| A$_2$ | 214 | 0.02 | 0.80 | 0.24 |
| A$_2$ | 213 | 0.21 | 0.84 | 1.23 |
| B$_1$ | 212 | 0.24 | 0.86 | 1.27 |
| A$_1$ | 202 | 0.75 | 1.04 | 2.71 |

TABLE 15

Generated excited-state orbitals of (tpfc)Co$^{III}$(NH$_3$)$_2$.

| Symmetry | Orbital number | Spin density on Co | Atomic charge on Co | Relative energy (eV) |
|---|---|---|---|---|
| B$_1$ | 215 | −0.02 | 0.47 | 0.00 |
| A$_2$ | 214 | 0.00 | 0.48 | 0.27 |
| A$_2$ | 213 | 0.10 | 0.48 | 1.63 |
| B$_1$ | 212 | 0.12 | 0.49 | 1.71 |
| A$_1$ | 201 | 1.13 | 0.66 | 2.74 |

Figure 2:
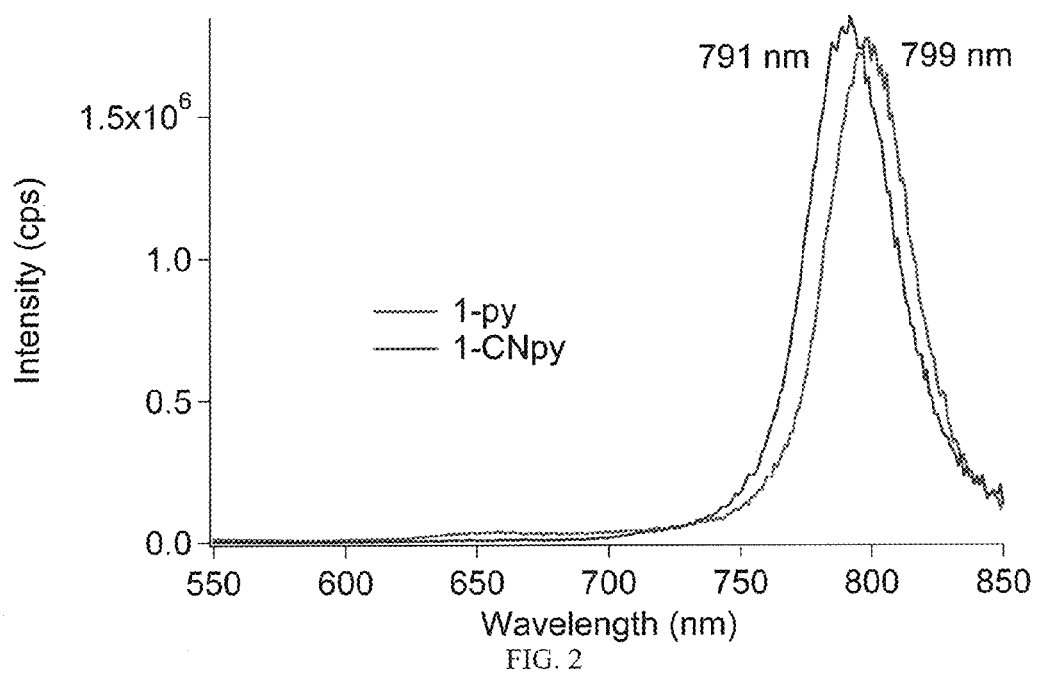
FIG. 2 is a graph of emission (phosphorescence) spectra of 1-py and 1-CNpy, in $CH_2Cl_2$ solutions at room temperature.
Figure 3:
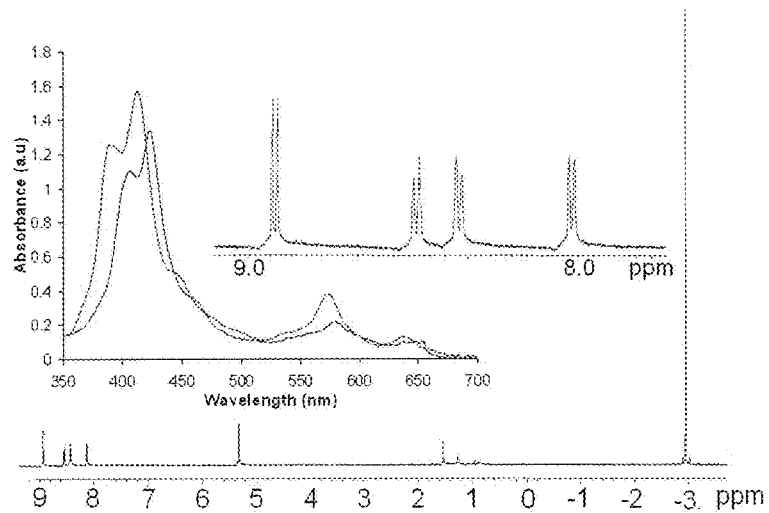
FIG. 3 is a graph of a $^1H$ nuclear magnetic resonance (NMR) spectrum of 1 in $CD_2Cl_2$ and UV-vis spectra of 1 (red) and 2 (blue) in $CH_2Cl_2$; inset is a graph of the β-pyrrole proton resonances.
Figure 4:
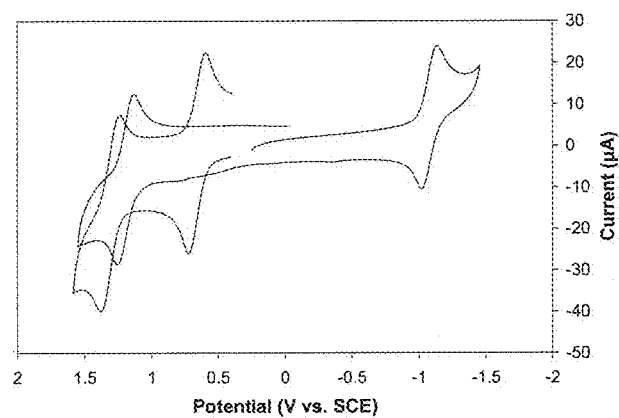
FIG. 4 is a graph of cyclic voltammogram (CV) traces of 1-Ir(tma)$_2$ (in red) and 2-Ir(tma)$_2$ (in blue) in $CH_2Cl_2$ solution at 23° C.
Figure 5:
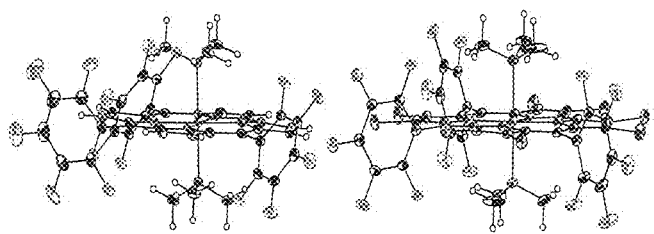
FIG. 5 is an illustration of the X-ray structures of 1 (left) and 2 (right), illustrating: 50% probability displacement ellipsoids; and average bond distances of: Ir—N (equatorial) 1.965 (9) [1-Ir(tma)$_2$], 1.974(3) [2-Ir(tma)$_2$] and Ir—N (axial) 2.185 (9) [1-Ir(tma)$_2$], 2.189(3) [2-Ir(tma)$_2$].
Figure 7:
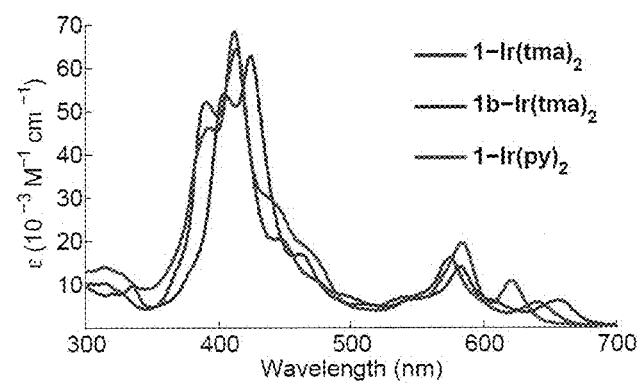
FIG. 7 is a graph of UV-vis spectra of Ir(III) corroles in toluene solution at 298 K.
Figure 8:
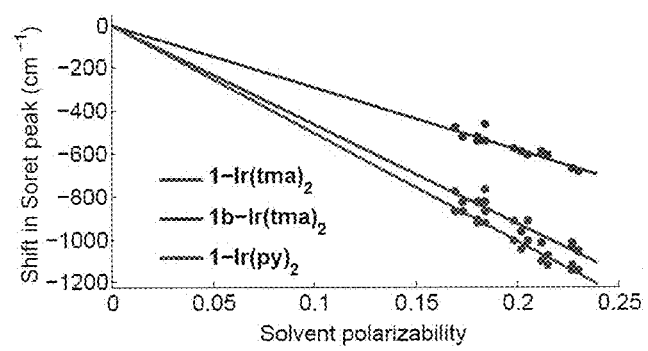
FIG. 8 is a graph illustrating the shift in the lower energy Soret component as a function of solvent polarizability (the sodium D line at 20° C. was used for n).
Figure 9:
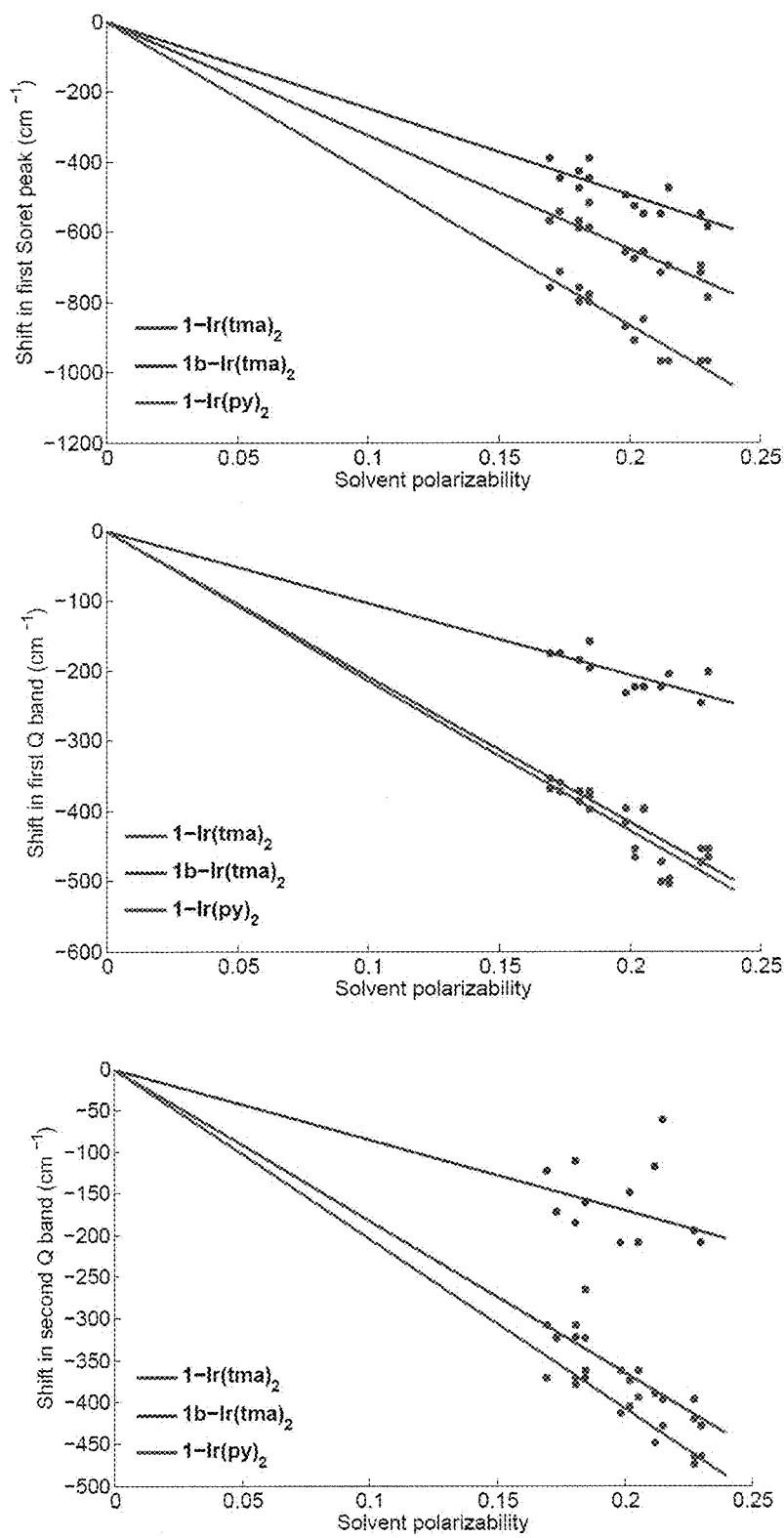
FIG. 9 is a graph illustrating spectral shifts of the absorption maxima as a function of solvent polarizability for the weaker Soret and both Q absorption bands in various solvents.
Figure 10:
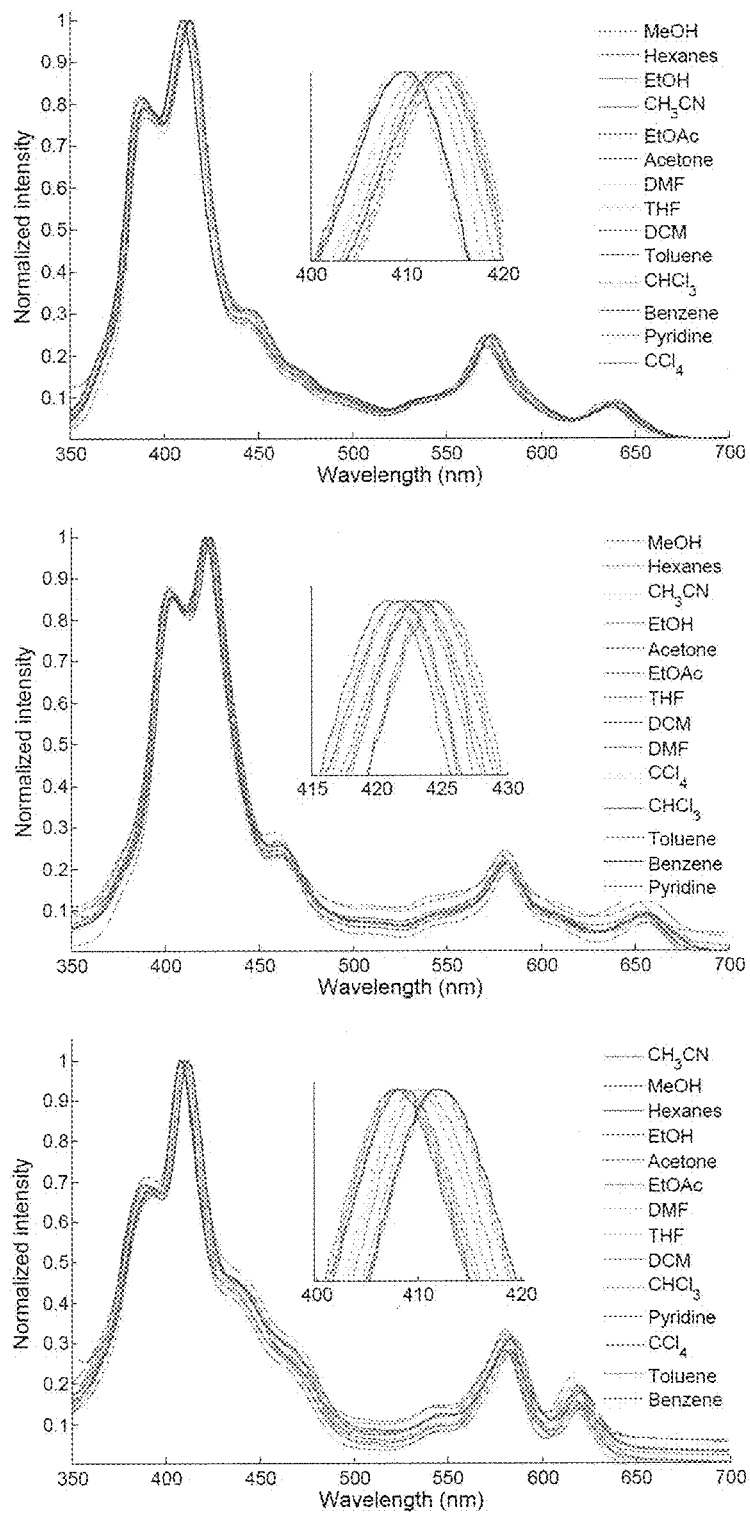
FIG. 10 is a graph of UV-vis absorption spectra of (top to bottom): 1-Ir(tma)$_2$, 1b-Ir(tma)$_2$, 1-Ir(py)$_2$ at room temperature in a broad range of solvents; the inset is a graph of the Soret band used for the calculation of the solvatochromic shifts discussed herein.
Figure 11:
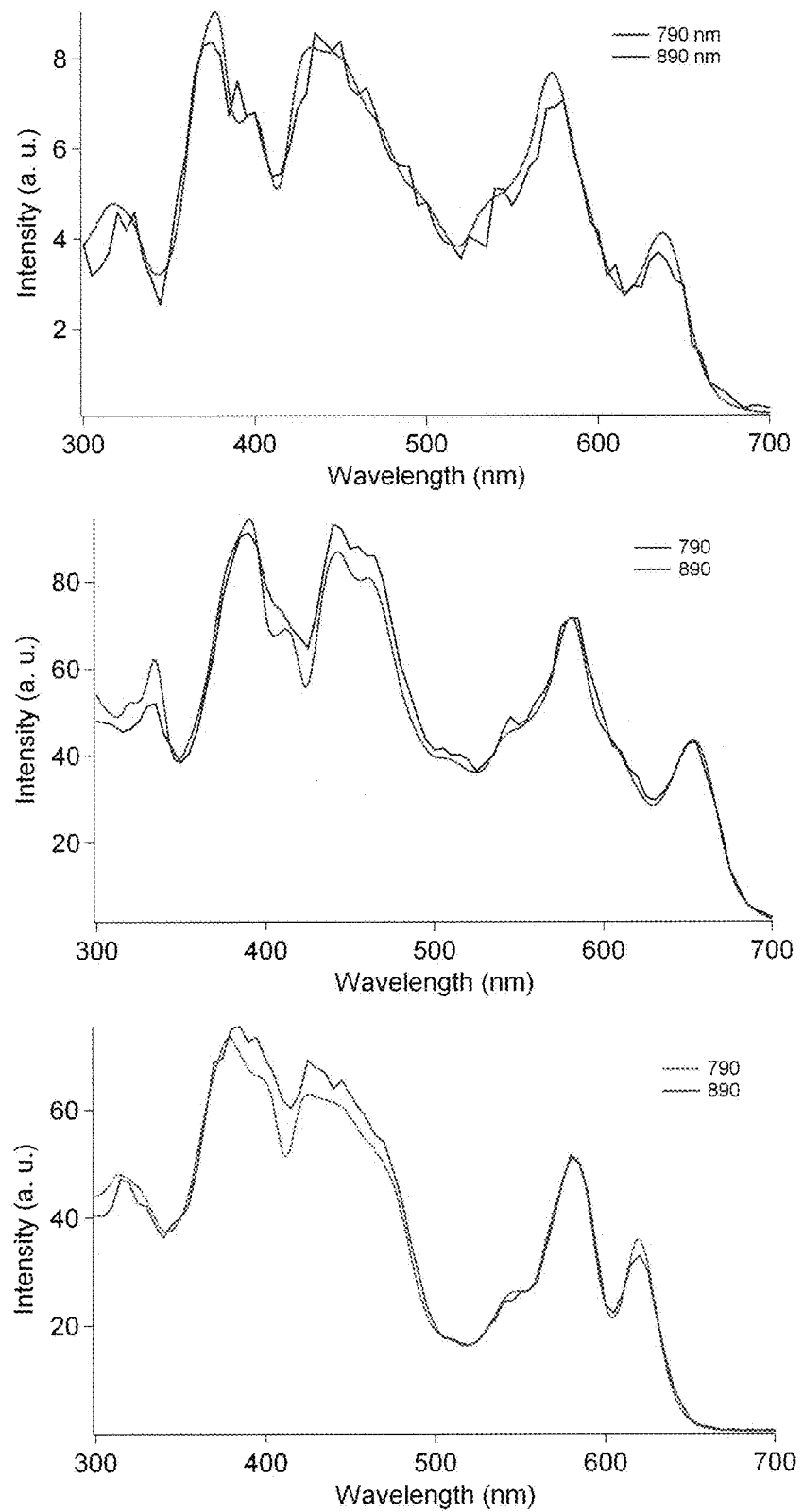
FIG. 11 is a graph of normalized excitation profiles of (top to bottom): 1-Ir(tma)$_2$, 1b-Ir(tma)$_2$, 1-Ir(py)$_2$ monitored at emission wavelengths of 790 and 890 nm.
Figure 12:
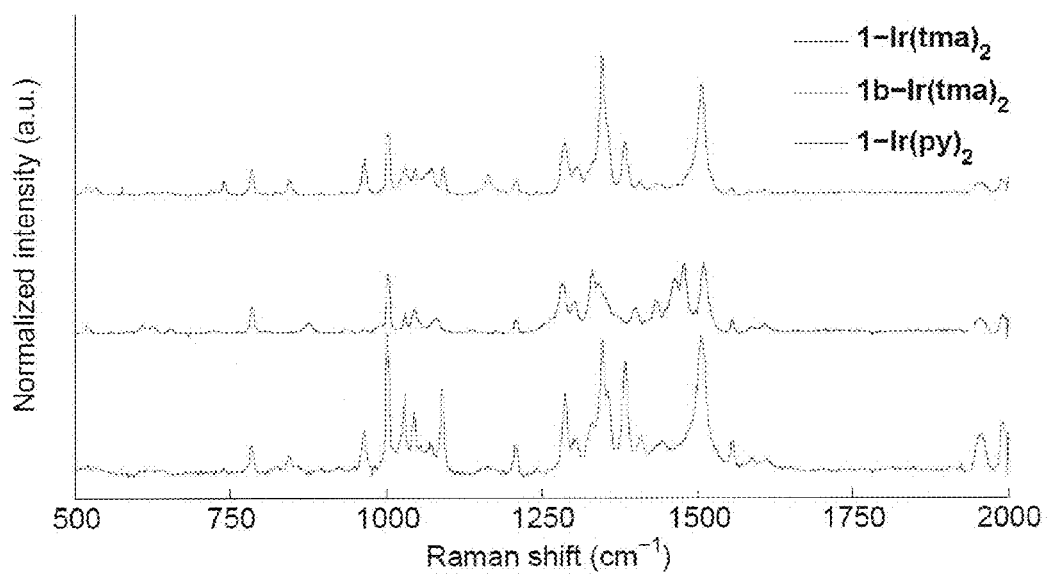
FIG. 12 is a graph of Raman spectra of 1-Ir(tma)$_2$, 1b-Ir(tma)$_2$, 1-Ir(py)$_2$; sample excitation into the Soret was achieved with the 488 nm line of an argon ion laser.
Figure 20:
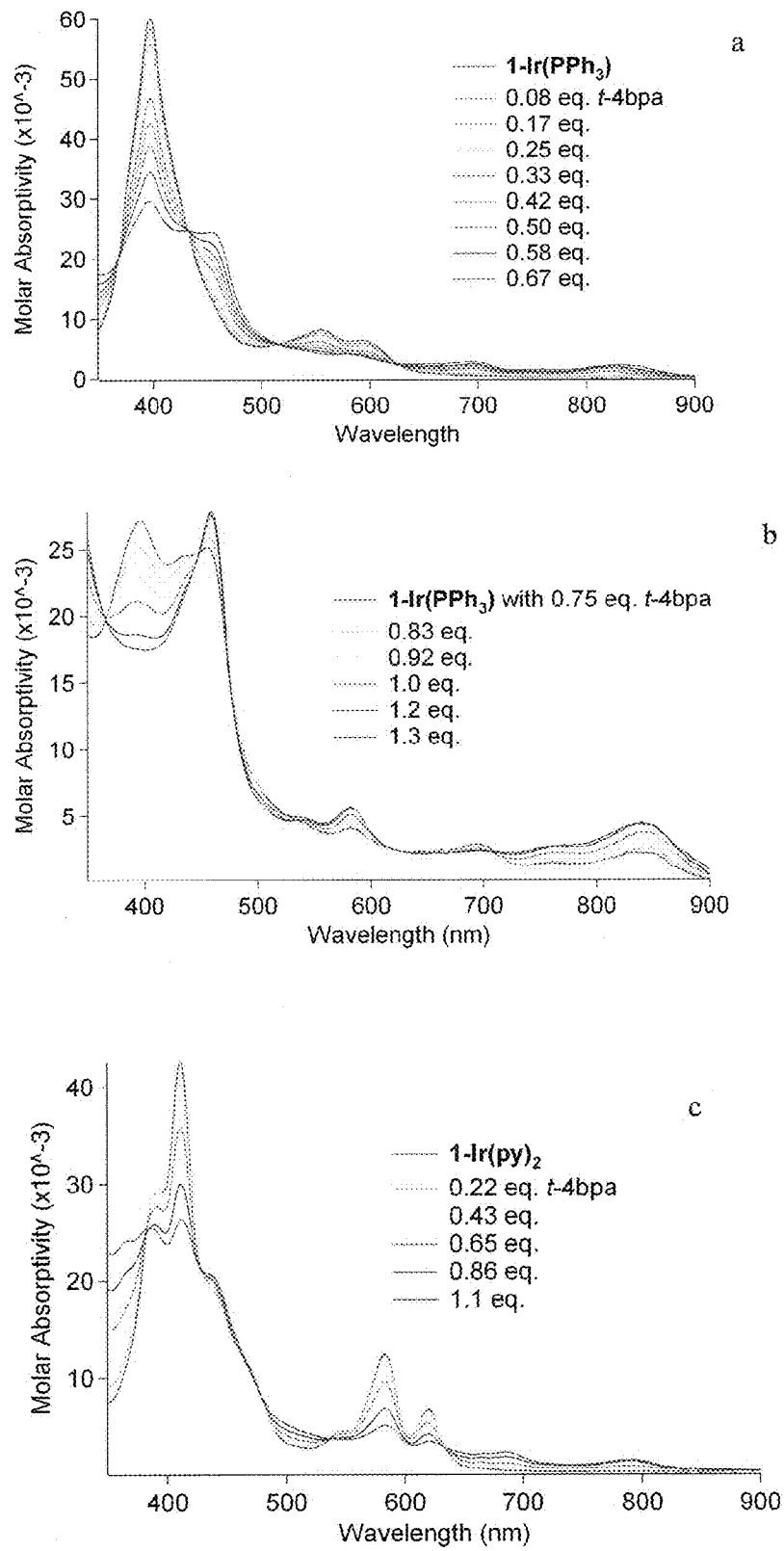
FIG. 20 is a series of graphs illustrating changes in the electronic spectra indicating oxidation by t-4bpa in CH$_2$Cl$_2$ of (from top): a) 1-Ir(PPh$_3$)$_2$, up to its first oxidation product; b) 1-Ir(PPh$_3$)$_2$, starting after its first oxidation product is formed; and c) 1-Ir(py)$_2$.
Figure 21:
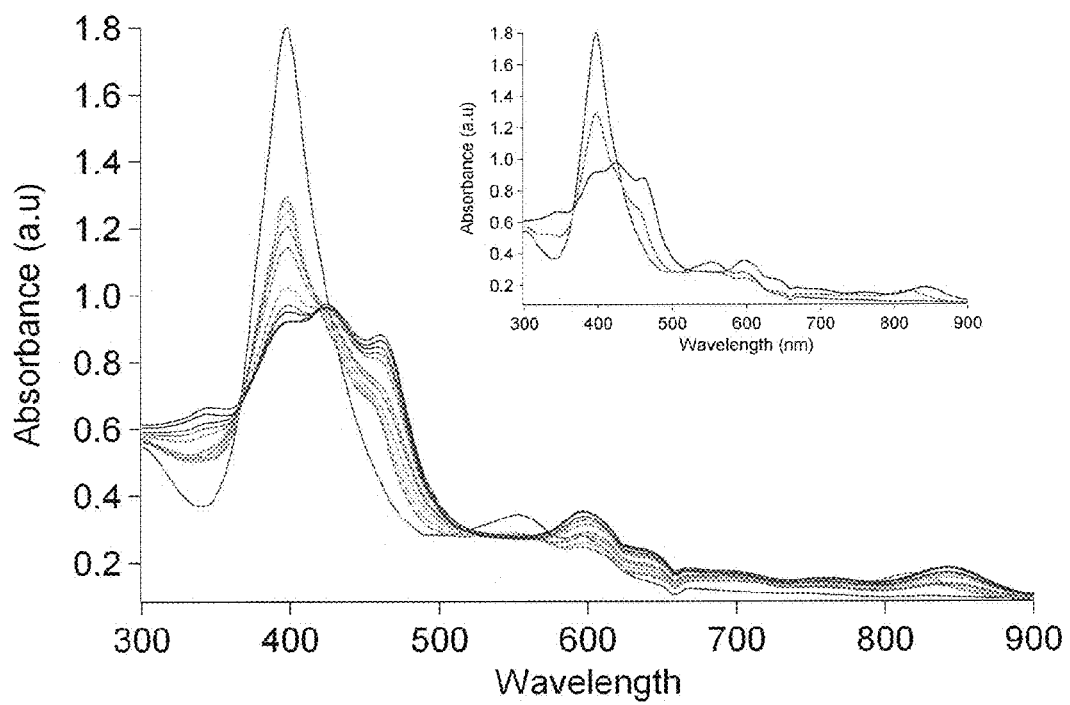
FIG. 21 is a graph of spectroelectrochemical results for a CH$_2$Cl$_2$ solution of 1-Ir(PPh$_3$) at 1.0 V vs. Ag/AgCl; the inset is a graph of the spectra of the starting material (red), the first oxidation product (green), and the second oxidation product (blue).
Figure 23:
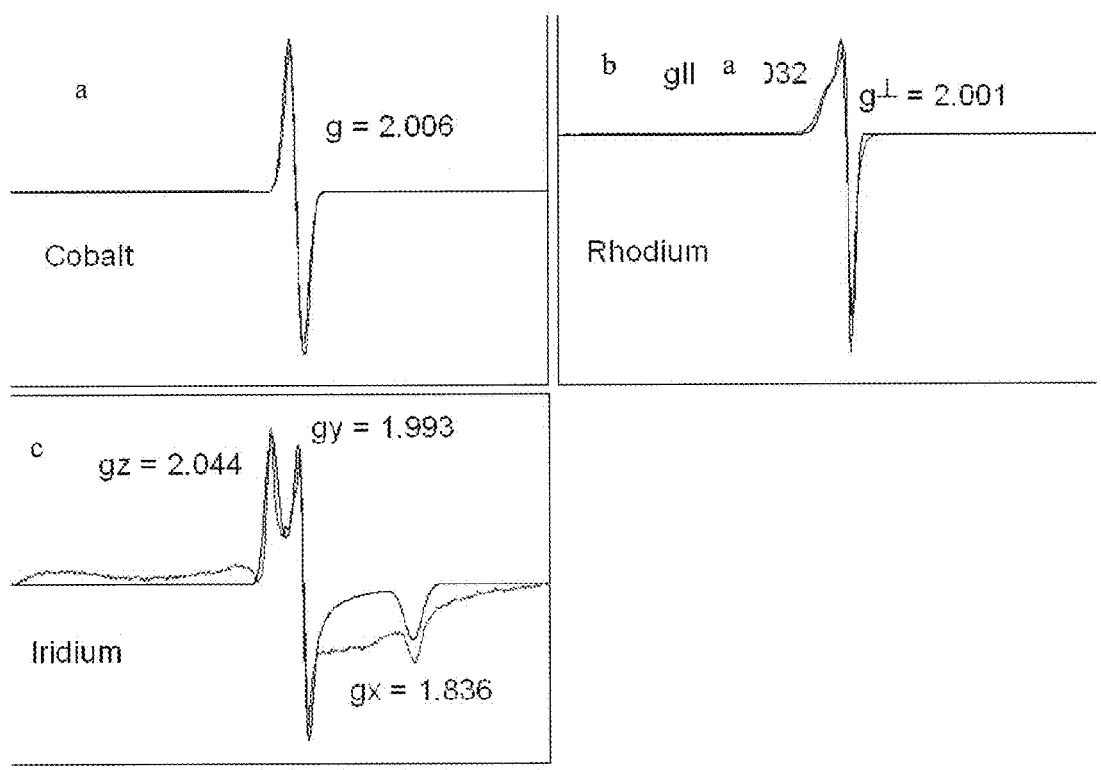
FIG. 23 is a graph of electron paramagnetic resonance (EPR) spectra taken at 20 K in frozen toluene solutions (with small amounts of CH$_2$Cl$_2$ to solvate t-4bpa for the top two spectra), of the chemically oxidized forms of (clockwise from top left): a) 1-Co(py)$_2$; b) 1-Rh(py)$_2$; and c) 1-(py)$_2$; where the blue traces are the experimental spectra and the black traces are simulations performed using the SPINCOUNT package.
Figure 24:
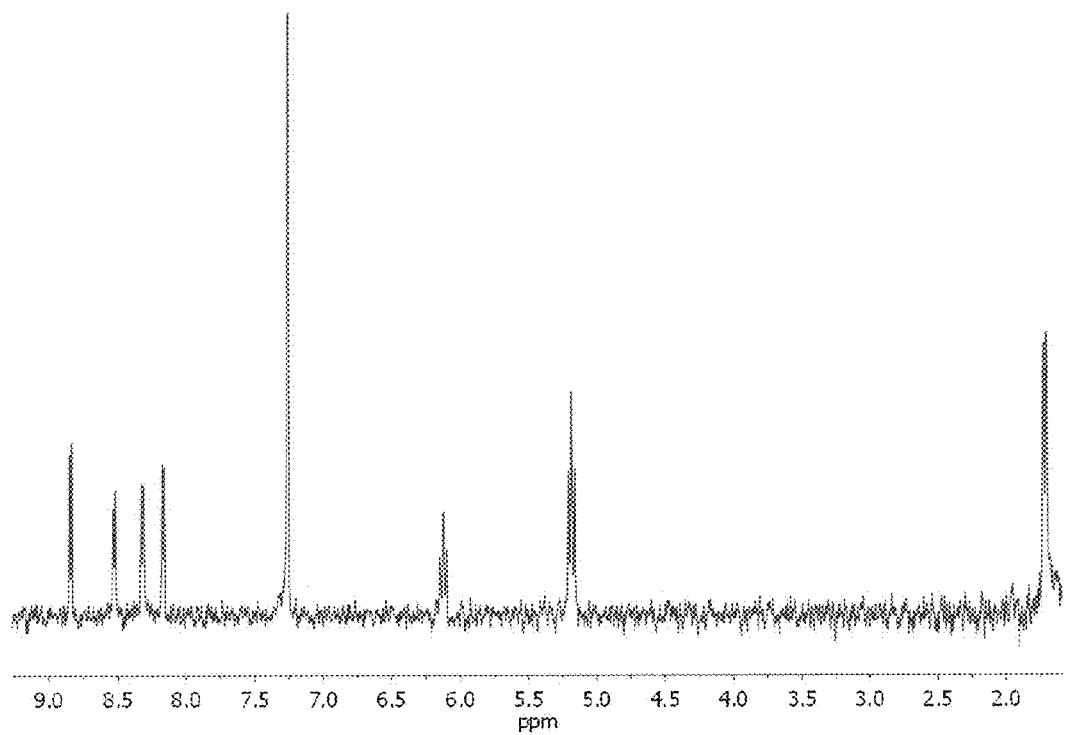
FIG. 24 is a graph of a 300 MHz $^1$H NMR spectrum of 1-Ir(py)$_2$.
Figure 25:
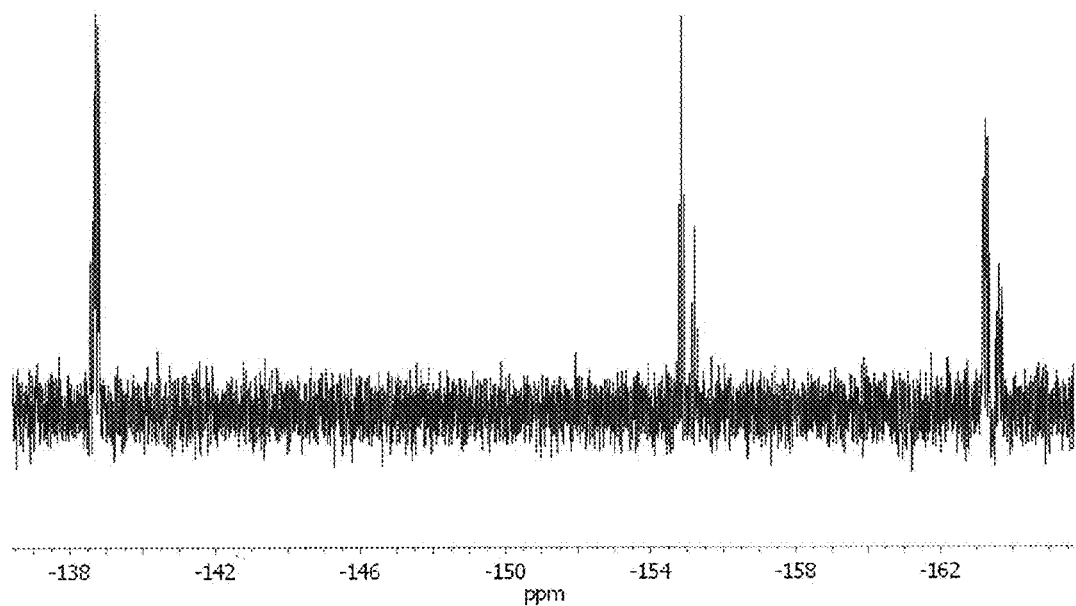
FIG. 25 is a graph of a 300 MHz $^{19}$F NMR spectrum of 1-Ir(py)$_2$.
Figure 26:
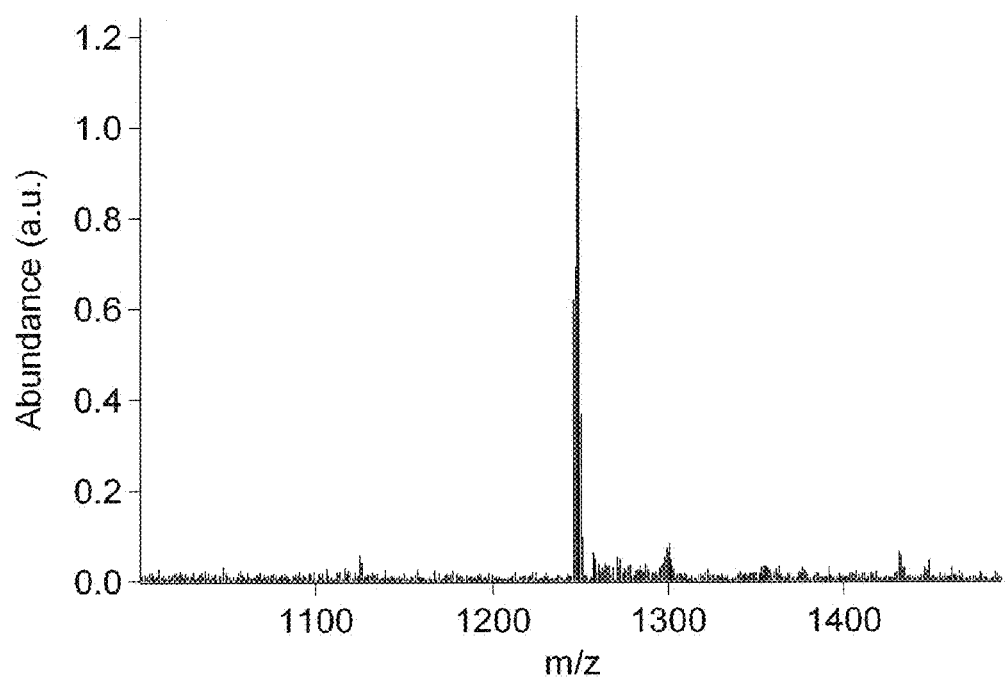
FIG. 26 is a graph of an electrospray ionization mass spectrometry (ESI-MS) trace for 1-Ir(py)$_2$.
Figure 27:
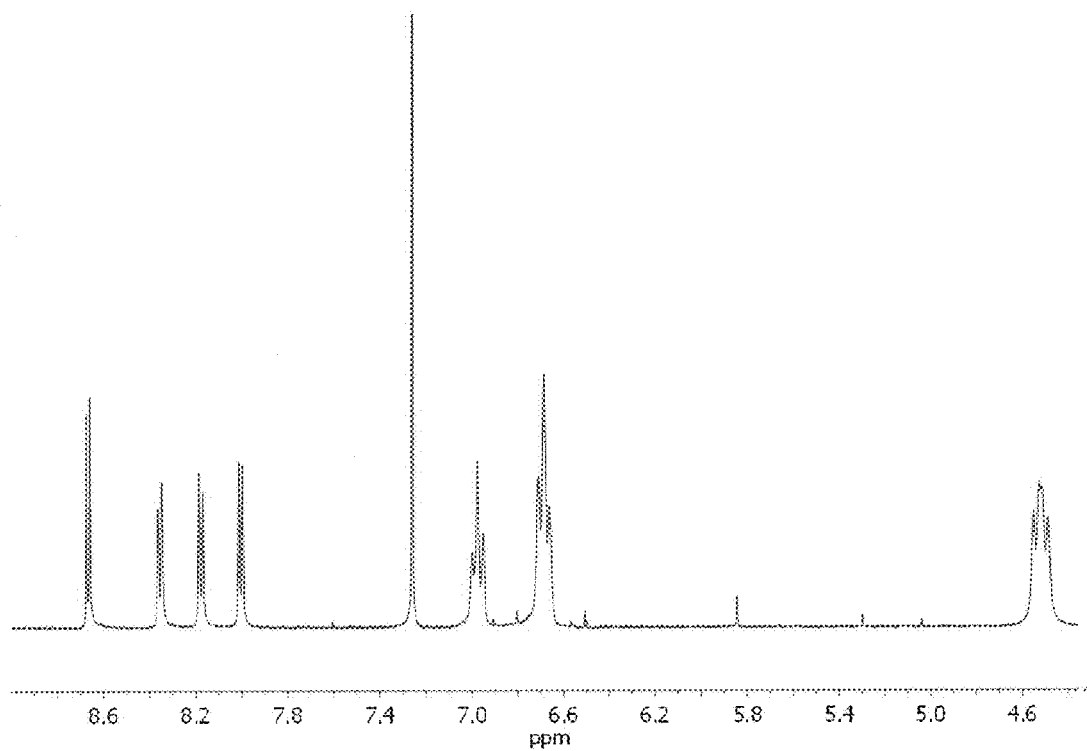
FIG. 27 is a graph of a 300 MHz $^1$H NMR spectrum of 1-Ir(PPh$_3$).
Figure 28:
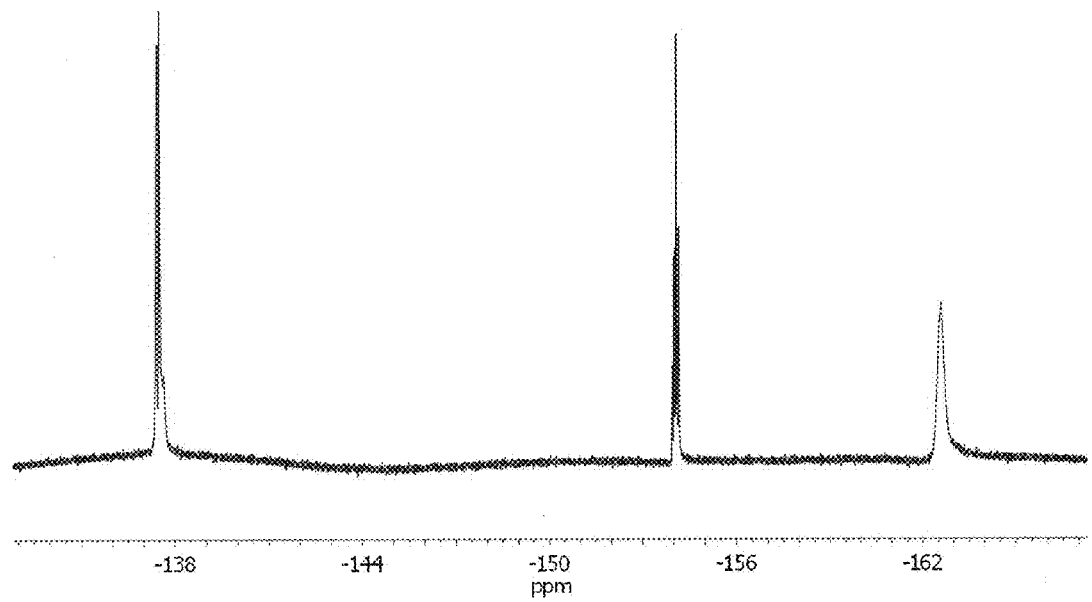
FIG. 28 is a graph of a 300 MHz $^{19}$F NMR spectrum of 1-Ir(PPh$_3$).
Figure 29:
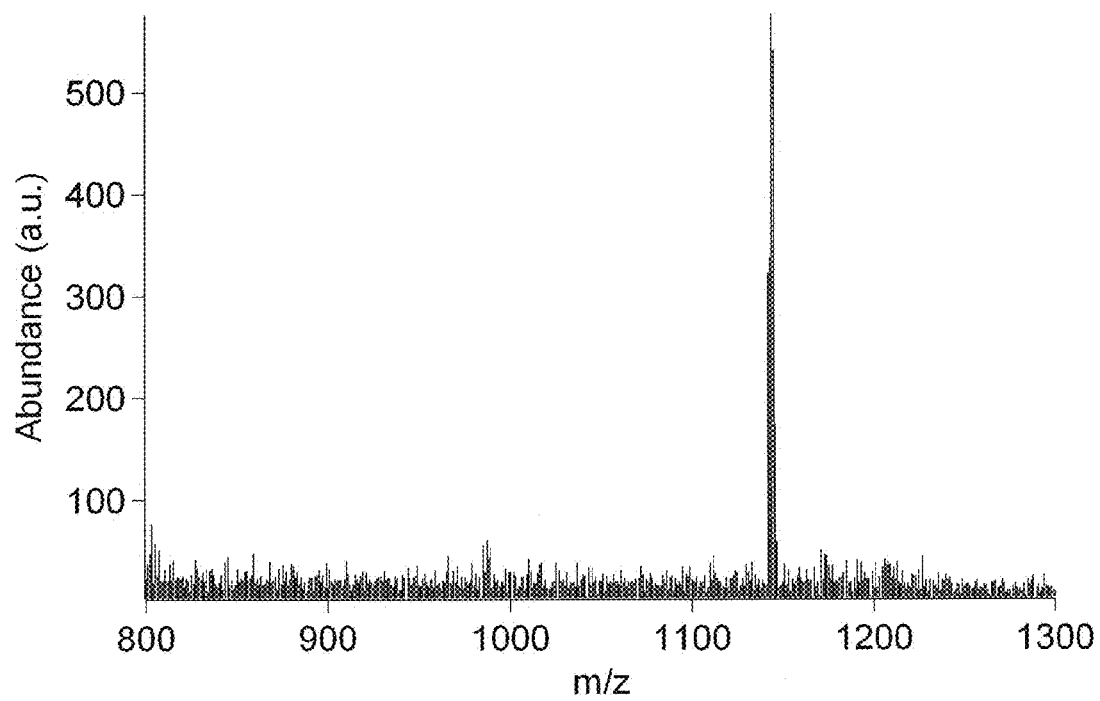
FIG. 29 is a graph of an ESI-MS trace for 1-Ir(PPh$_3$).
Figure 30:
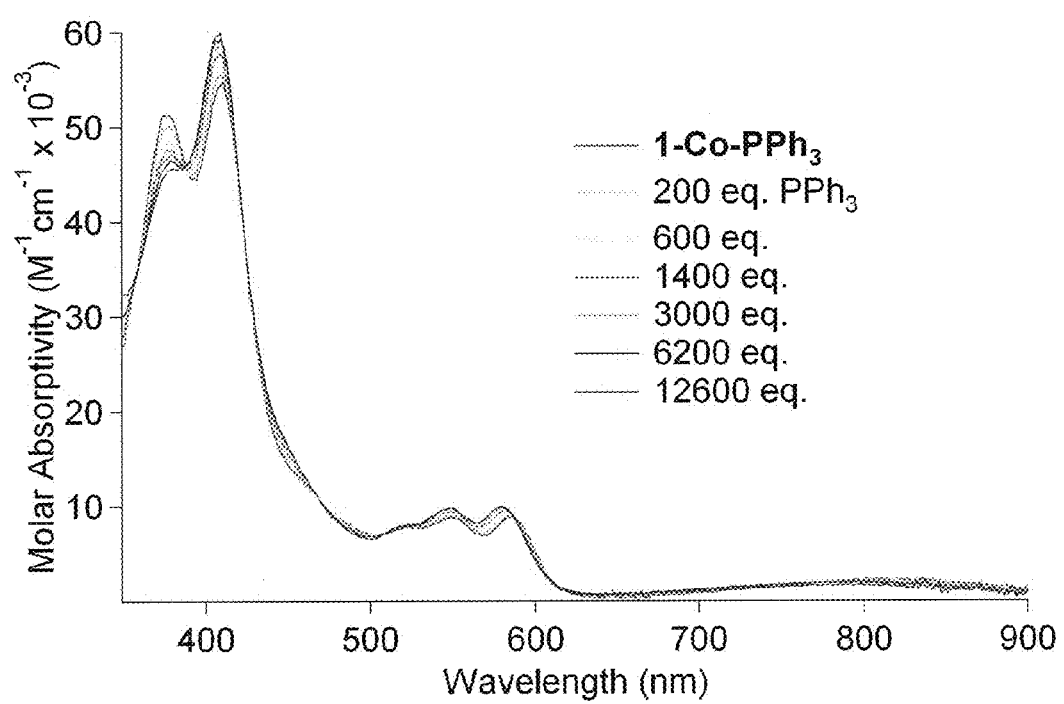
FIG. 30 is a graph illustrating changes to the electronic absorption spectrum of 1-Co(PPh$_3$) in CH$_2$Cl$_2$ upon addition of excess PPh$_3$.
Figure 32:
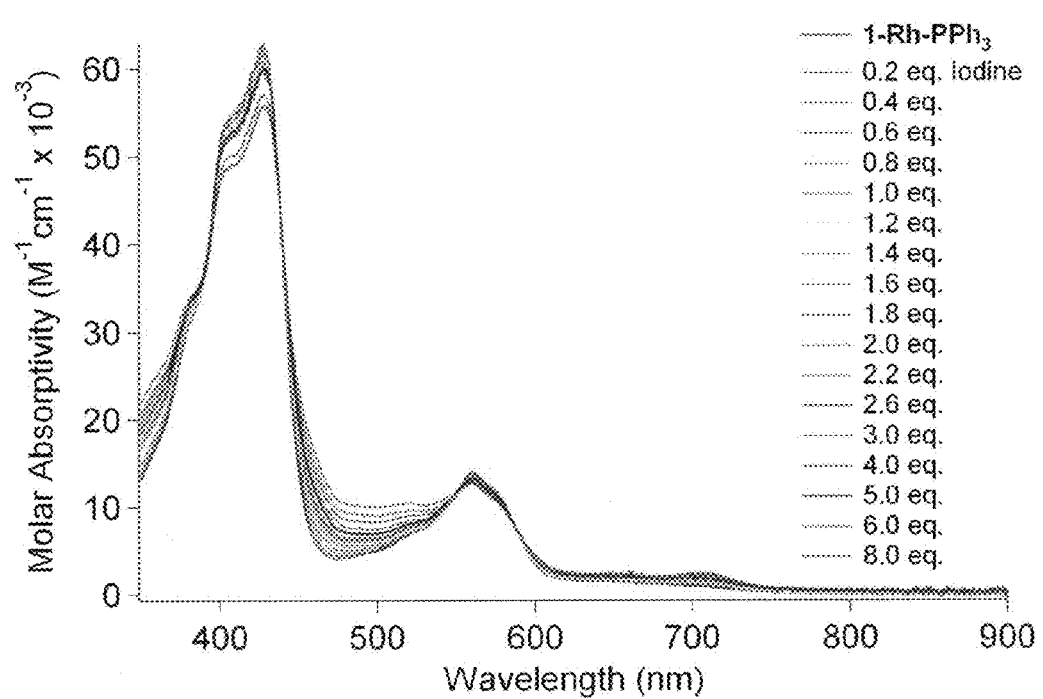
FIG. 32 is a graph illustrating changes to the electronic absorption spectrum of 1-Rh(PPh$_3$) in CH$_2$Cl$_2$ upon reaction with iodine.
Figure 33:
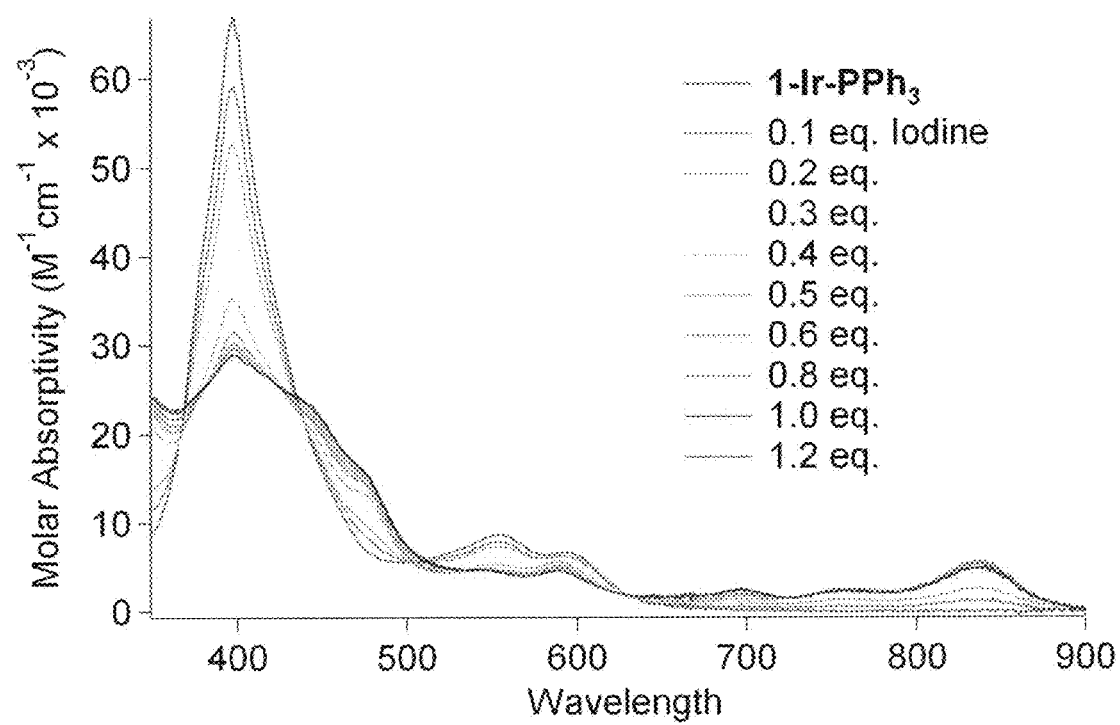
FIG. 33 is a graph illustrating changes to the electronic absorption spectrum of 1-Ir(PPh$_3$) in CH$_2$Cl$_2$ upon reaction with iodine.
Figure 34:
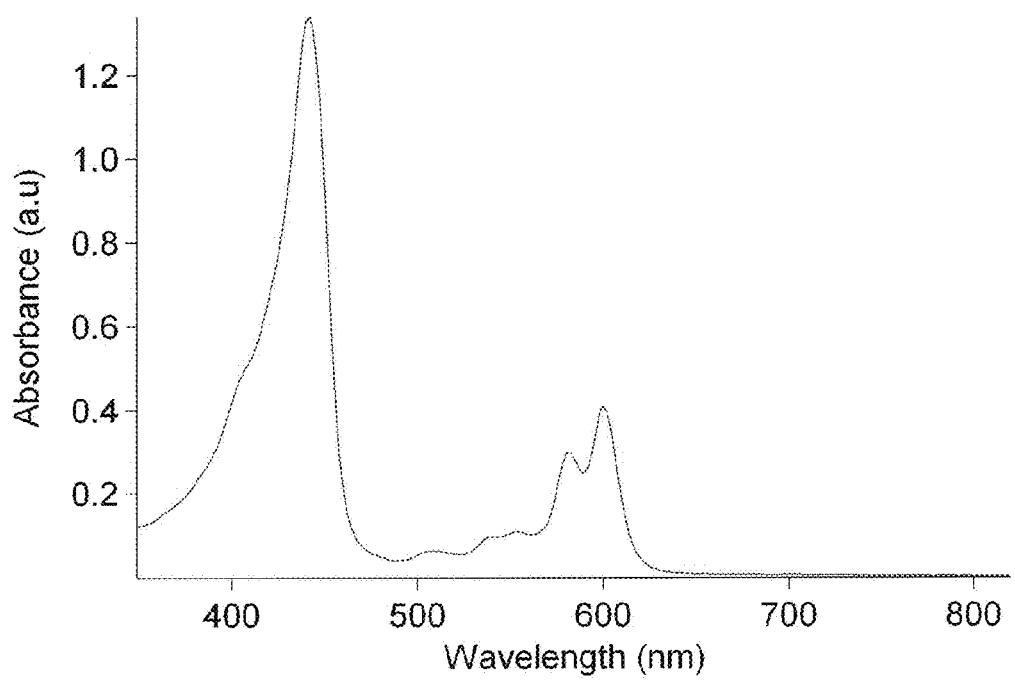
FIG. 34 is a graph of the electronic absorption spectrum of 1-Co(py)$_2$ in 5% pyridine/CH$_2$Cl$_2$.
Figure 35:
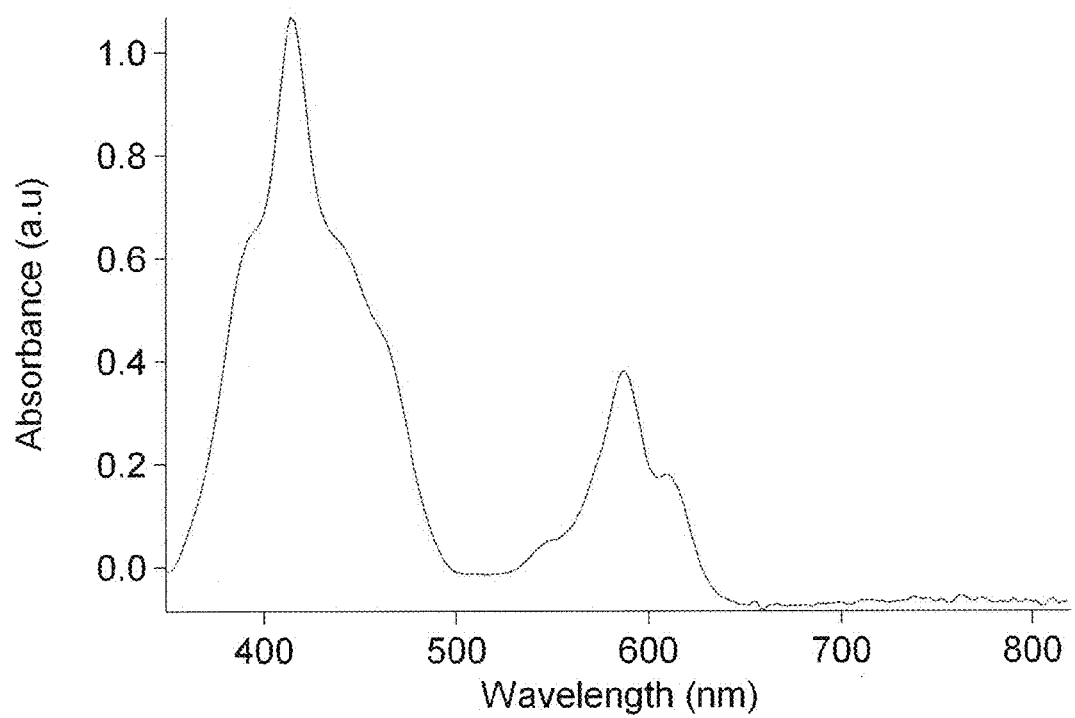
FIG. 35 is a graph of the electronic absorption spectrum of 1-Ir(PPh$_3$) in 5% pyridine/CH$_2$Cl$_2$, illustrating that 1-Ir(PPh$_3$) is not converted to 1-Ir(py)$_2$ under these conditions.
Figure 36:
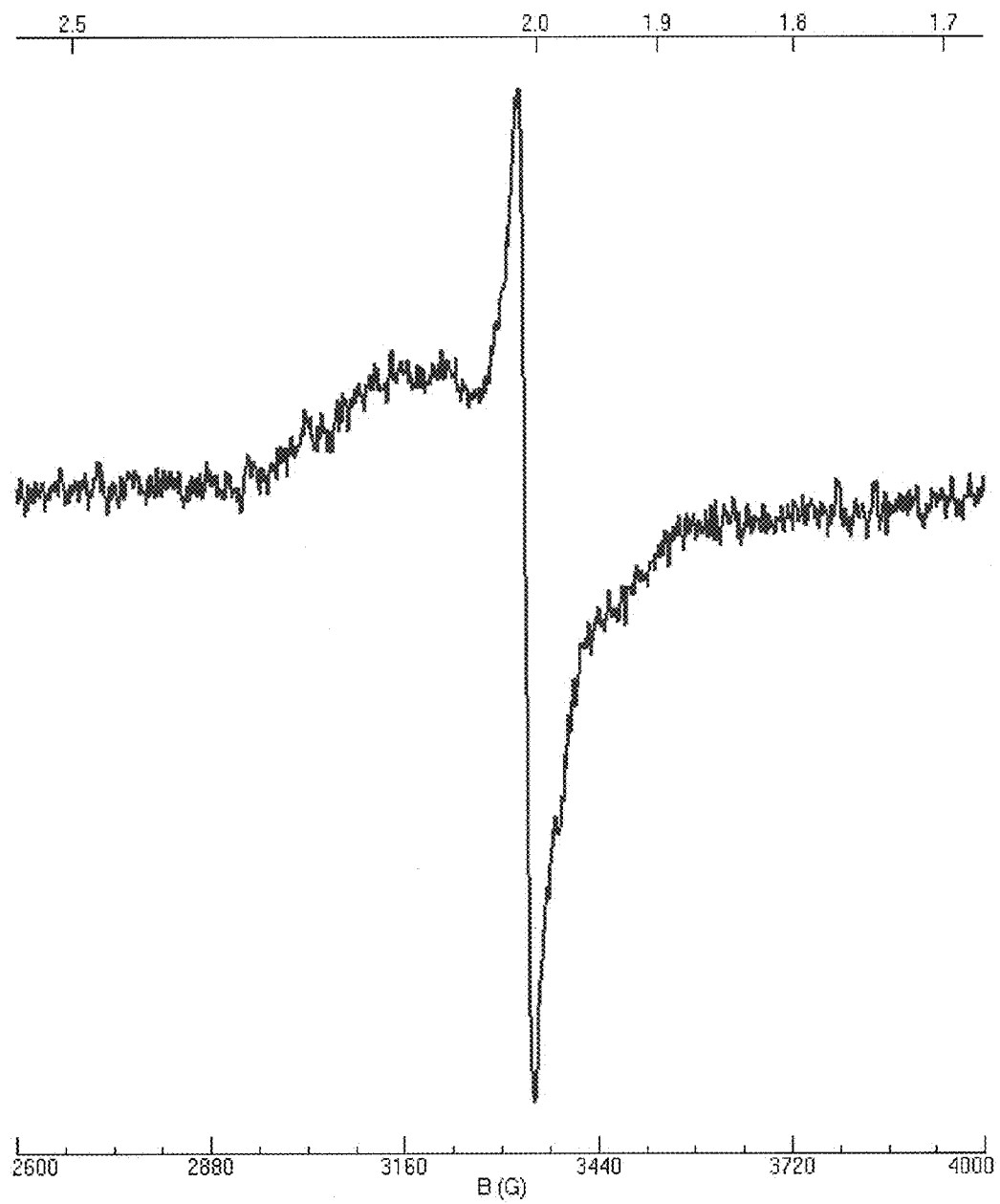
FIG. 36 is a graph of an EPR spectrum of singly oxidized 1-Co(PPh$_3$), taken at 20 K in frozen toluene.
Figure 37:
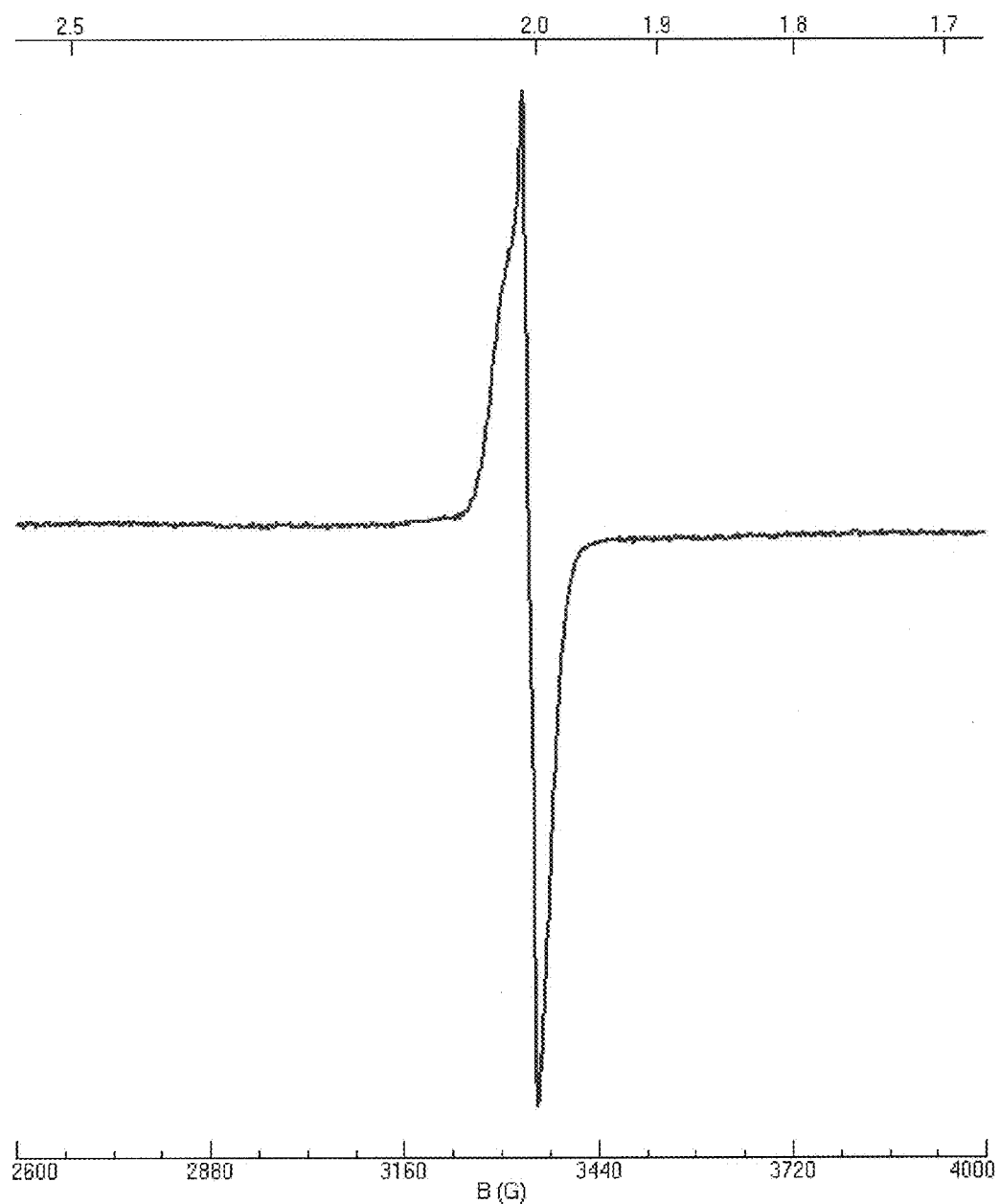
FIG. 37 is a graph of an EPR spectrum of singly oxidized 1-Rh(PPh$_3$), taken at 20 K in frozen toluene.
Figure 42:
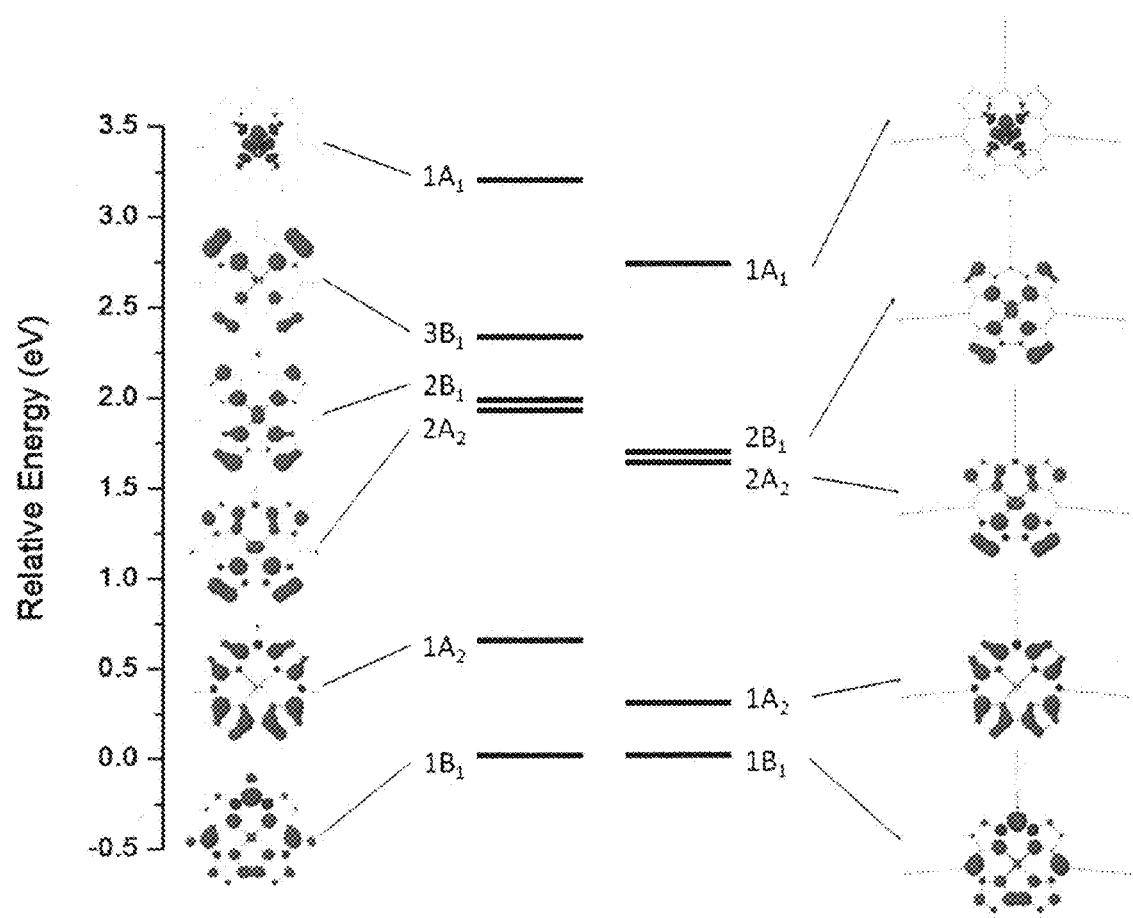
FIG. 42 is an illustration of orbital drawings and energies for [(tfc)Co(NH3)2]+ and [(tpfc)Co(NH3)2]+.
Figure 43:
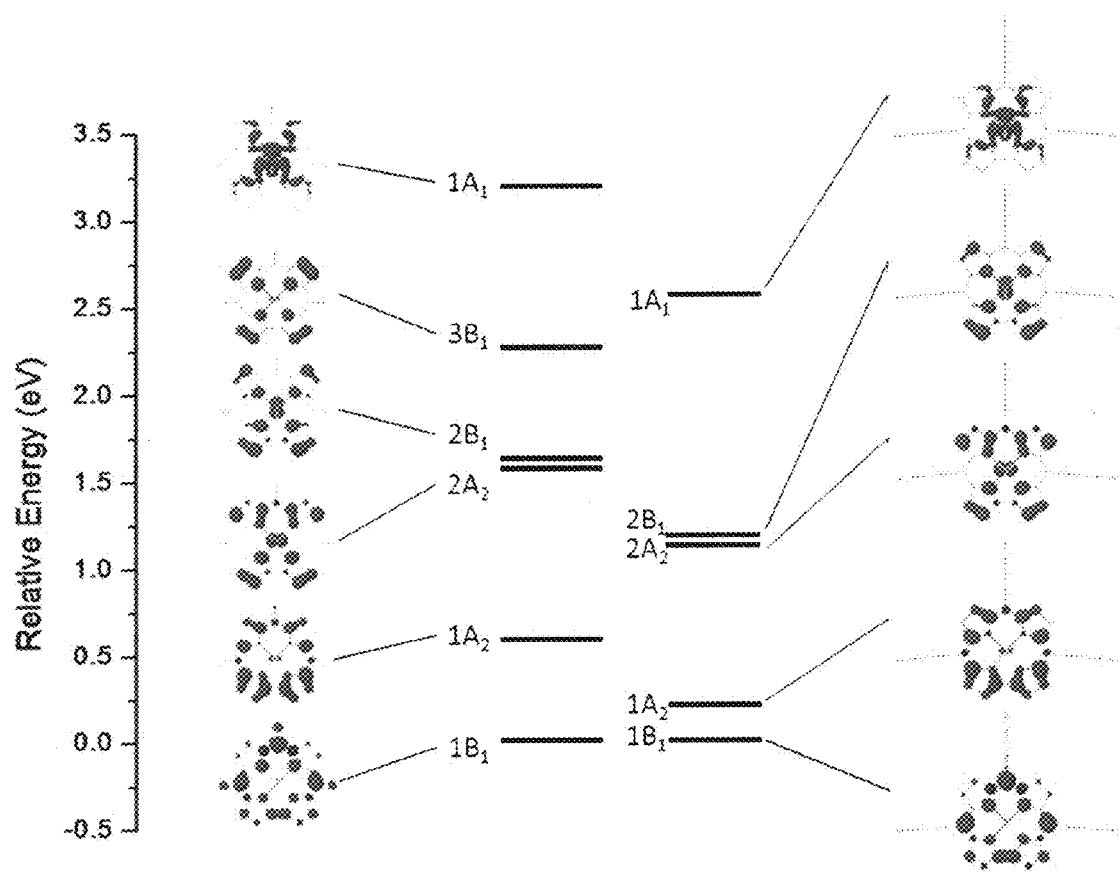
FIG. 43 is an illustration of orbital drawings and energies for [(tfc)Rh(NH3)2]+ and [(tpfc)Rh(NH3)2]+.
Figure 44:
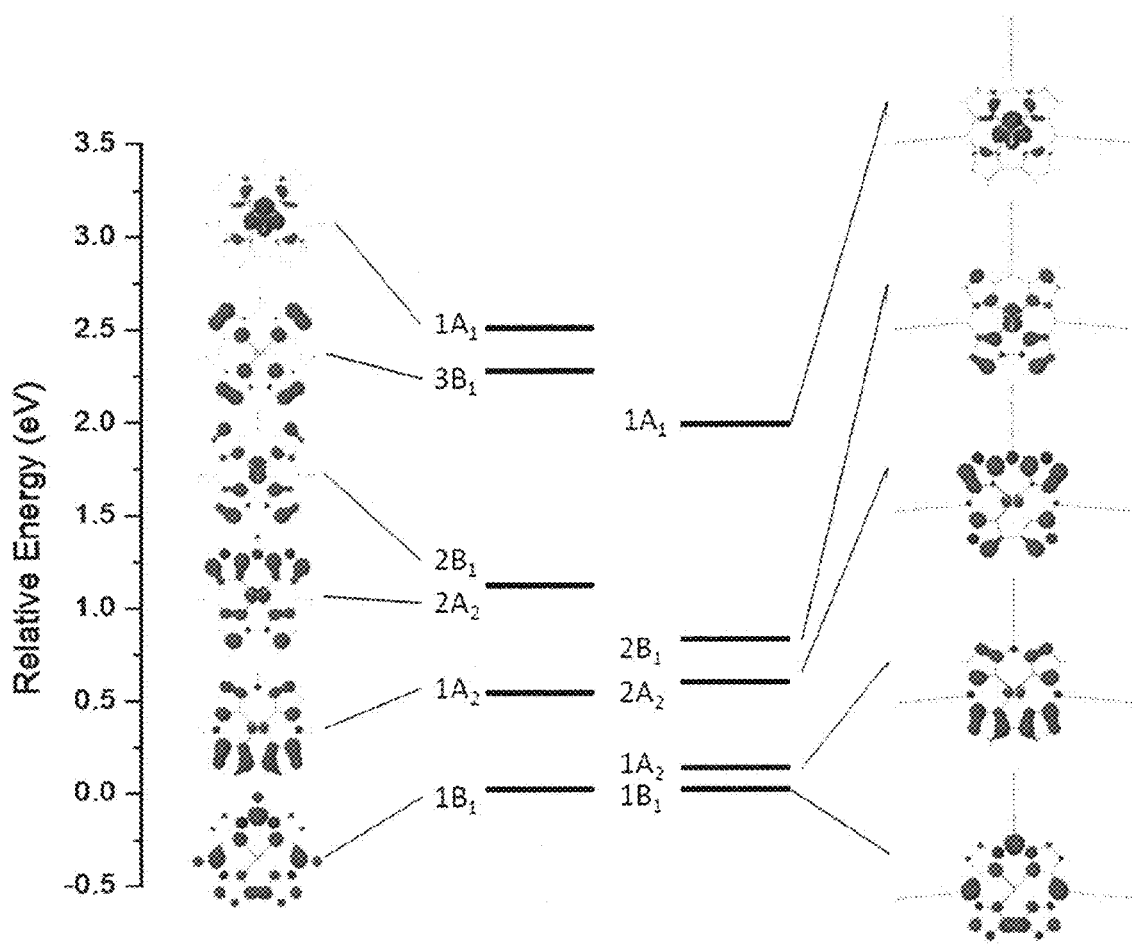
FIG. 44 is an illustration of orbital drawings and energies for [(tfc)Ir(NH3)2]+ and [(tpfc)Ir(NH3)2]+.
Figure 45:
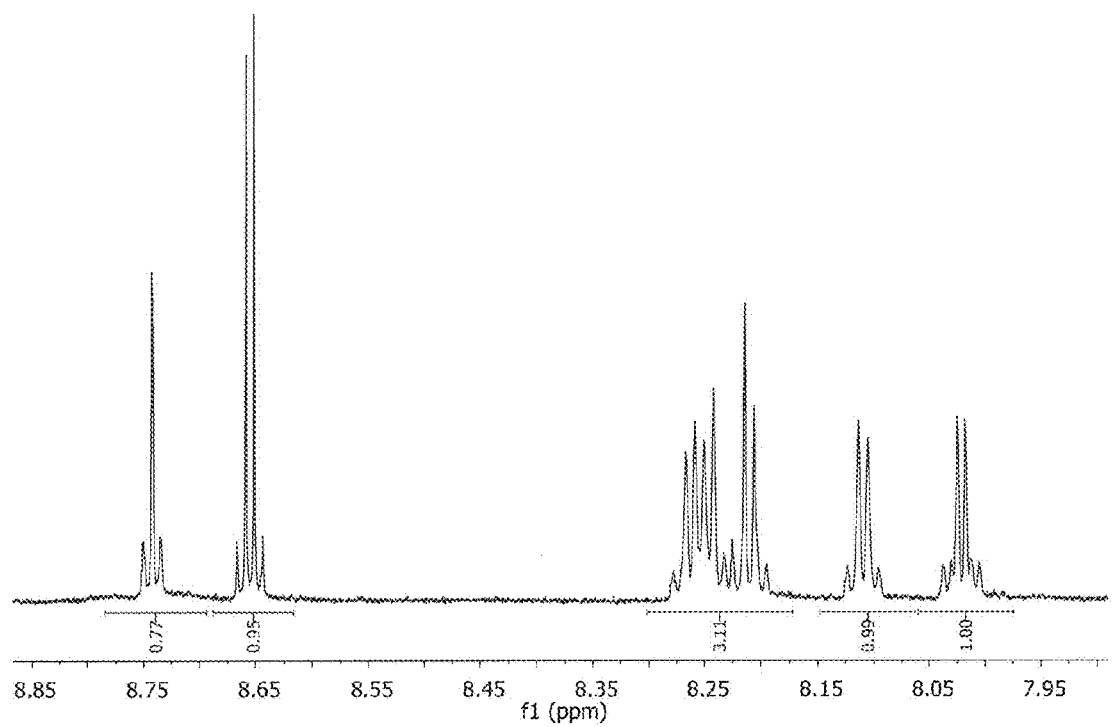
FIG. 45 is a graph of a $^1$H NMR spectrum of a platinum containing metallocorrole according to embodiments of the present invention.
Figure 46:
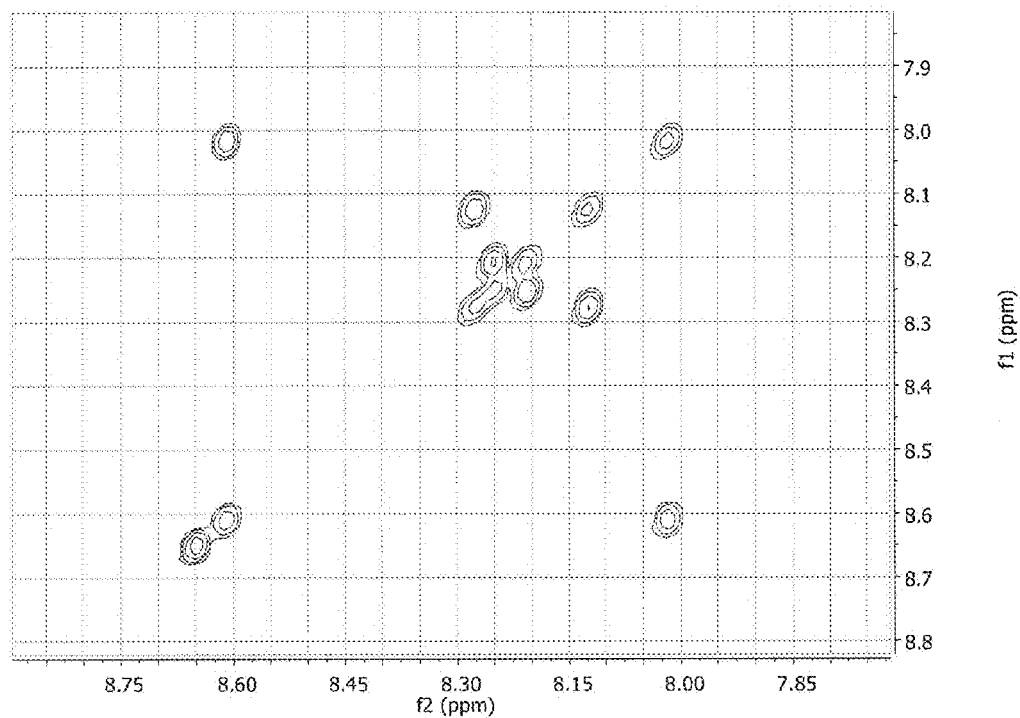
FIG. 46 is a graph of a correlation spectroscopy (COSY) $^1$H NMR spectrum of a platinum containing metallocorrole according to embodiments of the present invention.

FIGS. 1-46 show illustrations of emission spectra, nuclear magnetic resonance (NMR) spectra, cyclic voltammograms, x-ray diffraction crystallographic structures, UV-vis spectra, normalized excitation profiles, Raman spectra, spectroelectrochemical results, electron paramagnetic resonance (EPR) spectra, electrospray ionization mass spectrometry (ESI-MS) traces, atom numbering schemes, molecular orbital surfaces, relative energies and spin density surfaces, and orbital drawings and energies of the various compounds discussed herein. In particular, FIGS. 1 and 2 are graphs of emission (phosphorescence) spectra of 1-tma, 2-tma, 1-py and 1-CNpy in CH$_2$Cl$_2$ solutions at room temperature. FIG. 3 is a graph of a $^1$H nuclear magnetic resonance (NMR) spectrum of 1 in CD$_2$Cl$_2$ and UV-vis spectra of 1 (red) and 2 (blue) in CH$_2$Cl$_2$; inset is a graph of the β-pyrrole proton resonances. FIG. 4 is a graph of cyclic voltammogram (CV) traces of 1-Ir(tma)$_2$ (in red) and 2-Ir(tma)$_2$ (in blue) in CH$_2$Cl$_2$ solution at 23° C. FIG. 5 is an illustration of the X-ray structures of 1 (left) and 2 (right), illustrating: 50% probability displacement ellipsoids; and average bond distances of Ir—N (equatorial) 1.965 (9) [1-Ir(tma)$_2$], 1.974(3) [2-Ir(tma)$_2$] and Ir—N (axial) 2.185 (9) [1-Ir(tma)$_2$], 2.189(3) [2-Ir(tma)$_2$]. FIG. 6 is a graph of emission spectra of Ir(III) corroles in degassed toluene solution (λ$_{ex}$=496.5 nm); a. was measured at 298 K; b. was measured at 77 K. FIG. 7 is a graph of UV-vis spectra of Ir(III) corroles in toluene solution at 298 K. FIG. 8 is a graph illustrating the shift in the lower energy Soret component as a function of solvent polarizability (the sodium D line at 20° C. was used for n). FIG. 9 is a graph illustrating spectral shifts of the absorption maxima as a function of solvent polarizability for the weaker Soret and both Q absorption bands in various solvents. FIG. 10 is a graph of UV-vis absorption spectra of (top to bottom): 1-Ir(tma)$_2$, 1b-Ir(tma)$_2$, 1-Ir(py)$_2$ at room temperature in a broad range of solvents; the inset is a graph of the Soret band used for the calculation of the solvatochromic shifts discussed herein. FIG. 11 is a graph of normalized excitation profiles of (top to bottom): 1-Ir(tma)$_2$, 1b-Ir(tma)$_2$, 1-Ir(py)$_2$ monitored at emission wavelengths of 790 and 890 nm. FIG. 12 is a graph of Raman spectra of 1-Ir(tma)$_2$, 1b-Ir (tma)$_2$, 1-Ir(py)$_2$; sample excitation into the Soret was achieved with the 488 nm line of an argon ion laser. FIG. 13 is a graph of a $^1$H NMR spectrum (red) and a graph of a $^{19}$F NMR spectra (blue inserts) of 1-Ir(py)$_2$. FIG. 14 is a graph of electronic spectra of the 6-coordinate bis-pyridine metal (III) corroles (top) and the 5-coordinate PPh$_3$-coordinated metal (III) corroles (bottom), at 2.5 μM concentration in CH$_2$Cl$_2$. FIG. 15 is a series of graphs illustrating the changes in the electronic structure in CH$_2$Cl$_2$ that demonstrate (from top): the reversible transformations between 1-Co(py)$_2$ and 1-Co (PPh$_3$) upon addition of PPh$_3$ and pyridine; formation of 1-Rh(PPh$_3$)$_2$ from 1-Rh(PPh$_3$); and formation of 1-Ir(PPh$_3$)$_2$ from 1-Ir(PPh$_3$). FIG. 16 is an illustration of the molecular structure of the bis-pyridine Ir(III) corrole 1-Ir(py)$_2$ (hydrogen atoms omitted). FIG. 17 is a series of graphs of CV traces of CH$_2$Cl$_2$ solutions of the 1-M(PPh$_3$) and 1-M(py)$_2$ complexes. FIG. 18 is a series of graphs illustrating changes in the electronic spectra indicating oxidation of 1-Co(PPh$_3$) (top) and 1-Rh(PPh$_3$) (bottom) by tris(4-bromophenyl)aminium-hexachloroantimonate (t-4bpa) in CH$_2$Cl$_2$. FIG. 19 is a series of graphs illustrating changes in the electronic spectra indicating oxidation of 1-Co(py)$_2$ (top) and 1-Rh(py)$_2$ (bottom) by t-4bpa in CH$_2$Cl$_2$. FIG. 20 is a series of graphs illustrating changes in the electronic spectra indicating oxidation by t-4bpa in CH$_2$Cl$_2$ of (from top): a) 1-Ir(PPh$_3$)$_2$, up to its first oxidation product; b) 1-Ir(PPh$_3$)$_2$, starting after its first oxidation product is formed; and c) 1-Ir(py)$_2$. FIG. 21 is a graph of spectroelectrochemical results for a CH$_2$Cl$_2$ solution of 1-Ir(PPh$_3$) at 1.0 V vs. Ag/AgCl; the inset is a graph of the spectra of the starting material (red), the first oxidation product (green), and the second oxidation product (blue). FIG. 22 is a graph of spectroelectrochemical results for a CH$_2$Cl$_2$ solution of 1-Ir(PPh$_3$) containing 5 equivalents of PPh$_3$ at 1.0 V vs. Ag/AgCl; where the starting material is red and the final product is purple. FIG. 23 is a graph of electron paramagnetic resonance (EPR) spectra taken at 20 K in frozen toluene solutions (with small amounts of CH$_2$Cl$_2$ to solvate t-4bpa for the top two spectra), of the chemically oxidized forms of (clockwise from top left): a) 1-Co(py)$_2$; b) 1-Rh(py)$_2$; and c) 1-(py)$_2$; where the blue traces are the experimental spectra and the black traces are simulations performed using the SPINCOUNT package. FIG. 24 is a graph of a 300 MHz $^1$H NMR spectrum of 1-Ir(py)$_2$. FIG. 25 is a graph of a 300 MHz $^{19}$F NMR spectrum of 1-Ir(py)$_2$. FIG. 26 is a graph of an electrospray ionization mass spectrometry (EST-MS) trace for 1-Ir(py)$_2$. FIG. 27 is a graph of a 300 MHz $^1$H NMR spectrum of 1-Ir(PPh₃). FIG. 28 is a graph of a 300 MHz $^{19}$F NMR spectrum of 1-Ir(PPh₃). FIG. 29 is a graph of an ESI-MS trace for 1-Ir(PPh₃). FIG. 30 is a graph illustrating changes to the electronic absorption spectrum of 1-Co(PPh₃) in CH₂Cl₂ upon addition of excess PPh₃. FIG. 31 is a graph illustrating changes to the electronic absorption spectrum of 1-Co(PPh₃) in CH₂Cl₂ upon reaction with iodine. FIG. 32 is a graph illustrating changes to the electronic absorption spectrum of 1-Rh(PPh₃) in CH₂Cl₂ upon reaction with iodine. FIG. 33 is a graph illustrating changes to the electronic absorption spectrum of 1-Ir(PPh₃) in CH₂Cl₂ upon reaction with iodine. FIG. 34 is a graph of the electronic absorption spectrum of 1-Co(py)₂ in 5% pyridine/CH₂Cl₂. FIG. 35 is a graph of the electronic absorption spectrum of 1-Ir(PPh₃) in 5% pyridine/CH₂Cl₂, illustrating that 1-Ir(PPh₃) is not converted to 1-Ir(py)₂ under these conditions. FIG. 36 is a graph of an EPR spectrum of singly oxidized 1-Co(PPh₃), taken at 20 K in frozen toluene. FIG. 37 is a graph of an EPR spectrum of singly oxidized 1-Rh(PPh₃), taken at 20 K in frozen toluene. FIG. 38 is an illustration of the atom numbering scheme used in electronic structure calculations for compounds according to embodiments of the present invention; hydrogen atoms are in white, carbon atoms are in grey, nitrogen atoms are in blue, fluorine atoms are in green, and the metal is in lighter blue; note that the numbering of the corrole ring is different from the numbering convention of molecular nomenclature. FIG. 39 is an illustration of the molecular orbital (MO) surfaces (isovalue=−0.05) calculated for (tpfc)M(NH₃)₂, where M=Rh (left; Co shows similar results) and Ir (right); the topmost MO is the HOMO, which is followed by HOMO-1, and so on, until the MO above 1a₁ is reached; 1a₁ is HOMO-13 when M=Rh, HOMO-14 when M=Co, and HOMO-4 when M=Ir. FIG. 40 is an illustration of the relative energies and spin density surfaces (isovalue=−0.002) calculated for [(tpfc)M(NH₃)₂]⁺ (M=Co, Rh, Ir). FIG. 41 is an illustration of the relative energies and spin density surfaces (isovalue=−0.002) calculated for [(tfc)M(NH₃)₂]⁺ (M=Co, Rh, Ir). FIG. 42 is an illustration of orbital drawings and energies for [(tfc)Co(NH₃)₂]⁺ and [(tpfc)Co(NH₃)₂]⁺. FIG. 43 is an illustration of orbital drawings and energies for [(tfc)Rh(NH₃)₂]⁺ and [(tpfc)Rh(NH₃)₂]⁺. FIG. 44 is an illustration of orbital drawings and energies for [(tfc)Ir(NH₃)₂]⁺ and [(tpfc)Ir(NH₃)₂]⁰/⁺ FIG. 45 is a graph of a ¹H NMR spectrum of a platinum containing metallocorrole according to embodiments of the present invention. FIG. 46 is a graph of a correlation spectroscopy (COSY) ¹H NMR spectrum of a platinum containing metallocorrole according to embodiments of the present invention.

Metallocorrole complexes of third row transition metals may be used as therapeutic agents, catalysts, components of oxygen detectors, and components of light emitting diodes. In particular, metallocorrole complexes of third row transition metals may be used improved photosenitizers in photodynamic therapy; as improved catalysts in aziridination, epoxidation, and water splitting reactions; as improved in vivo imaging agents; and as improved components in the emissive layer of OLEDs. Due to their strongly sigma-donating nature, corroles are able to stabilize third row transition metals in high oxidation and coordination states. Third row transition metals may be significantly more electropositive than first and second transition metals and may therefore act as improved catalysts. In addition, the high spin-orbit couplings of third row transition metals couplings of third row transition metals lead to easier singlet-triplet inter-system crossing in the excited state, which in turn allows for long-wavelength phosphorescence that is desirable for many applications.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A metallocorrole according to Formula II:

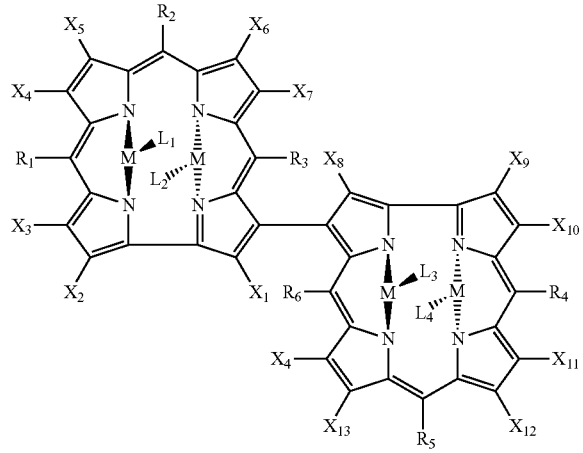

(Formula II)

wherein:
M is a third row transition metal;
each of R₁ through R₆ is independently selected from the group consisting of substituted aryl, unsubstituted aryl, and unsubstituted heteroaryl;
each of X_i through X₁₄ is independently selected from the group consisting of H, halo, formyl, carboxyl, cyanoacetyl, sulfonyl, SO₃H, SO₂NR₇R₈, COCl, CONR₇R₈, or NO₂, wherein R₇ and R₈ are the same or different, and each is selected from the group consisting of H, alkyl, aryl, and heteroaryl; and
each of L₁ through L₄ is independently selected from the group consisting of bidentate ligands.

2. The metallocorrole of claim 1, wherein M is an element selected from the group consisting of late transition metals.

3. The metallocorrole of claim 1, wherein M is Pt.

4. The metallocorrole of claim 1, wherein each of X₁ through X₁₄ is independently selected from the group consisting of H, F, Cl, and Br.

5. The metallocorrole of claim 1, wherein each of R₁ through R₆ is independently selected from the group consisting of phenyl, methylphenyl (para-tolyl), 4-aminophenyl, dichlorophenyl, 2,6-dichlorophenyl, 2,6-difluorophenyl, pentafluorophenyl, 4-methoxyphenyl, 2,5-dimethoxyphenyl, 4-methoxy-2,3,5,6-tetrafluorophenyl, 4-(pyrid-2-yl)-2,3,5,6-tetrafluorophenyl, 4-(N-methyl-pyrid-2-ylium)-2,3,5,6-tetrafluorophenyl, and 4-pyridyl.

6. The metallocorrole of claim 1, wherein each of L₁ through L₄ is cyclooctadiene.

* * * * *